United States Patent
Snyder et al.

(10) Patent No.: US 11,173,020 B2
(45) Date of Patent: Nov. 16, 2021

(54) ORAL IRRIGATOR APPLIANCE WITH RADIANT ENERGY DELIVERY FOR BACTERICIDAL EFFECT

(71) Applicant: WATER PIK, INC., Fort Collins, CO (US)

(72) Inventors: Clifford J. Snyder, Fort Collins, CO (US); Gordon Haszier, Fort Collins, CO (US); Harold A. Luettgen, Windsor, CO (US); Kenneth A. Hair, Fort Collins, CO (US); Daniel Bernard Cover, Fort Collins, CO (US)

(73) Assignee: WATER PIK, INC., Fort Collins, CO (US)

( * ) Notice: Subject to any disclaimer, the term of this patent is extended or adjusted under 35 U.S.C. 154(b) by 160 days.

(21) Appl. No.: 16/290,471

(22) Filed: Mar. 1, 2019

(65) Prior Publication Data

US 2019/0192266 A1 Jun. 27, 2019

Related U.S. Application Data

(63) Continuation of application No. 13/238,243, filed on Sep. 21, 2011, now Pat. No. 10,258,442, which is a
(Continued)

(51) Int. Cl.
*A61C 17/02* (2006.01)
*A61C 1/00* (2006.01)
(Continued)

(52) U.S. Cl.
CPC ........ *A61C 17/0202* (2013.01); *A61C 1/0046* (2013.01); *A61C 17/024* (2019.05);
(Continued)

(58) Field of Classification Search
CPC . A61C 17/02; A61C 17/0202; A61C 17/0046; A61B 18/20–202; A61B 18/206
See application file for complete search history.

(56) References Cited

U.S. PATENT DOCUMENTS

| 555,588 | A | 3/1896 | Spencer |
| 1,278,225 | A | 9/1918 | Scharnberg |

(Continued)

FOREIGN PATENT DOCUMENTS

| CA | 851479 | 9/1970 |
| CH | 502817 | 2/1971 |

(Continued)

OTHER PUBLICATIONS

US RE27,274 E, 01/1972, Mattingly (withdrawn)
(Continued)

*Primary Examiner* — Nathan J Jenness
(74) *Attorney, Agent, or Firm* — Dorsey & Whitney LLP

(57) ABSTRACT

An oral irrigator includes a base having a pump mechanism, a reservoir housed within the base and fluidically connected with the pump mechanism. A handle with a jet tip is connected with an outlet from the pump mechanism to receive a pressurized fluid stream from the reservoir to direct a fluid at a surface inside an oral cavity. The oral irrigator also includes a radiant energy source and delivery system for directing radiant energy at a surface inside an oral cavity.

23 Claims, 27 Drawing Sheets

Related U.S. Application Data continuation-in-part of application No. 12/729,076, filed on Mar. 22, 2010, now abandoned.

(60) Provisional application No. 61/385,554, filed on Sep. 22, 2010, provisional application No. 61/162,126, filed on Mar. 20, 2009.

(51) Int. Cl.
*A61L 2/00* (2006.01)
*A61C 17/024* (2006.01)
*A61N 5/06* (2006.01)
*A61C 1/08* (2006.01)

(52) U.S. Cl.
CPC ........... *A61L 2/0047* (2013.01); *A61L 2/0052* (2013.01); *A61C 1/088* (2013.01); *A61N 2005/0606* (2013.01)

(56) References Cited

U.S. PATENT DOCUMENTS

| | | |
|---|---|---|
| 1,452,258 A | 4/1923 | Smith |
| 1,464,419 A | 8/1923 | Gill |
| 1,480,310 A | 1/1924 | Smith |
| 1,498,267 A | 6/1924 | Hachman |
| 1,602,742 A | 10/1926 | Bennet |
| 1,650,686 A | 11/1927 | Binks |
| 1,669,889 A | 5/1928 | Andrews et al. |
| 1,681,320 A | 8/1928 | Bergl et al. |
| 1,933,454 A | 10/1933 | Sidney |
| 1,940,111 A | 12/1933 | Austin |
| D93,019 S | 8/1934 | Hose |
| 1,977,782 A | 10/1934 | Roy |
| 2,107,686 A | 2/1938 | Bramsen et al. |
| 2,421,498 A | 6/1947 | Guedel |
| D159,872 S | 8/1950 | Skold |
| 2,531,730 A | 11/1950 | Henderson |
| 2,595,666 A | 5/1952 | Hutson |
| 2,669,233 A | 2/1954 | Friend |
| 2,794,437 A | 6/1954 | Tash |
| 2,709,227 A | 5/1955 | Foley et al. |
| 2,733,713 A | 2/1956 | Kabnick |
| 2,783,919 A | 3/1957 | Ansell |
| 2,870,932 A | 1/1959 | Davis |
| 2,984,452 A | 5/1961 | Hooper |
| 3,089,490 A | 5/1963 | Goldberg |
| 3,096,913 A | 7/1963 | Jousson |
| 3,144,867 A | 8/1964 | Trupp et al. |
| D202,041 S | 8/1965 | Burzlaff |
| 3,209,956 A | 10/1965 | McKenzie |
| 3,216,619 A | 11/1965 | Richards et al. |
| 3,225,759 A | 12/1965 | Drapen et al. |
| 3,227,158 A | 1/1966 | Mattingly |
| 3,266,623 A | 8/1966 | Poferl |
| 3,297,558 A | 1/1967 | Hillquist |
| D208,778 S | 10/1967 | Koch |
| D209,202 S | 11/1967 | Fulton et al. |
| D209,203 S | 11/1967 | Mattingly et al. |
| D209,204 S | 11/1967 | St. Clair et al. |
| D209,395 S | 11/1967 | Gilbert |
| D210,018 S | 1/1968 | Mattingly et al. |
| D210,019 S | 1/1968 | Johnson et al. |
| 3,370,214 A | 2/1968 | Aymar |
| 3,391,696 A | 7/1968 | Woodward |
| 3,393,673 A | 7/1968 | Mattingly et al. |
| 3,400,999 A | 9/1968 | Goldstein |
| 3,418,552 A | 12/1968 | Holmes |
| 3,420,228 A | 1/1969 | Kalbfeld |
| 3,425,410 A | 2/1969 | Cammack |
| 3,453,969 A | 7/1969 | Mattingly |
| 3,465,751 A | 9/1969 | Powers |
| 3,467,083 A | 9/1969 | Mattingly |
| 3,467,286 A | 9/1969 | Ostrowsky |
| D215,920 S | 11/1969 | McCarty et al. |
| 3,487,828 A | 1/1970 | Troy |
| 3,489,268 A | 1/1970 | Meierhoefer |
| 3,495,587 A | 2/1970 | Freedman |
| 3,496,933 A | 2/1970 | Lloyd |
| 3,499,440 A | 3/1970 | Gibbs |
| 3,500,824 A | 3/1970 | Gilbert |
| 3,501,203 A | 3/1970 | Falk |
| 3,502,072 A | 3/1970 | Stillman |
| 3,517,669 A | 6/1970 | Buono et al. |
| D218,270 S | 8/1970 | Soper |
| 3,522,801 A | 8/1970 | Robinson |
| 3,532,221 A | 10/1970 | Kaluhiokalani et al. |
| 3,536,065 A | 10/1970 | Moret |
| 3,537,444 A | 11/1970 | Garn |
| 3,538,950 A | 11/1970 | Porteners |
| 3,547,110 A | 12/1970 | Balamuth |
| 3,561,433 A | 2/1971 | Kovach |
| D220,334 S | 3/1971 | Mackay et al. |
| 3,570,525 A | 3/1971 | Borsum |
| 3,572,375 A | 3/1971 | Rosenberg |
| 3,578,884 A | 5/1971 | Jacobson |
| D220,996 S | 6/1971 | Irons |
| 3,583,609 A | 6/1971 | Oppenheimer |
| 3,590,813 A | 7/1971 | Roszyk |
| 3,608,548 A | 9/1971 | Lewis |
| 3,612,045 A | 10/1971 | Dudas |
| D222,862 S | 1/1972 | Cook |
| 3,636,947 A | 1/1972 | Balamuth |
| 3,651,576 A | 3/1972 | Massa |
| 3,669,101 A | 6/1972 | Kleiner |
| 3,703,170 A | 11/1972 | Ryckman, Jr. |
| 3,718,974 A | 3/1973 | Buchtel et al. |
| 3,747,595 A | 7/1973 | Grossan |
| 3,768,472 A | 10/1973 | Hodosh et al. |
| 3,771,186 A | 11/1973 | Moret et al. |
| 3,783,364 A | 1/1974 | Gallanis et al. |
| 3,809,506 A | 5/1974 | Malcosky |
| 3,809,977 A | 5/1974 | Balamuth et al. |
| 3,811,432 A | 5/1974 | Moret |
| 3,820,532 A | 6/1974 | Eberhardt et al. |
| 3,827,147 A | 8/1974 | Condon |
| 3,837,166 A | 9/1974 | Hiraoka |
| 3,840,795 A | 10/1974 | Roszyk et al. |
| 3,847,145 A | 11/1974 | Grossan |
| 3,854,209 A | 12/1974 | Franklin et al. |
| 3,863,628 A | 2/1975 | Vit |
| 3,871,560 A | 3/1975 | Crippa |
| 3,874,506 A | 4/1975 | Hill et al. |
| 3,911,796 A | 10/1975 | Hull et al. |
| 3,912,125 A | 10/1975 | Acklin |
| 3,943,628 A | 3/1976 | Kronman et al. |
| 3,959,883 A | 6/1976 | Walls et al. |
| 3,973,558 A | 8/1976 | Stouffer et al. |
| 3,977,084 A | 8/1976 | Sloan |
| 4,001,526 A | 1/1977 | Olson |
| 4,004,302 A | 1/1977 | Hori |
| 4,007,739 A | 2/1977 | Bron et al. |
| 4,013,227 A | 3/1977 | Herrera |
| 4,022,114 A | 5/1977 | Hansen, III |
| 4,052,002 A | 10/1977 | Stouffer et al. |
| D246,667 S | 12/1977 | Mackay et al. |
| D246,668 S | 12/1977 | Mackay et al. |
| 4,060,870 A | 12/1977 | Cannarella |
| 4,075,761 A | 2/1978 | Behne et al. |
| 4,078,558 A | 3/1978 | Woog et al. |
| 4,089,079 A | 5/1978 | Nicholson |
| 4,094,311 A | 6/1978 | Hudson |
| 4,108,167 A | 8/1978 | Hickman et al. |
| 4,108,178 A | 8/1978 | Betush |
| 4,109,650 A | 8/1978 | Peclard |
| 4,122,845 A | 10/1978 | Stouffer et al. |
| 4,133,971 A | 1/1979 | Boyd et al. |
| 4,135,501 A | 1/1979 | Leunissan |
| 4,141,352 A | 2/1979 | Ebner et al. |
| 4,144,646 A | 3/1979 | Takemoto et al. |
| 4,149,315 A | 4/1979 | Page, Jr. et al. |
| 4,154,375 A | 5/1979 | Bippus |
| 4,160,383 A | 7/1979 | Rauschenberger |
| 4,171,572 A | 10/1979 | Nash |

(56) References Cited

U.S. PATENT DOCUMENTS

| | | |
|---|---|---|
| 4,182,038 A | 1/1980 | Fleer |
| 4,200,235 A | 4/1980 | Monschke |
| 4,201,200 A | 5/1980 | Hubner |
| 4,210,380 A | 7/1980 | Brzostek |
| 4,215,476 A | 8/1980 | Armstrong |
| 4,219,618 A | 8/1980 | Leonard |
| 4,227,878 A | 10/1980 | Lohn |
| 4,229,634 A | 10/1980 | Hickman et al. |
| 4,236,889 A | 12/1980 | Wright |
| D258,097 S | 2/1981 | Wistrand |
| 4,248,589 A | 2/1981 | Lewis |
| 4,249,899 A | 2/1981 | Davis |
| 4,257,458 A | 3/1981 | Kondo et al. |
| 4,262,799 A | 4/1981 | Perrett |
| 4,266,934 A | 5/1981 | Pernot |
| 4,276,023 A | 6/1981 | Phillips et al. |
| 4,276,880 A | 7/1981 | Malmin |
| 4,302,186 A | 11/1981 | Cammack et al. |
| 4,303,064 A | 12/1981 | Buffa |
| 4,303,070 A | 12/1981 | Ichikawa et al. |
| 4,306,862 A | 12/1981 | Knox |
| 4,315,741 A | 2/1982 | Reichl |
| 4,319,568 A | 4/1982 | Tregoning |
| 4,331,422 A | 5/1982 | Heyman |
| 4,337,040 A | 6/1982 | Cammack et al. |
| 4,340,365 A | 7/1982 | Pisanu |
| 4,340,368 A | 7/1982 | Lococo |
| D266,117 S | 9/1982 | Oberheim |
| 4,353,694 A | 10/1982 | Pelerin |
| 4,363,626 A | 12/1982 | Schmidt et al. |
| 4,365,376 A | 12/1982 | Oda et al. |
| 4,370,131 A | 1/1983 | Banko |
| 4,374,354 A | 2/1983 | Petrovic et al. |
| 4,382,167 A | 5/1983 | Maruyama et al. |
| 4,382,786 A | 5/1983 | Lohn |
| D270,000 S | 8/1983 | Ketler |
| 4,396,011 A | 8/1983 | Mack et al. |
| 4,412,823 A | 11/1983 | Sakai et al. |
| 4,416,628 A | 11/1983 | Cammack |
| 4,442,830 A | 4/1984 | Markau |
| 4,442,831 A | 4/1984 | Trenary |
| 4,452,238 A | 6/1984 | Kerr |
| 4,454,866 A | 6/1984 | Fayen |
| 4,512,769 A | 4/1985 | Kozam et al. |
| 4,517,962 A | 5/1985 | Heckele |
| 4,531,912 A | 7/1985 | Schuss et al. |
| 4,531,913 A | 7/1985 | Taguchi |
| 4,534,340 A | 8/1985 | Kerr et al. |
| 4,552,130 A | 11/1985 | Kinoshita |
| 4,561,214 A | 12/1985 | Inoue |
| D283,374 S | 4/1986 | Cheuk-Yiu |
| 4,585,415 A | 4/1986 | Hammann |
| 4,591,777 A | 5/1986 | McCarty et al. |
| 4,592,728 A | 6/1986 | Davis |
| 4,602,906 A | 7/1986 | Grunenfelder |
| 4,607,627 A | 8/1986 | Leber et al. |
| 4,613,074 A | 9/1986 | Schulze |
| 4,619,009 A | 10/1986 | Rosenstatter |
| 4,619,612 A | 10/1986 | Weber et al. |
| 4,629,425 A | 12/1986 | Detsch |
| 4,636,198 A | 1/1987 | Stade |
| 4,642,037 A | 2/1987 | Fritchman |
| 4,644,937 A | 2/1987 | Hammann |
| 4,645,488 A | 2/1987 | Matukas |
| 4,647,831 A | 3/1987 | O'Malley et al. |
| 4,648,838 A | 3/1987 | Schlachter |
| 4,650,475 A | 3/1987 | Smith et al. |
| 4,655,198 A | 4/1987 | Hammann |
| 4,669,453 A | 6/1987 | Atkinson et al. |
| 4,672,953 A | 6/1987 | DiVito |
| 4,673,396 A | 6/1987 | Urbaniak |
| D291,354 S | 8/1987 | Camens |
| 4,716,352 A | 12/1987 | Hurn et al. |
| 4,749,340 A | 6/1988 | Ikeda et al. |
| 4,770,632 A | 9/1988 | Ryder et al. |
| D298,565 S | 11/1988 | Kohler, Jr. et al. |
| 4,783,321 A | 11/1988 | Spence |
| 4,787,845 A | 11/1988 | Valentine |
| 4,787,847 A | 11/1988 | Martin et al. |
| 4,798,292 A | 1/1989 | Hauze |
| 4,803,974 A | 2/1989 | Powell |
| 4,804,364 A | 2/1989 | Dieras et al. |
| 4,810,148 A | 3/1989 | Aisa et al. |
| 4,818,229 A | 4/1989 | Vasile |
| 4,820,152 A | 4/1989 | Warrin et al. |
| 4,821,923 A | 4/1989 | Skorka |
| 4,824,368 A | 4/1989 | Hickman |
| 4,826,431 A * | 5/1989 | Fujimura ............ A61C 1/0046 433/29 |
| 4,827,551 A | 5/1989 | Maser et al. |
| 4,832,683 A | 5/1989 | Idemoto et al. |
| 4,854,869 A | 8/1989 | Lawhorn |
| 4,861,340 A | 8/1989 | Smith et al. |
| 4,862,876 A | 9/1989 | Uh-Sheng |
| 4,864,918 A | 9/1989 | Martin |
| 4,869,720 A | 9/1989 | Chernack |
| 4,880,382 A | 11/1989 | Moret et al. |
| 4,886,452 A | 12/1989 | Lohn |
| 4,900,252 A | 2/1990 | Liefke et al. |
| 4,902,225 A | 2/1990 | Lohn |
| 4,903,687 A | 2/1990 | Uh-Sheng |
| 4,906,187 A | 3/1990 | Amadera |
| 4,907,744 A | 3/1990 | Jousson |
| 4,915,304 A | 4/1990 | Campani |
| 4,925,450 A | 5/1990 | Imonti et al. |
| 4,928,675 A | 5/1990 | Thornton |
| 4,930,660 A | 6/1990 | Porteous |
| 4,941,459 A | 7/1990 | Mathur |
| 4,950,159 A | 8/1990 | Hansen |
| 4,958,629 A | 9/1990 | Peace et al. |
| 4,958,751 A | 9/1990 | Curtis et al. |
| 4,959,199 A | 9/1990 | Brewer |
| 4,961,698 A | 10/1990 | Vlock |
| 4,966,551 A | 10/1990 | Betush |
| 4,969,874 A | 11/1990 | Michel et al. |
| 4,973,246 A | 11/1990 | Black |
| 4,973,247 A | 11/1990 | Varnes et al. |
| 4,973,250 A | 11/1990 | Milman |
| 4,975,054 A | 12/1990 | Esrock |
| 4,979,503 A | 12/1990 | Chernack |
| 4,979,504 A | 12/1990 | Mills |
| 4,989,590 A | 2/1991 | Baum et al. |
| 4,998,880 A | 3/1991 | Nerli |
| 5,013,241 A | 5/1991 | Von Gutfeld et al. |
| 5,014,884 A | 5/1991 | Wunsch |
| 5,019,054 A | 5/1991 | Clement et al. |
| 5,027,798 A | 7/1991 | Primiano |
| 5,029,576 A | 7/1991 | Evans, Sr. |
| 5,033,617 A | 7/1991 | Hartwein et al. |
| 5,033,961 A | 7/1991 | Kankler et al. |
| D318,918 S | 8/1991 | Hartwein |
| 5,046,486 A | 9/1991 | Grulke et al. |
| 5,049,071 A | 9/1991 | Davis et al. |
| 5,060,825 A | 10/1991 | Palmer et al. |
| 5,061,180 A | 10/1991 | Wiele |
| 5,062,795 A | 11/1991 | Woog |
| 5,064,168 A | 11/1991 | Raines et al. |
| D322,314 S | 12/1991 | Ohbayashi |
| 5,071,346 A | 12/1991 | Domaas |
| 5,082,115 A | 1/1992 | Hutcheson |
| 5,082,443 A | 1/1992 | Lohn |
| 5,085,317 A | 2/1992 | Jensen et al. |
| 5,086,756 A | 2/1992 | Powell |
| 5,095,893 A | 3/1992 | Rawden, Jr. |
| 5,098,291 A | 3/1992 | Curtis et al. |
| 5,098,676 A | 3/1992 | Brooks, Jr. |
| 5,100,319 A | 3/1992 | Baum |
| 5,117,871 A | 6/1992 | Gardner et al. |
| 5,125,835 A | 6/1992 | Young |
| 5,127,831 A | 7/1992 | Bab |
| 5,142,723 A | 9/1992 | Lustig et al. |
| 5,150,841 A | 9/1992 | Silvenis et al. |
| 5,172,810 A | 12/1992 | Brewer |
| 5,173,273 A | 12/1992 | Brewer |

(56) References Cited

U.S. PATENT DOCUMENTS

| | | |
|---|---|---|
| 5,183,035 A | 2/1993 | Weir |
| 5,197,458 A | 3/1993 | Ito et al. |
| 5,197,460 A | 3/1993 | Ito et al. |
| 5,199,871 A | 4/1993 | Young |
| 5,203,697 A | 4/1993 | Malmin |
| 5,203,769 A | 4/1993 | Clement et al. |
| 5,204,004 A | 4/1993 | Johnston et al. |
| 5,208,933 A | 5/1993 | Lustig et al. |
| 5,215,193 A | 6/1993 | Dennis |
| 5,218,956 A | 6/1993 | Handler et al. |
| 5,220,914 A | 6/1993 | Thompson |
| 5,228,646 A | 7/1993 | Raines |
| 5,230,624 A | 7/1993 | Wolf et al. |
| 5,232,687 A | 8/1993 | Geimer |
| 5,235,968 A | 8/1993 | Woog |
| 5,241,714 A | 9/1993 | Barry |
| 5,246,367 A | 9/1993 | Ito et al. |
| 5,252,064 A | 10/1993 | Baum et al. |
| D341,200 S | 11/1993 | Yoshimoto |
| 5,257,933 A | 11/1993 | Jousson |
| 5,261,448 A | 11/1993 | Furuya et al. |
| D341,943 S | 12/1993 | Si-Hoe |
| 5,267,586 A | 12/1993 | Jankavaara |
| 5,269,684 A | 12/1993 | Fischer |
| 5,281,137 A | 1/1994 | Jousson |
| 5,281,139 A | 1/1994 | Frank et al. |
| 5,282,745 A | 2/1994 | Wiltrout et al. |
| 5,286,192 A | 2/1994 | Dixon |
| 5,286,201 A | 2/1994 | Yu |
| 5,295,832 A | 3/1994 | Evans |
| 5,297,962 A | 3/1994 | O'Connor et al. |
| D346,212 S | 4/1994 | Hosl |
| 5,301,381 A | 4/1994 | Klupt |
| 5,302,123 A | 4/1994 | Bechard |
| 5,317,691 A | 5/1994 | Traeger |
| 5,321,865 A | 6/1994 | Kaeser |
| 5,323,770 A | 6/1994 | Ito et al. |
| 5,331,704 A | 7/1994 | Rosen et al. |
| 5,344,317 A | 9/1994 | Pacher et al. |
| 5,346,677 A | 9/1994 | Risk |
| 5,349,896 A | 9/1994 | Delaney |
| D351,892 S | 10/1994 | Wolf et al. |
| 5,360,338 A | 11/1994 | Waggoner |
| 5,368,548 A | 11/1994 | Jousson |
| 5,370,534 A | 12/1994 | Wolf et al. |
| D354,168 S | 1/1995 | Hartwein |
| D354,559 S | 1/1995 | Knute |
| 5,378,149 A | 1/1995 | Stropko |
| 5,380,201 A | 1/1995 | Kawata |
| D356,864 S | 3/1995 | Woog |
| 5,399,089 A | 3/1995 | Eichman et al. |
| D358,883 S | 5/1995 | Vos |
| 5,456,672 A | 10/1995 | Diederich et al. |
| 5,465,445 A | 11/1995 | Yeh |
| 5,467,495 A | 11/1995 | Boland et al. |
| 5,468,148 A | 11/1995 | Ricks |
| 5,470,305 A | 11/1995 | Arnett et al. |
| 5,474,450 A | 12/1995 | Chronister |
| 5,474,451 A | 12/1995 | Dalrymple et al. |
| 5,476,379 A | 12/1995 | Disel |
| 5,484,281 A | 1/1996 | Renow et al. |
| 5,487,877 A | 1/1996 | Choi |
| 5,490,779 A | 2/1996 | Malmin |
| 5,505,916 A | 4/1996 | Berry, Jr. |
| D369,656 S | 5/1996 | Vos |
| D370,125 S | 5/1996 | Craft et al. |
| 5,525,058 A | 6/1996 | Gallant et al. |
| 5,526,841 A | 6/1996 | Detsch et al. |
| 5,540,587 A | 7/1996 | Malmin |
| 5,547,374 A | 8/1996 | Coleman |
| D373,631 S | 9/1996 | Maeda et al. |
| 5,554,014 A | 9/1996 | Becker |
| 5,554,025 A | 9/1996 | Kinsel |
| 5,556,001 A | 9/1996 | Weissman et al. |
| 5,564,629 A | 10/1996 | Weissman et al. |
| D376,893 S | 12/1996 | Gornet |
| D377,091 S | 12/1996 | Scott, Sr. |
| 5,613,259 A | 3/1997 | Craft et al. |
| 5,616,028 A | 4/1997 | Hafele et al. |
| 5,622,501 A * | 4/1997 | Levy ................. A61C 1/0046 433/215 |
| 5,626,472 A | 5/1997 | Pennetta |
| 5,634,791 A | 6/1997 | Matsuura et al. |
| 5,636,987 A | 6/1997 | Serfaty |
| 5,640,735 A | 6/1997 | Manning |
| D382,407 S | 8/1997 | Craft et al. |
| 5,653,591 A | 8/1997 | Loge |
| 5,658,148 A | 8/1997 | Neuberger et al. |
| 5,659,995 A | 8/1997 | Huffman |
| 5,667,483 A | 9/1997 | Santos |
| D386,576 S | 11/1997 | Wang et al. |
| 5,683,192 A | 11/1997 | Kilfoil |
| 5,685,829 A | 11/1997 | Allen |
| 5,685,851 A | 11/1997 | Murphy et al. |
| 5,697,784 A | 12/1997 | Hafele et al. |
| D388,612 S | 1/1998 | Stutzer et al. |
| D388,613 S | 1/1998 | Stutzer et al. |
| D389,091 S | 1/1998 | Dickinson |
| 5,709,545 A | 1/1998 | Johnston et al. |
| D390,934 S | 2/1998 | McKeone |
| 5,716,007 A | 2/1998 | Nottingham et al. |
| 5,718,668 A | 2/1998 | Arnett et al. |
| 5,746,595 A | 5/1998 | Ford |
| 5,749,726 A | 5/1998 | Kinsel |
| 5,759,502 A | 6/1998 | Spencer et al. |
| 5,779,471 A | 7/1998 | Tseng et al. |
| 5,779,654 A | 7/1998 | Foley et al. |
| 5,795,153 A * | 8/1998 | Rechmann ........... A61C 1/0046 433/216 |
| 5,796,325 A | 8/1998 | Lundell et al. |
| 5,833,065 A | 11/1998 | Burgess |
| 5,836,030 A | 11/1998 | Hazeu et al. |
| D402,744 S | 12/1998 | Zuege |
| 5,851,079 A | 12/1998 | Horstman et al. |
| D403,511 S | 1/1999 | Serbinski |
| D406,334 S | 3/1999 | Rosenthal et al. |
| 5,876,201 A | 3/1999 | Wilson et al. |
| D408,511 S | 4/1999 | Allen et al. |
| 5,901,397 A | 5/1999 | Häfele et al. |
| 5,934,902 A | 8/1999 | Abahusayn |
| D413,975 S | 9/1999 | Maeda |
| D416,999 S | 11/1999 | Miyamoto |
| D417,082 S | 11/1999 | Classen et al. |
| 5,993,402 A | 11/1999 | Sauer et al. |
| 6,030,215 A | 2/2000 | Ellion et al. |
| 6,038,960 A | 3/2000 | Fukushima et al. |
| 6,039,180 A | 3/2000 | Grant |
| 6,041,462 A | 3/2000 | Marques |
| 6,047,429 A | 4/2000 | Wu |
| D424,181 S | 5/2000 | Caplow |
| D425,615 S | 5/2000 | Bachman et al. |
| D425,981 S | 5/2000 | Bachman et al. |
| 6,056,548 A | 5/2000 | Neuberger et al. |
| 6,056,710 A | 5/2000 | Bachman et al. |
| D426,633 S | 6/2000 | Bachman et al. |
| 6,089,865 A | 7/2000 | Edgar |
| 6,116,866 A | 9/2000 | Tomita et al. |
| 6,120,755 A | 9/2000 | Jacobs |
| 6,124,699 A | 9/2000 | Suzuki et al. |
| D434,500 S | 11/2000 | Pollock et al. |
| 6,159,006 A | 12/2000 | Cook et al. |
| 6,164,967 A | 12/2000 | Sale et al. |
| D435,905 S | 1/2001 | Bachman et al. |
| D437,049 S | 1/2001 | Hartwein |
| 6,193,512 B1 | 2/2001 | Wallace |
| 6,193,932 B1 | 2/2001 | Wu et al. |
| 6,199,239 B1 | 3/2001 | Dickerson |
| 6,200,134 B1 | 3/2001 | Kovac |
| D439,781 S | 4/2001 | Spore |
| 6,217,835 B1 | 4/2001 | Riley et al. |
| D441,861 S | 5/2001 | Hafliger |
| 6,230,717 B1 | 5/2001 | Marx et al. |
| 6,233,773 B1 | 5/2001 | Karge et al. |
| 6,234,205 B1 | 5/2001 | D'Amelio et al. |

(56) References Cited

U.S. PATENT DOCUMENTS

| | | |
|---|---|---|
| 6,237,178 B1 | 5/2001 | Krammer et al. |
| 6,247,929 B1 | 6/2001 | Bachman et al. |
| 6,280,190 B1 | 8/2001 | Hoffman |
| D448,236 S | 9/2001 | Murray |
| 6,293,792 B1 | 9/2001 | Hanson |
| D449,884 S | 10/2001 | Tobin et al. |
| 6,299,419 B1 | 10/2001 | Hunklinger |
| 6,343,174 B1 | 1/2002 | Neuberger |
| D453,453 S | 2/2002 | Lun |
| D455,201 S | 4/2002 | Jones |
| D455,203 S | 4/2002 | Jones |
| 6,363,565 B1 | 4/2002 | Paffrath |
| D457,949 S | 5/2002 | Krug |
| D464,799 S | 10/2002 | Crossman et al. |
| 6,468,482 B1 | 10/2002 | Frieze et al. |
| 6,475,173 B1 | 11/2002 | Bachman et al. |
| 6,485,451 B1 | 11/2002 | Roberts et al. |
| 6,497,375 B1 | 12/2002 | Srinath et al. |
| 6,497,572 B2 | 12/2002 | Hood et al. |
| D468,422 S | 1/2003 | McCurrach |
| 6,502,584 B1 | 1/2003 | Fordham |
| D470,660 S | 2/2003 | Schaber |
| 6,532,837 B1 | 3/2003 | Magussen, Jr. |
| 6,558,344 B2 | 5/2003 | McKinnon et al. |
| 6,561,808 B2 * | 5/2003 | Neuberger ............ A61N 5/062 433/215 |
| D475,346 S | 6/2003 | McCurrach et al. |
| D476,743 S | 7/2003 | D'Silva |
| 6,589,477 B1 | 7/2003 | Frieze et al. |
| 6,602,071 B1 | 8/2003 | Ellion et al. |
| 6,632,091 B1 | 10/2003 | Cise et al. |
| D482,451 S | 11/2003 | Page et al. |
| 6,640,999 B2 | 11/2003 | Peterson |
| 6,647,577 B2 | 11/2003 | Tam |
| 6,659,674 B2 | 12/2003 | Carlucci et al. |
| 6,663,386 B1 | 12/2003 | Moelsgaard |
| 6,669,059 B2 | 12/2003 | Mehta |
| D484,971 S | 1/2004 | Hartwein |
| 6,681,418 B1 | 1/2004 | Bierend |
| D486,573 S | 2/2004 | Callaghan et al. |
| 6,689,078 B1 | 2/2004 | Rehkemper et al. |
| 6,699,208 B2 | 3/2004 | Bachman et al. |
| 6,719,561 B2 | 4/2004 | Gugel et al. |
| D489,183 S | 5/2004 | Akahori et al. |
| 6,739,782 B1 | 5/2004 | Rehkemper et al. |
| 6,740,053 B2 | 5/2004 | Kaplowitz |
| D490,899 S | 6/2004 | Gagnon |
| D491,728 S | 6/2004 | Jimenez |
| D492,996 S | 7/2004 | Rehkemper et al. |
| 6,758,845 B1 | 7/2004 | Weckwerth et al. |
| 6,761,324 B2 | 7/2004 | Chang |
| 6,766,549 B2 | 7/2004 | Klupt |
| D495,142 S | 8/2004 | Berde |
| D495,143 S | 8/2004 | Berde |
| 6,779,216 B2 | 8/2004 | Davies et al. |
| 6,783,004 B1 | 8/2004 | Rinner |
| 6,783,505 B1 | 8/2004 | Lai |
| 6,796,796 B2 | 9/2004 | Segal |
| 6,808,331 B2 | 10/2004 | Hall et al. |
| D498,643 S | 11/2004 | Pryor, Jr. et al. |
| 6,814,259 B1 | 11/2004 | Foster et al. |
| D499,885 S | 12/2004 | Xi |
| 6,835,181 B2 | 12/2004 | Hippensteel |
| D500,599 S | 1/2005 | Callaghan |
| 6,836,917 B2 | 1/2005 | Blaustein et al. |
| 6,837,708 B2 | 1/2005 | Chen et al. |
| 6,884,069 B2 | 4/2005 | Goldman |
| 6,902,337 B1 | 6/2005 | Kuo |
| 6,907,879 B2 | 6/2005 | Drinan et al. |
| D509,585 S | 9/2005 | Kling et al. |
| D513,638 S | 1/2006 | Pan |
| D515,215 S | 2/2006 | Wang |
| D522,652 S | 6/2006 | Massey |
| 7,080,980 B2 | 7/2006 | Klupt |
| D529,661 S | 10/2006 | Schmidt |
| D530,010 S | 10/2006 | Luettgen et al. |
| 7,117,555 B2 | 10/2006 | Fattori et al. |
| D532,570 S | 11/2006 | Vizcarra |
| 7,131,838 B2 | 11/2006 | Suzuki et al. |
| D533,720 S | 12/2006 | Vu |
| 7,147,468 B2 | 12/2006 | Snyder et al. |
| D538,474 S | 3/2007 | Sheppard et al. |
| D548,334 S | 8/2007 | Izumi |
| D550,097 S | 9/2007 | Lepoitevin |
| D553,980 S | 10/2007 | VerWeyst |
| 7,276,035 B2 | 10/2007 | Lu |
| 7,314,456 B2 | 1/2008 | Shaw |
| D563,674 S | 3/2008 | Beedham |
| D565,175 S | 3/2008 | Boyd et al. |
| 7,344,510 B1 | 3/2008 | Yande |
| D565,713 S | 4/2008 | Gao |
| 7,367,803 B2 | 5/2008 | Egeresi |
| D574,952 S | 8/2008 | Boyd et al. |
| 7,410,283 B2 * | 8/2008 | West ................... A61C 19/004 362/327 |
| 7,414,337 B2 | 8/2008 | Wilkinson et al. |
| D577,198 S | 9/2008 | Jimenez et al. |
| D577,814 S | 9/2008 | Seki et al. |
| D581,279 S | 11/2008 | Oates |
| 7,455,521 B2 | 11/2008 | Fishburne, Jr. |
| 7,469,440 B2 | 12/2008 | Boland et al. |
| D585,132 S | 1/2009 | Pukall |
| D588,262 S | 3/2009 | Pukall |
| 7,500,584 B2 | 3/2009 | Schutz |
| D590,492 S | 4/2009 | Powell |
| D592,748 S | 5/2009 | Boulton |
| D595,136 S | 6/2009 | Canamasas Puigbo |
| D601,694 S | 10/2009 | Rocklin |
| D601,697 S | 10/2009 | Sobeich et al. |
| D603,708 S | 11/2009 | Handy |
| D608,430 S | 1/2010 | Slothower |
| 7,670,141 B2 | 3/2010 | Thomas et al. |
| 7,677,888 B1 | 3/2010 | Halm |
| D613,550 S | 4/2010 | Picozza et al. |
| D621,949 S | 8/2010 | Seki et al. |
| D622,928 S | 9/2010 | Griebel |
| D623,376 S | 9/2010 | Griebel |
| D625,105 S | 10/2010 | Winkler |
| D625,406 S | 10/2010 | Seki et al. |
| 7,814,585 B1 | 10/2010 | Reich |
| D629,884 S | 12/2010 | Stephens |
| 7,857,623 B2 | 12/2010 | Grez |
| 7,862,536 B2 | 1/2011 | Chen et al. |
| 7,878,403 B2 | 2/2011 | Hennick et al. |
| 7,959,597 B2 | 6/2011 | Baker et al. |
| D640,872 S | 7/2011 | Nanda |
| D648,539 S | 11/2011 | Wai |
| D648,941 S | 11/2011 | Leung |
| D651,805 S | 1/2012 | Hay |
| D653,340 S | 1/2012 | Goerge et al. |
| 8,113,832 B2 | 2/2012 | Snyder et al. |
| D655,380 S | 3/2012 | Taylor |
| D658,381 S | 5/2012 | Gebski |
| D658,538 S | 5/2012 | Korzeniowski |
| 8,220,726 B2 | 7/2012 | Qiu et al. |
| D666,912 S | 9/2012 | Kawai |
| 8,256,979 B2 | 9/2012 | Hilscher et al. |
| D668,339 S | 10/2012 | Luoto |
| D669,169 S | 10/2012 | Washington et al. |
| 8,297,534 B2 | 10/2012 | Li et al. |
| D670,958 S | 11/2012 | Picozza et al. |
| D671,637 S | 11/2012 | Gebski et al. |
| D672,018 S | 12/2012 | Bucher |
| 8,366,024 B2 | 2/2013 | Leber |
| 8,403,577 B2 | 3/2013 | Khoshnevis |
| 8,418,300 B2 | 4/2013 | Miller et al. |
| D686,311 S | 7/2013 | Mori |
| D694,378 S | 11/2013 | Bates |
| D694,398 S | 11/2013 | Taylor |
| D700,343 S | 2/2014 | Liu |
| D702,819 S | 4/2014 | Garland |
| D702,821 S | 4/2014 | Garland |
| D707,350 S | 6/2014 | Woodard |
| 8,801,667 B2 | 8/2014 | Taylor |

(56) References Cited

U.S. PATENT DOCUMENTS

| | | |
|---|---|---|
| D717,547 S | 11/2014 | Adriaenssen |
| D719,737 S | 12/2014 | Adriaenssen |
| D731,640 S | 6/2015 | Kim et al. |
| 9,050,157 B2 | 6/2015 | Boyd et al. |
| D740,936 S | 10/2015 | Kim et al. |
| D747,464 S | 1/2016 | Taylor |
| D773,822 S | 12/2016 | Sikora |
| D782,657 S | 3/2017 | Williams |
| D798,059 S | 7/2017 | McGarry |
| D799,217 S | 10/2017 | Massee |
| 2002/0090252 A1 | 7/2002 | Hall et al. |
| 2002/0108193 A1 | 8/2002 | Gruber |
| 2002/0119415 A1 | 8/2002 | Bailey |
| 2002/0152565 A1 | 10/2002 | Klupt |
| 2002/0182186 A1* | 12/2002 | Loeb ............ C12N 5/0663 424/93.7 |
| 2003/0060743 A1 | 3/2003 | Chang |
| 2003/0098249 A1 | 5/2003 | Rollock |
| 2003/0162146 A1 | 8/2003 | Shortt et al. |
| 2003/0204155 A1 | 10/2003 | Egeresi |
| 2003/0213075 A1 | 11/2003 | Hui et al. |
| 2004/0045107 A1 | 3/2004 | Egeresi |
| 2004/0076921 A1 | 4/2004 | Gofman et al. |
| 2004/0122377 A1 | 6/2004 | Fischer et al. |
| 2004/0126730 A1 | 7/2004 | Panagotacos |
| 2004/0180569 A1 | 10/2004 | Chiou |
| 2004/0209222 A1 | 10/2004 | Snyder et al. |
| 2005/0004498 A1 | 1/2005 | Klupt |
| 2005/0049620 A1 | 3/2005 | Chang |
| 2005/0064371 A1 | 3/2005 | Soukos et al. |
| 2005/0101894 A1 | 5/2005 | Hippensteel |
| 2005/0102773 A1 | 5/2005 | Obermann et al. |
| 2005/0144745 A1 | 7/2005 | Russell |
| 2005/0177079 A1 | 8/2005 | Pan |
| 2005/0271531 A1 | 12/2005 | Brown et al. |
| 2006/0010624 A1 | 1/2006 | Cleland |
| 2006/0021165 A1 | 2/2006 | Boland et al. |
| 2006/0026784 A1 | 2/2006 | Moskovich et al. |
| 2006/0057539 A1 | 3/2006 | Sodo |
| 2006/0078844 A1 | 4/2006 | Goldman et al. |
| 2006/0079818 A1 | 4/2006 | Yande |
| 2006/0207052 A1 | 9/2006 | Tran |
| 2007/0082316 A1 | 4/2007 | Zhadanov et al. |
| 2007/0082317 A1 | 4/2007 | Chuang |
| 2007/0113360 A1 | 5/2007 | Tsai |
| 2007/0202459 A1 | 8/2007 | Boyd et al. |
| 2007/0203439 A1* | 8/2007 | Boyd ............ F04B 49/24 601/162 |
| 2007/0254260 A1 | 11/2007 | Alden |
| 2008/0008979 A1 | 1/2008 | Thomas et al. |
| 2008/0189951 A1 | 8/2008 | Molema et al. |
| 2008/0213719 A1 | 9/2008 | Giniger et al. |
| 2008/0253906 A1 | 10/2008 | Strong |
| 2008/0307591 A1 | 12/2008 | Farrell et al. |
| 2009/0070949 A1 | 3/2009 | Sagel et al. |
| 2009/0071267 A1 | 3/2009 | Mathus et al. |
| 2009/0082706 A1 | 3/2009 | Shaw |
| 2009/0084765 A1* | 4/2009 | Muratsubaki ........ B23K 26/146 219/121.67 |
| 2009/0124945 A1 | 5/2009 | Reich et al. |
| 2009/0128921 A1* | 5/2009 | Roth ................ G02B 19/0028 359/641 |
| 2009/0139351 A1 | 6/2009 | Reichmuth |
| 2009/0163839 A1 | 6/2009 | Alexander |
| 2009/0188780 A1 | 7/2009 | Watanabe |
| 2009/0236424 A1 | 9/2009 | Hennick et al. |
| 2009/0281454 A1 | 11/2009 | Baker et al. |
| 2010/0010524 A1 | 1/2010 | Barrington |
| 2010/0015566 A1 | 1/2010 | Shaw |
| 2010/0049177 A1 | 2/2010 | Boone et al. |
| 2010/0190132 A1 | 7/2010 | Taylor et al. |
| 2010/0209870 A1 | 8/2010 | Thomas et al. |
| 2010/0239998 A1 | 9/2010 | Snyder et al. |
| 2010/0261134 A1 | 10/2010 | Boyd et al. |
| 2010/0261137 A1 | 10/2010 | Boyd et al. |
| 2010/0266980 A1 | 10/2010 | Boyd et al. |
| 2010/0326536 A1 | 12/2010 | Nan |
| 2010/0330527 A1 | 12/2010 | Boyd et al. |
| 2011/0027749 A1 | 2/2011 | Syed |
| 2011/0076090 A1 | 3/2011 | Wu et al. |
| 2011/0097683 A1 | 4/2011 | Boyd et al. |
| 2011/0139826 A1 | 6/2011 | Hair et al. |
| 2011/0144588 A1 | 6/2011 | Taylor et al. |
| 2011/0184341 A1 | 7/2011 | Baker et al. |
| 2011/0307039 A1 | 12/2011 | Cornell |
| 2012/0021374 A1 | 1/2012 | Cacka et al. |
| 2012/0045730 A1 | 2/2012 | Snyder et al. |
| 2012/0064480 A1 | 3/2012 | Hegemann |
| 2012/0077145 A1 | 3/2012 | Tsurukawa |
| 2012/0141952 A1 | 6/2012 | Snyder et al. |
| 2012/0179118 A1 | 7/2012 | Hair |
| 2012/0189976 A1 | 7/2012 | McDonough et al. |
| 2012/0277663 A1 | 11/2012 | Millman et al. |
| 2012/0277677 A1 | 11/2012 | Taylor et al. |
| 2012/0277678 A1 | 11/2012 | Taylor et al. |
| 2012/0279002 A1 | 11/2012 | Sokol et al. |
| 2012/0295220 A1 | 11/2012 | Thomas et al. |
| 2013/0089832 A1 | 4/2013 | Lee |
| 2014/0106296 A1 | 4/2014 | Woodard et al. |
| 2014/0193774 A1 | 7/2014 | Snyder et al. |
| 2014/0259474 A1 | 9/2014 | Sokol et al. |
| 2014/0272782 A1 | 9/2014 | Luettgen et al. |
| 2014/0352088 A1 | 12/2014 | Wu |
| 2015/0147717 A1 | 5/2015 | Taylor et al. |
| 2015/0173850 A1 | 6/2015 | Garrigues et al. |
| 2016/0151133 A1 | 6/2016 | Luettgen et al. |
| 2017/0239132 A1 | 8/2017 | Luettgen et al. |

FOREIGN PATENT DOCUMENTS

| | | | |
|---|---|---|---|
| CH | 655237 | 4/1987 | |
| CN | 204049908 | 12/2014 | |
| DE | 1466963 | 5/1969 | |
| DE | 1566490 | 11/1970 | |
| DE | 2019003 | 11/1971 | |
| DE | 2409752 | 9/1975 | |
| DE | 2545936 | 4/1977 | |
| DE | 2714876 | 10/1978 | |
| DE | 2910982 | 2/1980 | |
| DE | 3346651 | 7/1985 | |
| EP | 0023672 | 7/1980 | |
| EP | 0515983 | 2/1992 | |
| EP | 1825827 | 8/2007 | |
| FR | 2556954 | 6/1985 | |
| FR | 2654627 | 5/1991 | |
| GB | 838564 | 6/1960 | |
| GB | 1182031 | 2/1970 | |
| GB | 2018605 | 10/1979 | |
| GB | 2237505 | 5/1991 | |
| JP | 2-134150 | 4/1990 | |
| JP | 2003290368 A * | 10/2003 | ............ A51N 5/06 |
| JP | 2009-39455 | 2/2009 | |
| KR | 20120126265 | 11/2012 | |
| WO | WO95/016404 | 6/1995 | |
| WO | WO01/10327 | 2/2001 | |
| WO | WO01/19281 | 3/2001 | |
| WO | WO04/021958 | 3/2004 | |
| WO | WO04/039205 | 5/2004 | |
| WO | WO2004/060259 | 7/2004 | |
| WO | WO2004/062518 | 7/2004 | |
| WO | WO2008/070730 | 6/2008 | |
| WO | WO2008/157585 | 12/2008 | |
| WO | WO2013/095462 | 6/2013 | |
| WO | WO2013/124691 | 8/2013 | |
| WO | WO2014/145890 | 9/2014 | |

OTHER PUBLICATIONS

The Right Tool, Electron Fusion Devices, Inc., 2 pages, at least as early as Feb. 1991.
Japanese Packaging, 2 pages, at least as early as Dec. 2002.
Japanese Instruction Brochure, 2 pages, at least as early as Dec. 2002.

(56) References Cited

OTHER PUBLICATIONS

Brochure: Woog International, "You have a 98% chance of getting gum disease. Unless you read this.", Lancaster, Pennsylvania, Feb. 1987.

Brochure: Woog International, "We put the control of home dental care back into the hands of the professional", Lancaster, Pennsylvania, Feb. 1987.

Brochure: WOOG International, "Products at a Glance: Home Dental Care System" WOOG ORAJET, at least as early as Dec. 18, 1998.

Website: http://www.just4teeth.com/product/Panasonic/Panasonic_Portable_Irrigator.htm, 2 pages, at least as early as Jun. 20, 2003.

Website: http://www.videodirectstore.com/store/merchant.mv?Screen=PROD&Product_Code=EW1'. . . , 2 pages, at least as early as Jun. 20, 2003.

Website: http://www.products.consumerguide.com/cp/family/review/index.dfm/id/18742, 2 pages, at least as early as Jun. 20, 2003.

Website: http://www.racekarteng.com/images/walbroparts.gif and http://www.muller.neUmullermachine/docs/walbro1.html, 4 pages, at least as early as Jun. 20, 2003.

International Search Report, Application No. PCT/US2010/028180, 2 pages, dated May 18, 2010.

International Search Report, PCT/US2011/052795, 10 pages, dated Jan. 17, 2012.

Waterpik SinuSense, Website: http://www.insightsbyapril.com/2012/03/waterpik-natural-remedy-for-sinus.html, retrieved on May 31, 2012.

Waterpik WP 350W Oral Irrigator. Dentist.net. Copyright date 2013. Date accessed: Mar. 30, 2017, 2 pages <http://www.dentalhoo.com/waterpik-wp350.asp>.

IPik Portable Oral Irrigator. AliExpress. Date reviewed: Oct. 5, 2016. <https://www.allexpress.com/...e-Oral-Care-Product-Nasal-Irrigator-Tooth-Flosser-Water/1525541997.html?aff_platform=aaf&cpt=1490913714609&sk=yfAeyJa&aff_trace_key=c5a300c4f02e46d08c042f5292e1762f-1490913714609-07517-yfAeyJa>, 18 pages.

Brite Leafs Professional Portable 2-in-1 Nasal Sinus & Oral Irrigator. Brite Leafs. Copyright date 2012, <http://www.briteleafs.com/product6.html> , 1 page.

AliExpress. Date reviewed: Jan. 12, 2017. <https://www.aliexpress.com/item/Cordless-Water-Floss-Portable-Oral-Irrigator-Dental-Water-Flosser-Waterpic-Whatpick-Dental-Water-Pic-Whater-Pick/32769416341.html?spm=2114.40010308.4.75.Owuzfj>.

Suvo. "Helical Gears vs Spur Gears—Advantages and Disadvantages Compared." Brighthub Engineering, Aug. 18, 2010, www.brighthubengineering.com/manufacturing-technology/33535-helical-gears-vs-spur-gears/., 7 pages.

Waterpik ADA Accepted WP-663, posted at amazon.com, earliest date reviewed on Feb. 6, 2014, [online], acquired on Feb. 12, 2018. Available from Internet, <URL: https://www.amazon.com/Waterpik-Accepted-WP-663-Aquarius-Flosser/dp/B072JFVXSY/ref=cm_cr_arp_d_product_top?ie=UTF8&th=1 > (Year: 2014).

Waterpik Classic Professional Water Flosser, WP-72, posted at amazon.com, earliest date reviewed on Mar. 5, 2016, [online], acquired on Feb. 23, 2018. Available from Internet, <URL: https://www.amazon.com/Waterpik-Classic-Professional-Flosser-WP-72/dp/B00HFQQOU6/ref=cm_cr_arp_d_product_top?ie=UTF8> (Year: 2016).

Waterpik Complete Care 5.0 Toothbrush, posted at amazon.com, earliest date reviewed on Mar. 14, 2016, [online], acquired on Feb. 23, 2018. Available from Internet, <URL: https://www.amazon.com/Waterpik-Complete-Toothbrush-Water-Flosser/dp/B01CRZ939Y/ref=cm_cr_arp_d_product_top?ie=UTF8> (Year: 2016).

\* cited by examiner

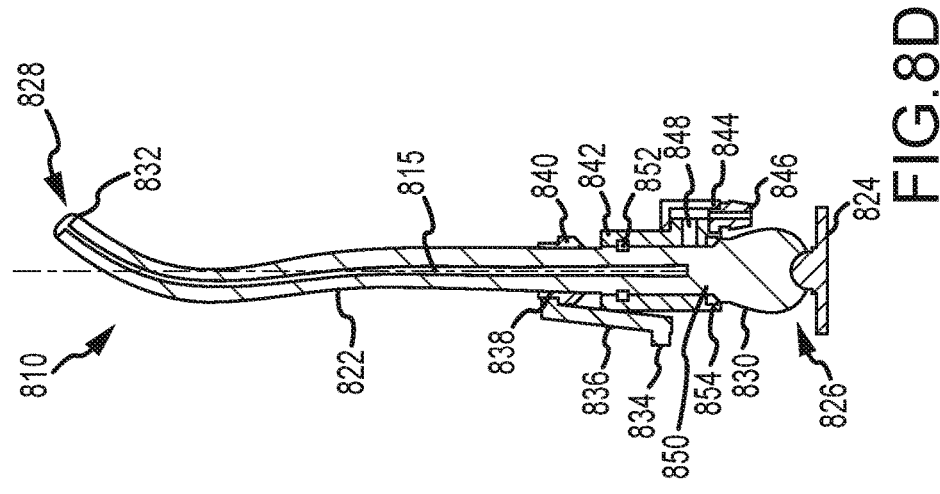
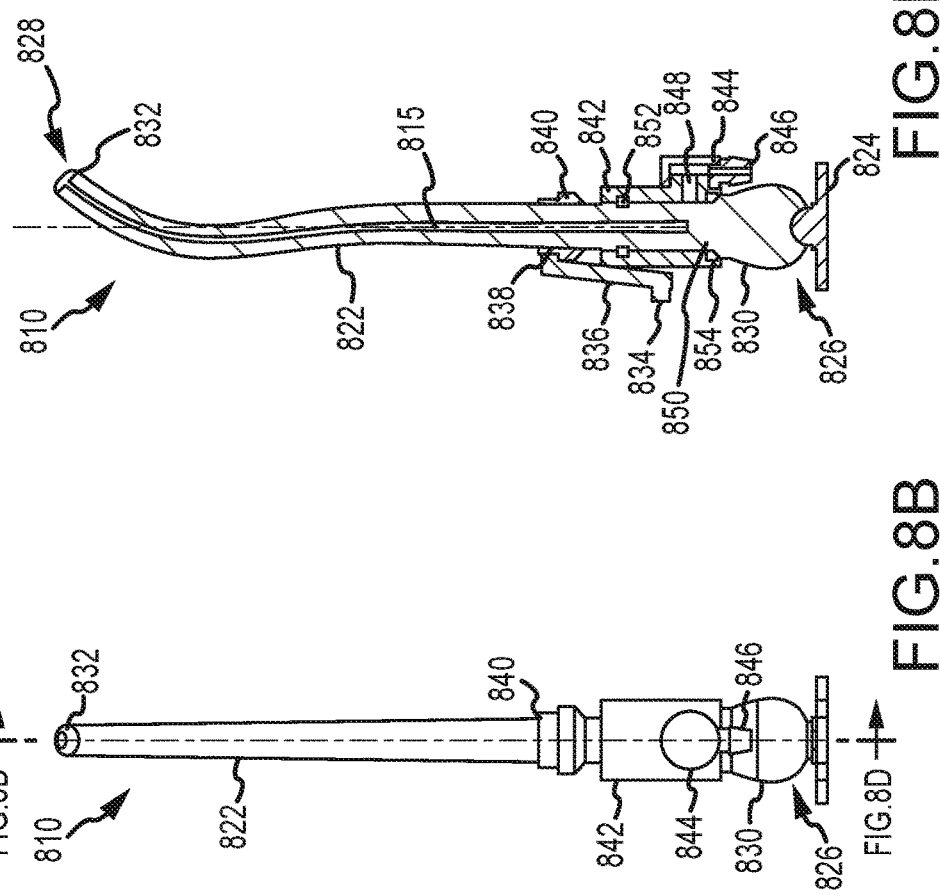
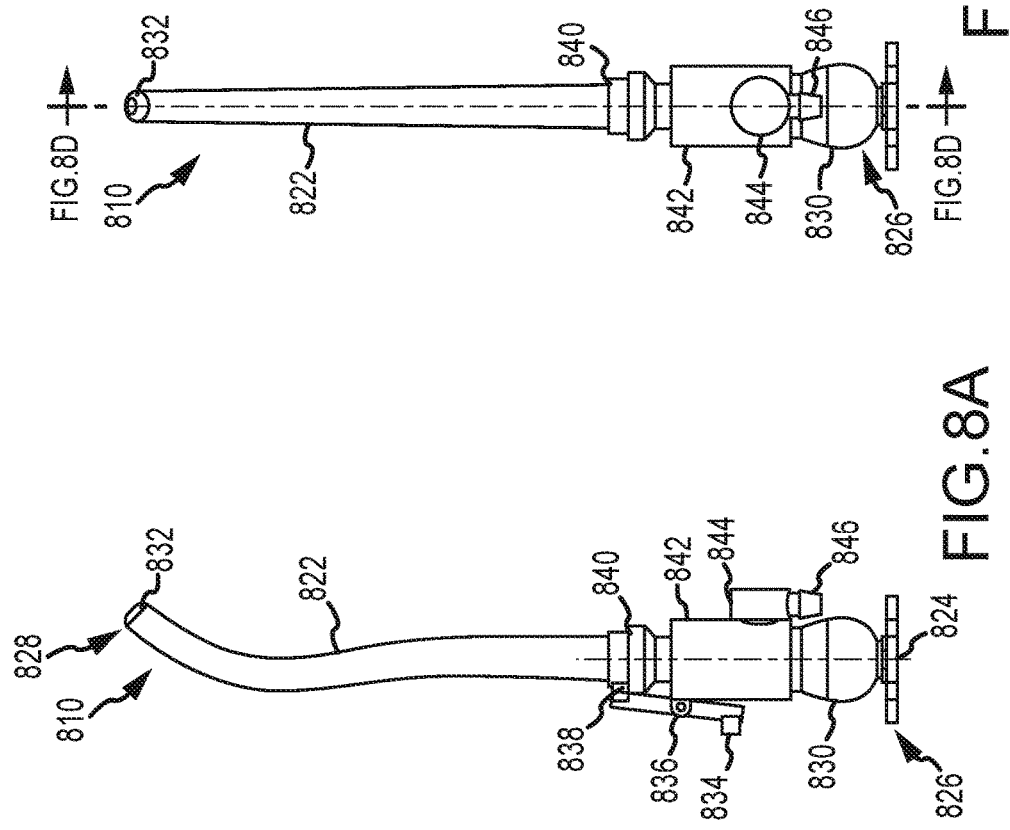
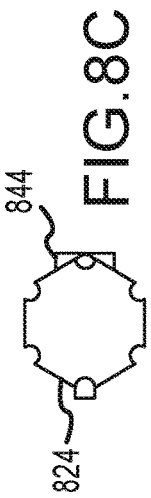

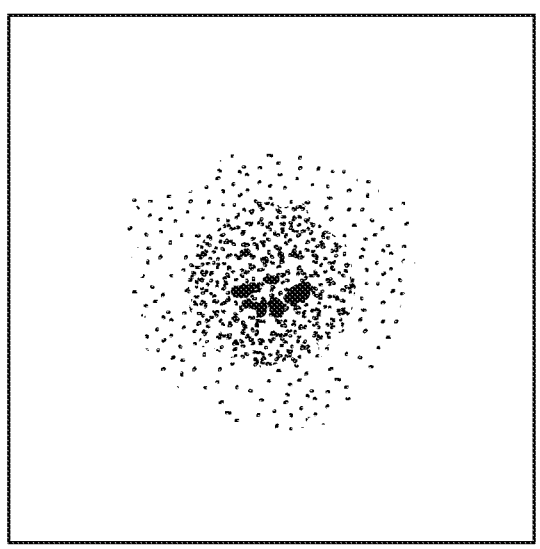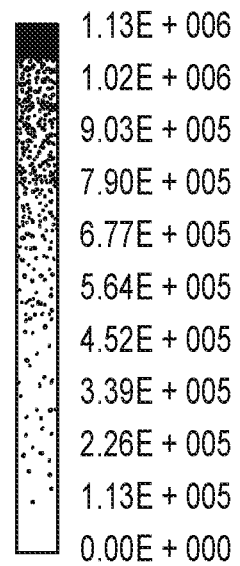
DETECTOR IMAGE: INCOHERENT IRRADIANCE
FRI DEC 19 2008
DETECTOR 7, NSCG SURFACE 1:
SIZE 30.000 W X 30.000 H MILLIMETERS, PIXELS 200 W X 200 H, TOTAL HITS = 440394
PEAK IRRADIANCE : 1.1290E + 006 WATTS/M^2
TOTAL POWER     : 5.5832E + 001 WATTS
FIG.9B

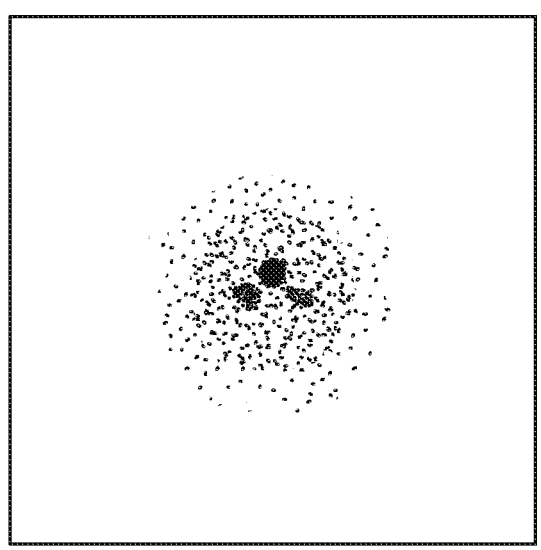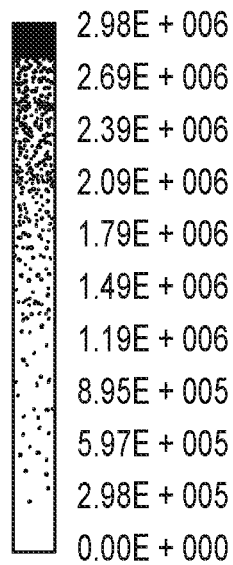
DETECTOR IMAGE: INCOHERENT IRRADIANCE
FRI DEC 19 2008
DETECTOR 7, NSCG SURFACE 1:
SIZE 30.000 W X 30.000 H MILLIMETERS, PIXELS 200 W X 200 H, TOTAL HITS = 478470
PEAK IRRADIANCE : 2.9839E + 006 WATTS/M^2
TOTAL POWER    : 5.6849E + 001 WATTS
FIG.10B

ORAL IRRIGATOR APPLIANCE WITH RADIANT ENERGY DELIVERY FOR BACTERICIDAL EFFECT

CROSS REFERENCE TO RELATED APPLICATIONS

This application is a continuation of U.S. application Ser. No. 13/238,243, filed 21 Sep. 2011 and titled "Oral Irrigator Appliance with Radiant Energy Delivery for Bactericidal Effect," which claims the benefit of priority pursuant to 35 U.S.C. § 119(e) of U.S. Provisional Patent Application No. 61/385,554, filed 22 Sep. 2010 and titled "Oral Irrigator Appliance with Radiant Energy Delivery for Bactericidal Effect," and which is also a continuation-in-part patent application of U.S. patent application Ser. No. 12/729,076, filed 22 Mar. 2010 and titled "Oral Irrigator Appliance with Radiant Energy Delivery for Bactericidal Effect," which claims the benefit of priority pursuant to 35 U.S.C. § 119(e) of U.S. Provisional Patent Application No. 61/162,126, filed 20 Mar. 2009 and titled "Oral Irrigator Appliance with Radiant Energy Delivery for Bactericidal Effect," the disclosures of all of which are hereby incorporated herein by reference in their entireties.

TECHNICAL FIELD

This technology relates to an oral irrigator, and more particularly to an oral irrigator including a radiant energy source to enhance the bacteria reducing effect.

BACKGROUND

An oral irrigator, also referred to as a dental water jet, includes generally a water reservoir supplying water to a pump, which in turn delivers water through a handle member having a tip structure, and into a user's mouth. The tip structure is sized and oriented to allow the user to direct the water stream against the user's teeth or gums as desired. The water stream may be continuous or pulsed. The reservoir of the oral irrigator may be positioned on a counter top, or may be hand held. Examples of such oral irrigators are described in U.S. Pat. Nos. 6,056,710 and 7,147,468 and U.S. Patent Application Publication No. 2008/0008979.

The effectiveness of existing oral irrigators is derived by the disruptive influence of the water stream on the bacteria found in the mouth. The bacteria is dislodged by the water stream and delivered out of the mouth (either swallowed or rinsed out).

The information included in this Background section of the specification, including any references cited herein and any description or discussion thereof, is included for technical reference purposes only and is not to be regarded subject matter by which the scope of the invention is to be bound.

SUMMARY

In one implementation, an oral irrigator for delivery radiant energy includes a base housing, a pump mechanism, a reservoir operably associated with the base housing and fluidically associated with the pump mechanism, a jet tip fluidically associated with the reservoir that directs a fluid at a surface inside an oral cavity; and a radiant energy source directing radiant energy at a surface inside an oral cavity. In one embodiment, the radiant energy source and the jet tip may be unitary to direct both the fluid and the radiant energy in generally the same direction. In another embodiment, the radiant energy source and the jet tip may be separate structures collocated on a single irrigation wand.

In an another implementation, the oral irrigator for delivering radiant energy may further include a radiant energy conduit that directs the radiant energy from the radiant energy source to the oral cavity. In one embodiment, the radiant energy conduit and a fluid conduit of the jet tip may be separate structures that together form the jet tip. In another embodiment, the radiant energy conduit and the fluid conduit may be unitary and form the jet tip to direct both the fluid and the radiant energy from the same terminal point in generally the same direction.

In a further implementation of an oral irrigator for delivering radiant energy, the radiant energy source and the jet tip may be separate structures or devices attached to the same base housing and able to be used individually.

In an alternate implementation, the oral irrigator may be a handheld device with the jet tip, the radiant energy source, and the reservoir in one body for easy maneuverability or use when traveling. The as in the previous implementations described, the radiant energy source may be separate from or unitary with the jet tip or the radiant energy may be directed from the radiant energy source through a radiant energy conduit that is either separate from or integral with a fluid conduit of the jet tip.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Other features, details, utilities, and advantages of the present invention will be apparent from the following more particular written description of various embodiments of the invention as further illustrated in the accompanying drawings and defined in the appended claims.

BRIEF DESCRIPTION OF THE DRAWINGS

FIG. 8A is a side elevation view of an implementation of an oral irrigator jet tip that forms an integral radiant energy conduit.

FIG. 8B is a front elevation view of the oral irrigator jet tip of FIG. 8A.

FIG. 8C is a bottom plan view of the oral irrigator jet tip of FIG. 8A.

FIG. 8D is a cross section of the oral irrigator jet tip of FIG. 8B taken along lines A-A.

FIG. 9B is a detector image of the incoherent irradiance levels graphed in FIG. 9A.

FIG. 10B is a detector image of the incoherent irradiance levels graphed in FIG. 10A.

DETAILED DESCRIPTION

The technology disclosed herein pertains generally to the enhancement of the effectiveness of the traditional oral irrigator. In particular, the impact of the water stream from the jet tip is enhanced by the addition of a radiant energy source that also works to reduce the bacteria in a user's mouth without also using chemical additives. The wavelength of radiant energy is selected to closely match the adsorption peaks of certain black-pigmented oral bacteria. The radiant energy source may be located in any number of positions so long as it is directed at least partially into the user's oral cavity when the oral irrigator is used.

Figure 1A:
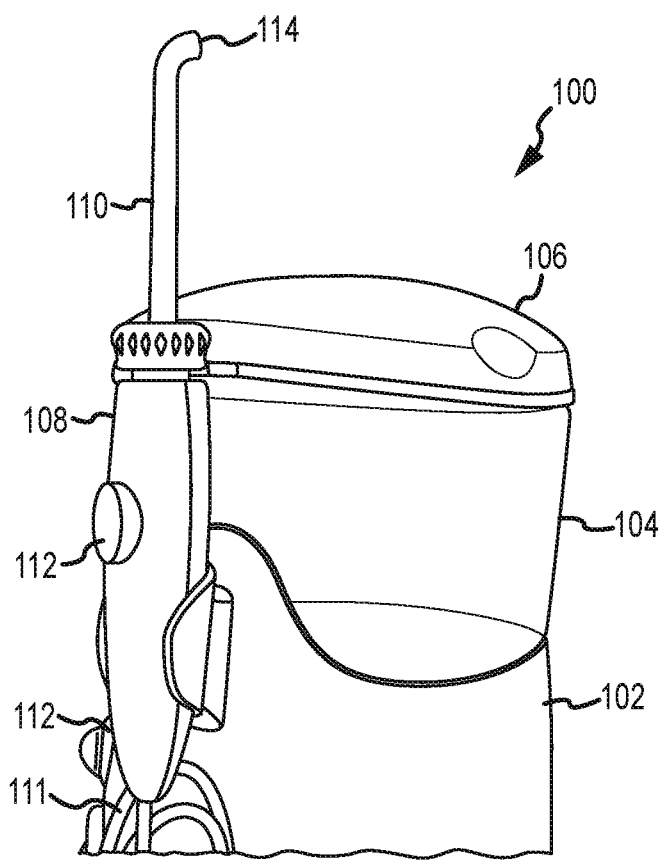
FIG. 1A is an isometric view of an implementation of an oral irrigator including a jet tip emitting radiant energy.
Figure 1B:
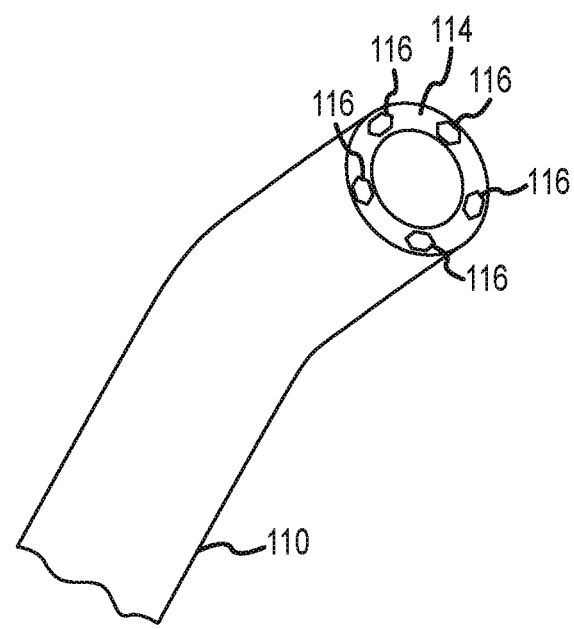
FIG. 1B is an enlarged view of a terminal end of the jet tip of the oral irrigator shown in FIG. 1A.

FIGS. 1A and 1B depict an implementation of an oral irrigator with a radiant energy delivery system 100. An oral irrigator 100 is shown having a base housing 102, which incorporates the pump powered by line voltage. A reservoir 104 having a lid sits atop the base housing 102 and serves to supply the water to the jet tip 110. The reservoir 104 is fluidically connected to the pump in order to pump water through a water line 111 to the jet handle 108. The jet tip 110 is fluidically connected to the jet handle 108 so that the pumped water flows through the jet tip 110. The jet tip 110 has a terminal end 114 that is positioned so as to cause the water stream to enter the oral cavity and flush bacteria therefrom.

The radiant energy, in this instance is in the form of a light emitting diode (LED) emitting light in the 350 to 450 nanometer range, preferably in the 375-415 nm range, and even more preferably in the 405-415 nm range, is configured relative to the terminal end 114 of the jet tip 110 so the radiant energy is generally directed in at least a similar direction as the water stream. However, in other embodiments the radiant energy may be in the form of a diode, such as a laser diode.

As shown in the embodiment of FIG. 1B, the radiant energy is created by five surface-mount LEDs 116 positioned around the terminal end 114 of the jet tip. Each of the surface-mount LEDs 116 are electrically connected to a power source, typically the same as the one that powers the pump in the base housing 102. In one embodiment, the electrical connections are wires extending from each LED 116 to a common wire, which then extends down the jet tip 110, along the handle 108, along the water line 111 to the base housing 102. In another embodiment, the common wire may be embedded in a sidewall of the jet tip 110 and further in a sidewall of the water line 111. In other embodiments, the LEDs 116 may be connected in series.

Controls 112 may be positioned on the handle 108 and/or base housing 102 to control the pressure and other characteristics of the water stream, as well as characteristics of the LEDs 116 (or other radiant energy sources) for example, activation, deactivation, intensity level, and activation time, among other options.

Figure 2A:
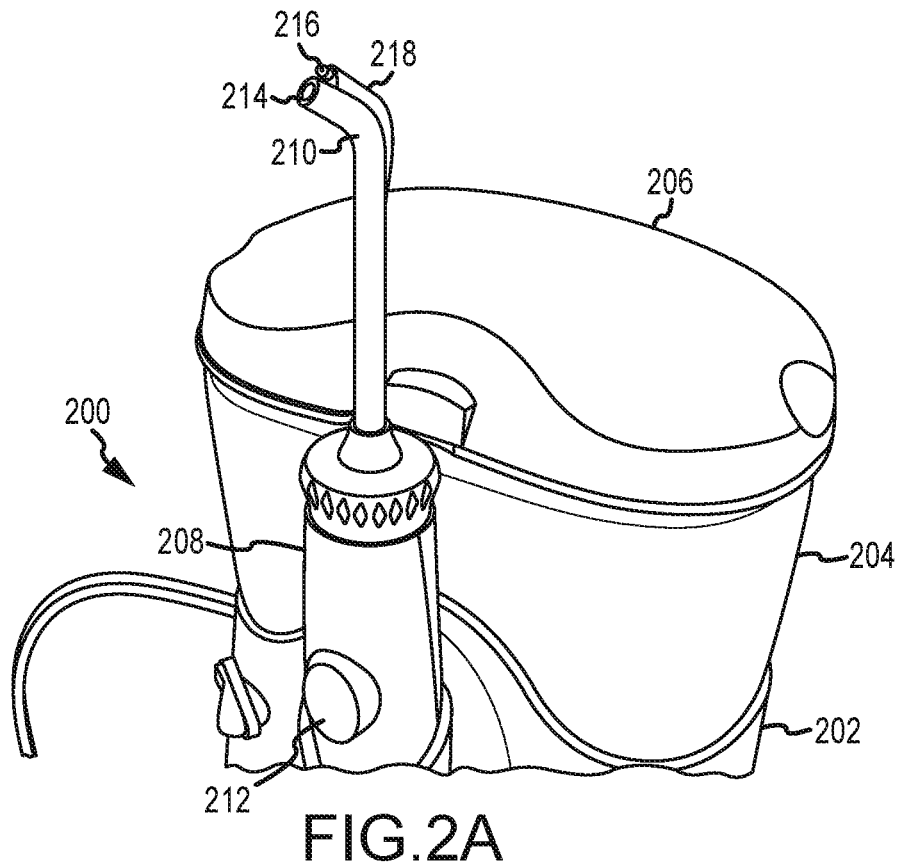
FIG. 2A is an isometric view of an alternate implementation of an oral irrigator including a jet tip for emitting radiant energy.
Figure 2B:
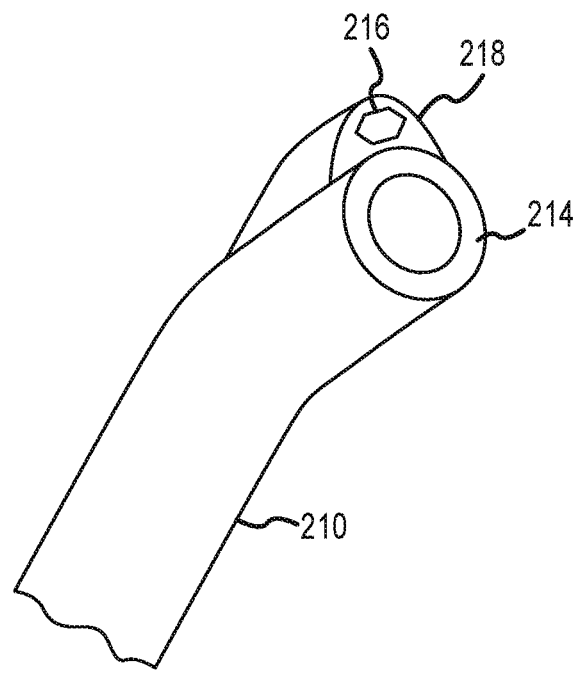
FIG. 2B is an enlarged view of the terminal end of the jet tip of the oral irrigator shown in FIG. 2A.

FIGS. 2A and 2B depict an alternative implementation of an oral irrigator 200 with a radiant energy delivery system. As in the prior figures, the oral irrigator 200 is composed of a base housing 202, a fluid reservoir 204, a lid 206, a handle 208, a jet tip 210, and one or more controls or actuators 212. In this implementation a single LED 216 is attached to one side of the terminal end 214 of the jet tip 210. The LED 216 is mounted on a shoulder 218 formed on the terminal end 214 of the jet tip 210. This design makes the terminal end 214 of the jet tip 210 a slightly larger in one dimension compared to a standard jet tip. The LED 216 is energized by lead wires contained or enveloped within the wall of jet tip 210. In other embodiments, the LED 216 may be a surface mount configuration that connects with a receptacle formed in the shoulder 218 or otherwise on the terminal end 214 of the jet tip 210.

Figure 3:
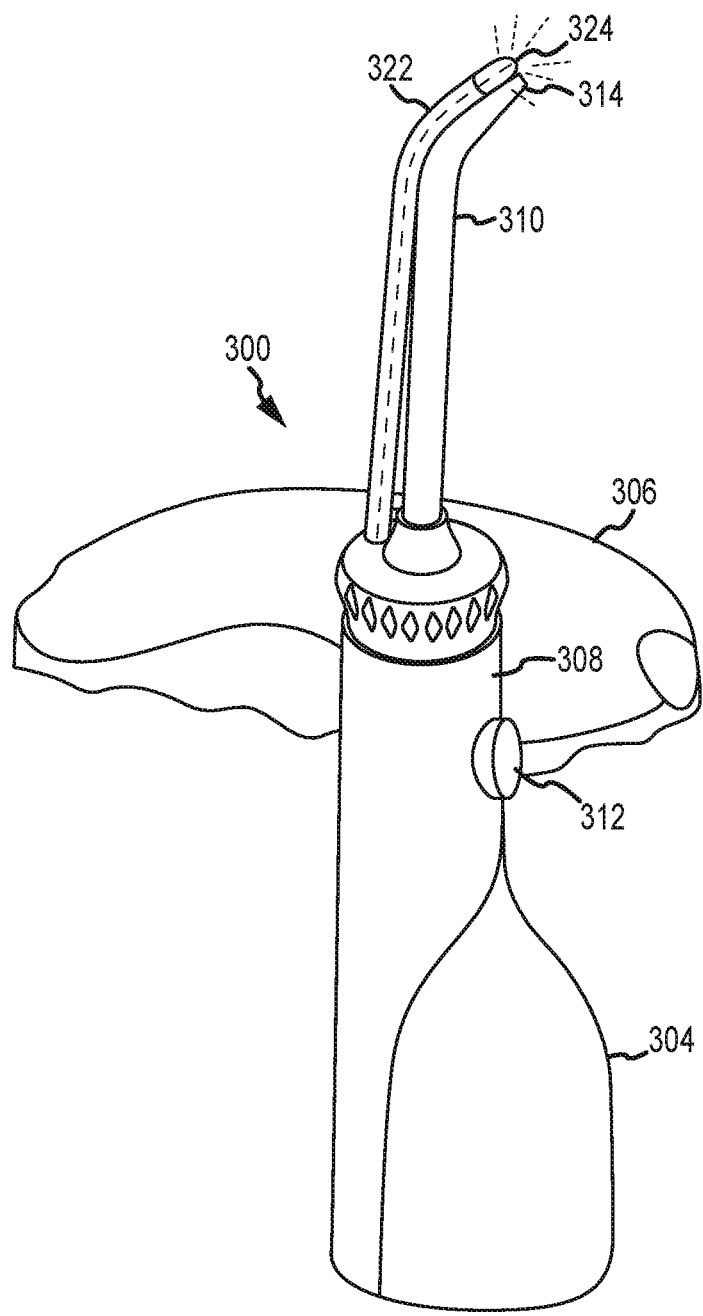
FIG. 3 is an enlarged, fragmentary, isometric view of a jet tip of a further implementation of an oral irrigator, wherein the radiant energy source is in the handle and radiant energy is transmitted via a light tube to the terminal end of the jet tip.

In an alternative implementation as shown in FIG. 3, the radiant light source may be positioned remote from the terminal end 314 of the jet tip 310 and directed along the jet tip 310 for use. For example, as shown in FIG. 3, the radiant light source of the oral irrigator 300 is positioned on the handle 308 with the radiant energy transmitted to the terminal end 314 of the jet tip 310 by a radiant energy conduit 322, e.g., a light tube. The energy 322 may be terminated at a location 324 at or adjacent the terminal end 314 of the jet tip 310. Alternatively, the termination location 324 of the radiant energy conduit 322 at a length shorter or longer than the terminal end 314 of the jet tip 310. In the embodiment of FIG. 3, the oral irrigator 300' is a handheld configuration with the reservoir 304' mounted to the handle 308'. The radiant energy source may be mounted in the handle 308' and powered by the portable power supply (e.g., a rechargeable battery) contained within the handle 308'. In this example, the handle 308' acts as a base, and includes a water pump mechanism and a control switch. The power source powers the pump mechanism and the radiant energy source. The control switch controls the power to the pump mechanism and/or the radiant energy source to actuate or deactivate the respective function. These functions may also be controlled by separate control switches.

In various implementations, the radiant energy conduit 322 may be a light tube made of glass or plastic and may also include or be formed of optical fibers. In one embodiment, the light tube may be formed of poly(methyl methacrylate) (PMMA). In another embodiment, the light tube may be formed as a glass or plastic fiber-optic light injector. The embodiments of FIGS. 3A and 3B allow the light source to be positioned remote from the terminal end 314 of the jet tip 310 to allow an LED, laser diode or other energy source to be used and to reduce exposure of the light source to moisture and physical impact with the user's oral cavity or other objects.

The radiant energy conduit 322 may also be aimed to cast the radiant energy in the same direction as the jet tip 310 to converge at the same location as the water stream exiting the jet tip 310, or the radiant energy may be directed generally in the same direction or in a different direction if desired. The radiant energy conduit 322 may also be selectively positionable to allow the user to adjust the position. The radiant energy may be directed or focused to shine in the same area of impact of the water jet in order to take advantage of the water jet lifting away the gum from the tooth and allowing the radiant energy to reach bacteria below the gum line.

FIGS. 4A-4D depict another implementation of an oral irrigator 400 in which a water jet handle 408 operates to provide a water stream 418, while a separate delivery wand 420 operates to provide the application of radiant light through a radiant energy conduit 422. The base 402 of the oral irrigator 400 supports a reservoir 404 covered by a lid 406 and a storage recess 407 for holding the handle 408 and the wand 420. The water jet handle 408 includes a jet tip 410 and a water line 411 communicating fluid from the pump to the jet tip 410 (as described above). Controls 412 on the base 402 and the water jet handle 408 allow some control of the characteristics of the water stream.

Figure 4A:
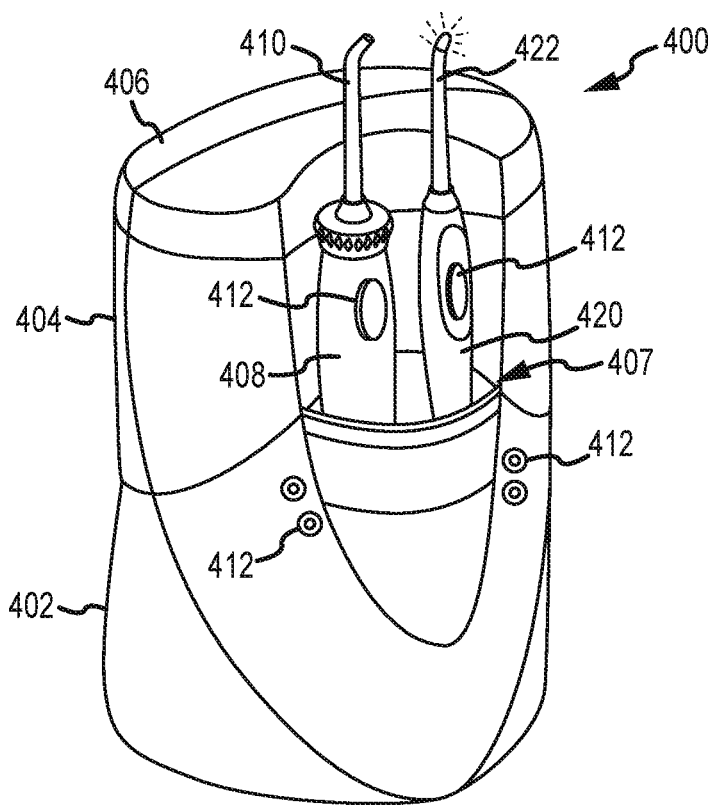
FIG. 4A is an isometric view of an implementation of an oral irrigator for emitting radiant energy including a jet handle and tip for fluid discharge and a separate handle for radiant energy application.
Figure 4B:
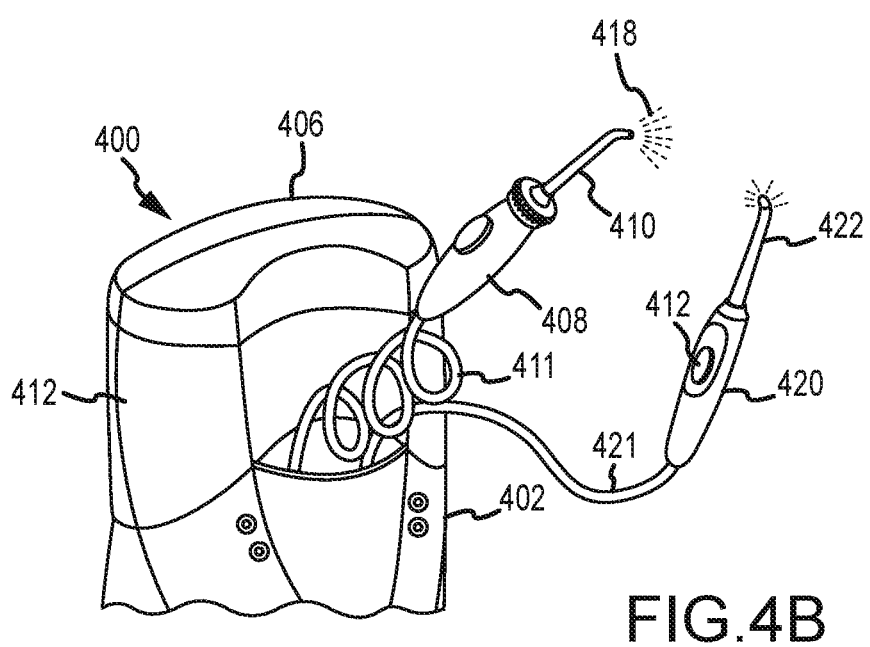
FIG. 4B is an isometric view depicting the oral irrigator of FIG. 4A with the jet handle and tip removed from the base housing and reservoir unit.

Still referring to FIGS. 4A-B, the radiant energy delivery wand 420 is provided for directing the radiant energy through the radiant energy conduit 422 into the user's oral cavity. The separate energy delivery wand 420 is connected to a power source at the base 402 by a power cord 421. In an alternate embodiment, the energy delivery wand 420 may be battery powered and not require a cord 421. The energy delivery wand 420 may include a switch 412 for controlling the status of the radiant energy, for example, activation and deactivation, and may also function to set the intensity level of the radiant energy.

The water jet handle 408 may be removed from the storage recess 407 in the base 402 and extended for use by the user to direct the water stream 418 into the user's mouth as depicted in FIG. 4C. The energy delivery wand 420 may similarly be removed from the storage recess 407 in the base 402 and extended for use by the user to direct the radiant energy through the radiant energy conduit 422 into the user's mouth as shown in FIG. 4D.

Figure 5A:
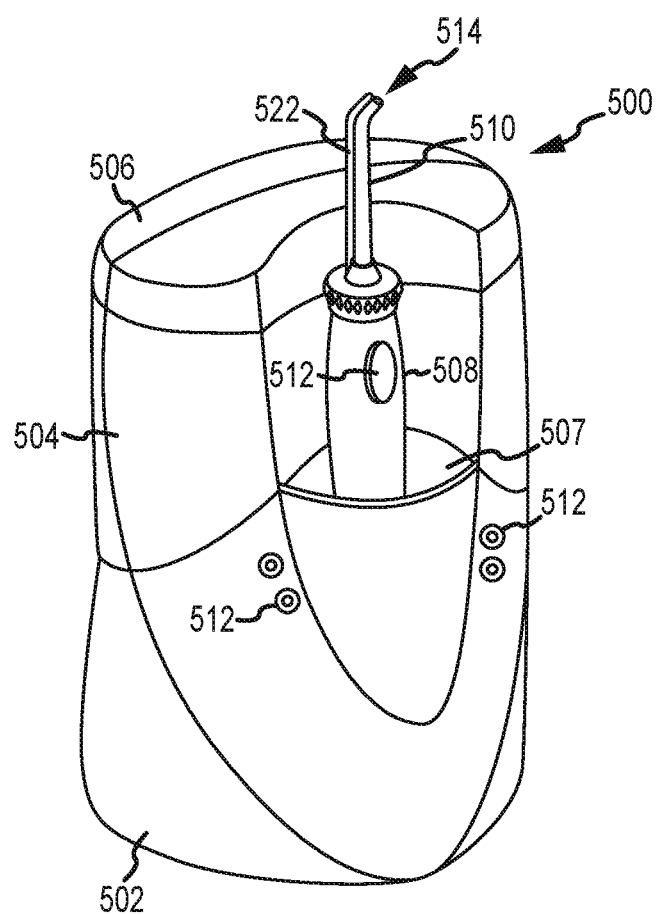
FIG. 5A is an isometric view of an implementation of an oral irrigator for emitting radiant energy with a single jet handle and tip includes both a fluid conduit for directing fluid and an additional radiant energy conduit for directing radiant energy from collocated terminal ends.
Figure 5C:
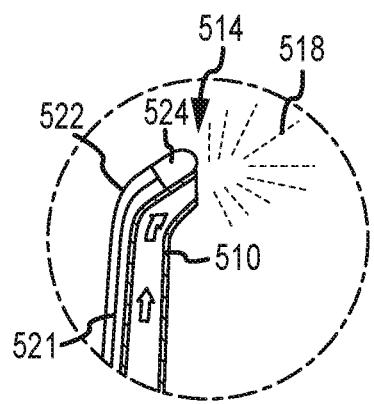
FIG. 5C is an enlarged partial view of the collocated radiant energy conduit tip and jet tip of FIG. 5A.
Figure 5B:
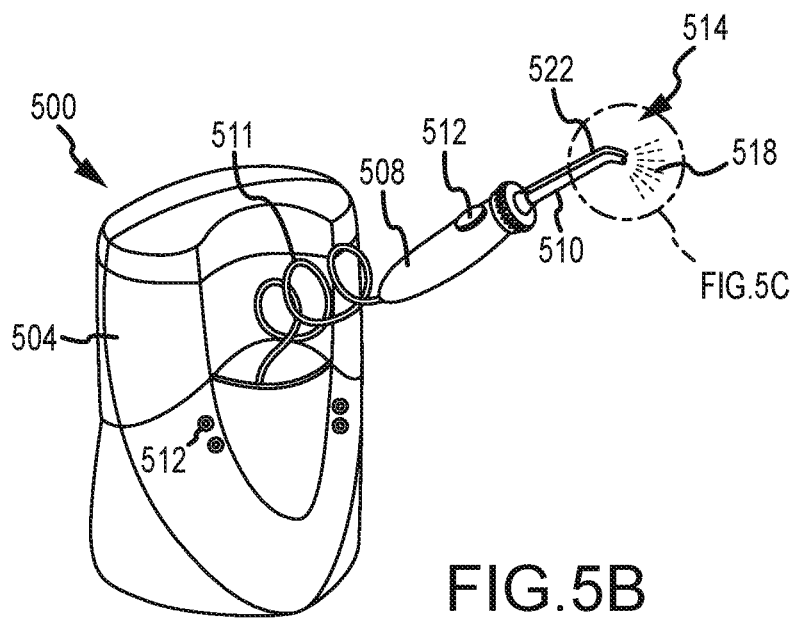
FIG. 5B is an isometric view depicting the oral irrigator of FIG. 5A with the jet handle and tip removed from the base housing and reservoir unit and the radiant energy conduit of the oral irrigator activated.

FIGS. 5A-5C depict another implementation of an oral irrigator 500. The oral irrigator 500 includes a base 502 for supporting a reservoir 504 having a lid 506 and a single jet handle 508. The jet handle 508 includes a jet tip 510 formed as a fluid conduit for directing a flow of water out of a terminal end 514 of the jet tip 510. The jet handle 508 also includes radiant energy source 524 positioned near the terminal end 514 of the jet tip 510. The radiant energy source 524 is positioned to direct light in at least generally the same direction of the terminal end 514 of the jet tip 510. In this example, the radiant energy source 524 is positioned at the end of a second conduit 522 running along the length of the water conduit 510. An electrical wire 521 runs along the second conduit 522, in this case within the interior cavity of the second conduit 522, to provide power to the radiant energy source 524 positioned at the tip of the second conduit 522 as best shown in FIG. 5C.

As shown in FIGS. 5-5C, the jet handle 508 includes a switch 512 to control the water flow through the first water conduit 510. The same switch 512 may also control the activation, deactivation, and intensity condition of the radiant energy source 524. Alternately, each may be controlled by a switch 512 positioned elsewhere on the unit, for example, on the base 502. The use of this oral irrigator device 500 may allow a user separate use of the water jet tip 510 and radiant energy source 524, or may allow the simultaneous use thereof.

In each of the above embodiments (as well as further embodiments below), the radiant energy sources may be suitably constructed to activate when the water flow is actuated, or may be controlled by sensors to actuate when positioned in a relatively dark space (such as the inside of a user's mouth), or may be controlled by a timer to help insure sufficient radiant energy is imparted to the bacteria in the user's mouth.

Figure 6A:
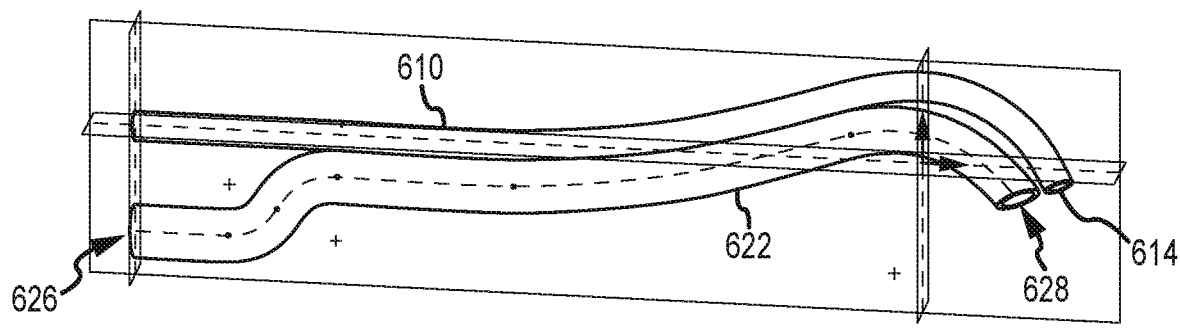
FIG. 6A is a schematic diagram of a collocated fluid conduit and radiant energy conduit for an oral irrigator jet tip.
Figure 6B:
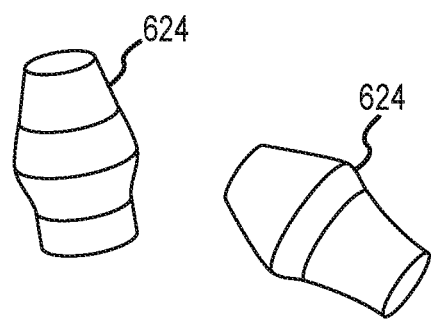
FIG. 6B is an isometric view of a molded lens system for focusing light energy into the radiant energy conduit of FIG. 6A.

FIG. 6A schematically depicts an alternate embodiment of a jet tip with a water conduit 610 separate from a corresponding radiant energy conduit 622. The water conduit 610 and the energy conduit 622 generally follow parallel paths and are mounted adjacent each other. The terminal end 614 of the water conduit 610 is at approximately the same distance from the handle as the distal end 628 of the energy conduit 622. In this embodiment, the energy conduit is a glass or plastic shaft or cylinder, or possibly a fiber optic light injector that transmits radiant energy from a light source at a proximal end 626 of the energy conduit 622 to the distal end 628 of the light conduit 622. FIG. 6B depicts two commonly available molded acrylic fiber light injectors 624 from Fraen Corporation.

In some embodiments, LEDs may be used as a source for the radiant energy. Exemplary LEDs may include, for example, Nichia 5POA (375 nm), Nichia 59013 (365 nm), or Xicon 351-3314-RC LEDs. In some implementations, suitable wavelengths for effective radiant energy have been found between 350-450 nm, preferably between 375-415 nm, even more preferably between 405-415 nm. In one exemplary implementation, a UV-1WS-L2 LED from Pro-light Opto Technology Corporation was used to provide light at desired wavelengths. Another way to characterize effective radiant energy is by intensity. The effective intensity required will depend on the species of microbe. Minimum effective intensities generally range from 2-50 J/cm.

The following tables present test results from the use of various LEDs and other light sources for varying amounts of time on various common types of bacteria that inhabit the oral cavity to determine the bactericidal effects. The Legend indicates the types of bacteria used in the experiments, the types of LEDs used, and an explanation of the meaning of the results. In the first experiment of Table 1, bacteria cultures were exposed to the light sources for periods of 2 minutes and 60 minutes. In the experiments of Tables 2, 3, and 4, bacteria cultures were exposed to the light sources for periods of 5 seconds, 30 seconds, 1 minute, 2 minutes, and 60 minutes. As indicated in the Legend, an IE or "Ineffective" entry means bacterial growth was observed in the culture without apparent inhibition, i.e., the incident light did not kill the bacteria. In contrast, an E or "Effective" entry indicates that while live bacteria remain in the culture, the bacteria were killed in the illuminated area.

Legend for Tables 1-4

NG = No growth on plate - invalid data point
IE = "Ineffective" - Bacterial growth on plate but no inhibition zones
E = "Effective" - Bacteria growth on plate but bacteria killed in area illuminated
Bacteria 1 *Porphyromonas Gingivalis* ATCC 33277
Bacteria 2 *Prevotella Intermedia* ATCC 25611
Bacteria 3 *Prevotella Nigrescens* ATCC 33563
Bacteria 4 *Prevotella Melaningena* ATCC 25845
led 1    Nichia 59013 - 365 nm
led 2    Mouser UV Xicon Led Lamps Taiwan PN-351-3314-RC
led 3    Blue - Sunbright 470 nm-ssp-lx6144A7uc
led 4    Nichia - 5poa-375 nm
led 5    White - Sunbright-ssp-lx6144A9UC
led 6    UV Florescent-JKL
led 7    FOX-uv
led 8    IR vcsel

TABLE 1

Bacteria 1

| Light Source | 2 min | 60 min |
|---|---|---|
| Control | IE | IE (poor) |
| Black Light | IE | |
| Germicidal | E | E |
| filter 1 | IE ? | |
| filter 2 | IE ? | |
| led 1 | IE ? | E |
| led 2 | IE ? | E |
| led 3 | IE ? | ? |
| led 4 | IE ? | ? |
| led 5 | IE | |
| led 6 | IE | |
| led 7 | IE | |
| led 8 | IE | |

TABLE 2

Bacteria 2

| Light Source | 5 sec | 30 sec | 60 sec | 2 min | 60 min |
|---|---|---|---|---|---|
| Control | IE | IE | IE | IE | IE |
| Black Light | | | | IE | E |
| Germicidal | E | E | E | E | E |
| filter 1 | | | | IE | E |
| filter 2 | | | | IE | E |
| led 1 | IE | E (partial) | IE | E | E |
| led 2 | IE | IE | IE | E | E |
| led 3 | IE | IE | IE | IE | E |
| led 4 | E | E | E | E | E |
| led 5 | | | | IE | E |
| led 6 | | | | IE | IE |
| led 7 | | | | IE | E |
| led 8 | | | | | |

TABLE 3

Bacteria 3

| Light Source | 5 sec | 30 sec | 60 sec | 2 min | 60 min |
|---|---|---|---|---|---|
| Control | IE | IE | IE | IE | IE |
| Black Light | | | | IE | E |
| Germicidal | E | E | E | E | E |
| filter 1 | | | | IE | E |
| filter 2 | | | | IE | E |
| led 1 | IE | IE | E | E | E |
| led 2 | IE | IE | IE | E | E |
| led 3 | IE | IE | IE | IE | E |
| led 4 | IE | E | E | E | E |
| led 5 | | | | IE | E |
| led 6 | | | | IE | IE |
| led 7 | | | | IE | E |
| led 8 | | | | IE | IE |

TABLE 4

Bacteria 4

| Light Source | 5 sec | 30 sec | 60 sec | 2 min | 60 min |
|---|---|---|---|---|---|
| Control | IE | IE | IE | IE | IE |
| Black Light | | | | IE | IE |
| Germicidal | E | E | E | E | E |
| filter 1 | | | | IE | IE |
| filter 2 | | | | IE | IE |
| led 1 | IE | IE | E (partial) | E | E |
| led 2 | IE | IE | IE | IE | E |
| led 3 | IE | IE | IE | E ? | E ? |
| led 4 | IE | E | E | E ? | E ? |
| led 5 | | | | IE | E |
| led 6 | | | | IE | IE |
| led 7 | | | | IE | IE |
| led 8 | | | | IE | IE |

In addition to the experimental testing above, another series of tests of radiant energy sources was performed to determine the effects of alternate energy sources. In the experiments of Tables 5, 6, 7, and 8, bacteria cultures were exposed to the light sources for periods of 5 seconds, 30 seconds, 1 minute, 2 minutes, and 60 minutes. As in the prior experiments, an IE or "Ineffective" entry means bacterial growth was observed in the culture without apparent inhibition. In contrast, an E or "Effective" entry indicates that while live bacteria remain in the culture, the bacteria were killed in the illuminated area.

TABLE 5

Light Effects on *Porphyromonas Gingivalis*

| Source (nm) | Configuration | Plate | Light # | 5 sec | 30 sec | 2 min | 5 min |
|---|---|---|---|---|---|---|---|
| 405 | 30E leaded | A | 1 | IE | IE | IE | IE |
| 420 | 15E leaded | A | 2 | IE | IE | IE | IE |
|  | (5) Nichia 590 a | A | 3 | IE | IE | IE | IE |
|  | (4) 0603 surface mount | A | 4 | IE | IE | IE | IE |
| 395 | L300 CUV Ledtronics | B | 1 | IE | IE | IE | IE |
| 395 | L120 CUV Ledtronics | B | 2 | IE | IE | IE | IE |
| 405 | SPL300CUV | B | 3 | IE | IE | IE | IE |
| 405 | L200CUV | B | 4 | IE | IE | IE | IE |
| 375 | Nichia into 2 mm fiber | C | 1 | IE | IE | IE | IE |
|  | broken into 1 mm | C | 2 | IE | IE | IE | IE |
|  | module 1 mm | C | 3 | IE | IE | IE | IE |
| 420 | 15E leaded | C | 4 | IE | IE | IE | IE |
| 375 | Nichia into 1 mm fiber | C | 5 | IE | IE | IE | IE |
| 408 | 18E into 1 mm | C | 6 | IE | IE | IE | IE |
| 375 | nichia into 1 mm | C | 7 | IE | IE | IE | IE |
| 394 | filtered sunlight | S | 1 | IE | IE | IE | IE |
| 400 | filtered sunlight | S | 2 | IE | IE | IE | IE |
| 405 | filtered sunlight | S | 3 | IE | IE | IE | IE |
| 410 | filtered sunlight | S | 4 | IE | IE | IE | IE |
| 415 | filtered sunlight | S | 5 | IE | IE | IE | IE |
| 254 | Sterilizing wand | W | 1 | IE | E | E | E |

TABLE 6

Light Effects on *Prevotella Intermedia*

| Source (nm) | Configuration | Plate | Light # | 5 sec | 30 sec | 2 min | 5 min |
|---|---|---|---|---|---|---|---|
| 405 | 30E leaded | A | 1 | IE | E | IE | E |
| 420 | 15E leaded | A | 2 | IE | IE | IE | IE |
|  | (5) Nichia 590 a | A | 3 | IE | IE | E | E |
|  | (4) 0603 surface mount | A | 4 | IE | IE | IE | IE |
| 395 | L300 CUV Ledtronics | B | 1 | IE | E | E | E |
| 395 | L120 CUV Ledtronics | B | 2 | IE | E | E | E |
| 405 | SPL300CUV | B | 3 | IE | E | E | E |
| 405 | L200CUV | B | 4 | IE | E | E | E |
| 375 | Nichia into 2 mm fiber | C | 1 | IE | IE | IE | IE |
|  | broken into 1 mm | C | 2 | IE | IE | IE | IE |
|  | module 1 mm | C | 3 | IE | IE | E | E |
| 420 | 15E leaded | C | 4 | IE | IE | IE | IE |
| 375 | Nichia into 1 mm fiber | C | 5 | IE | IE | IE | IE |
| 408 | 18E into 1 mm | C | 6 | IE | IE | IE | IE |
| 375 | nichia into 1 mm | C | 7 | IE | IE | IE | IE |
| 394 | filtered sunlight | S | 1 | IE | IE | IE | IE |
| 400 | filtered sunlight | S | 2 | IE | IE | IE | IE |
| 405 | filtered sunlight | S | 3 | IE | IE | IE | IE |
| 410 | filtered sunlight | S | 4 | IE | IE | IE | IE |
| 415 | filtered sunlight | S | 5 | IE | IE | IE | IE |
| 254 | Sterilizing wand | W | 1 | E | E | E | E |

TABLE 7

Light Effects on *Prevotella Nigrescens*

| Source (nm) | Configuration | Plate | Light # | 5 sec | 30 sec | 2 min | 5 min |
|---|---|---|---|---|---|---|---|
| 405 | 30E leaded | A | 1 | E | E | E | E |
| 420 | 15E leaded | A | 2 | IE | IE | IE | IE |
|  | (5) Nichia 590 a | A | 3 | E | E | E | E |
|  | (4) 0603 surface mount | A | 4 | IE | IE | E | E |
| 395 | L300 CUV Ledtronics | B | 1 | E | E | E | E |
| 395 | L120 CUV Ledtronics | B | 2 | E | E | E | E |
| 405 | SPL300CUV | B | 3 | E | E | E | E |
| 405 | L200CUV | B | 4 | E | E | E | E |
| 375 | Nichia into 2 mm fiber | C | 1 | IE | IE | E | E |
|  | broken into 1 mm | C | 2 | IE | IE | IE | IE |
|  | module 1 mm | C | 3 | E | E | E | E |
| 420 | 15E leaded | C | 4 | E | E | E | E |
| 375 | Nichia into 1 mm fiber | C | 5 | IE | IE | E | E |
| 408 | 18E into 1 mm | C | 6 | IE | IE | IE | IE |
| 375 | nichia into 1 mm | C | 7 | IE | IE | E | E |
| 394 | filtered sunlight | S | 1 | IE | IE | E | E |
| 400 | filtered sunlight | S | 2 | IE | IE | E | E |
| 405 | filtered sunlight | S | 3 | IE | IE | IE | E |
| 410 | filtered sunlight | S | 4 | IE | IE | IE | E |
| 415 | filtered sunlight | S | 5 | IE | IE | IE | E |
| 254 | Sterilizing wand | W | 1 | E | E | E | E |

TABLE 8

Light Effects on *Prevotella Melaningena*

| Source (nm) | Configuration | Plate | Light # | 5 sec | 30 sec | 2 min | 5 min |
|---|---|---|---|---|---|---|---|
| 405 | 30E leaded | A | 1 | IE | IE | E | E |
| 420 | 15E leaded | A | 2 | IE | IE | IE | IE |
|  | (5) Nichia 590 a | A | 3 | IE | E | E | E |
|  | (4) 0603 surface mount | A | 4 | IE | IE | IE | IE |
| 395 | L300 CUV Ledtronics | B | 1 | IE | IE | E | E |
| 395 | L120 CUV Ledtronics | B | 2 | IE | E | E | E |
| 405 | SPL300CUV | B | 3 | IE | IE | E | E |
| 405 | L200CUV | B | 4 | E | E | E | E |
| 375 | Nichia into 2 mm fiber | C | 1 | IE | IE | IE | IE |
|  | broken into 1 mm | C | 2 | IE | IE | IE | IE |
|  | module 1 mm | C | 3 | IE | IE | E S | E |
| 420 | 15E leaded | C | 4 | IE | IE | IE | IE |
| 375 | Nichia into 1 mm fiber | C | 5 | IE | IE | IE | IE |
| 408 | 18E into 1 mm | C | 6 | IE | IE | IE | IE |
| 375 | nichia into 1 mm | C | 7 | IE | IE | IE | IE |
| 394 | filtered sunlight | S | 1 | IE | IE | IE | IE |
| 400 | filtered sunlight | S | 2 | IE | IE | IE | IE |
| 405 | filtered sunlight | S | 3 | IE | IE | IE | IE |
| 410 | filtered sunlight | S | 4 | IE | IE | IE | IE |

TABLE 8-continued

Light Effects on *Prevotella Melaningena*

| Source (nm) | Configuration | Plate | Light # | 5 sec | 30 sec | 2 min | 5 min |
|---|---|---|---|---|---|---|---|
| 415 | filtered sunlight | S | 5 | IE | IE | IE | IE |
| 254 | Sterilizing wand | W | 1 | IE | E | E | E |

Figure 7:
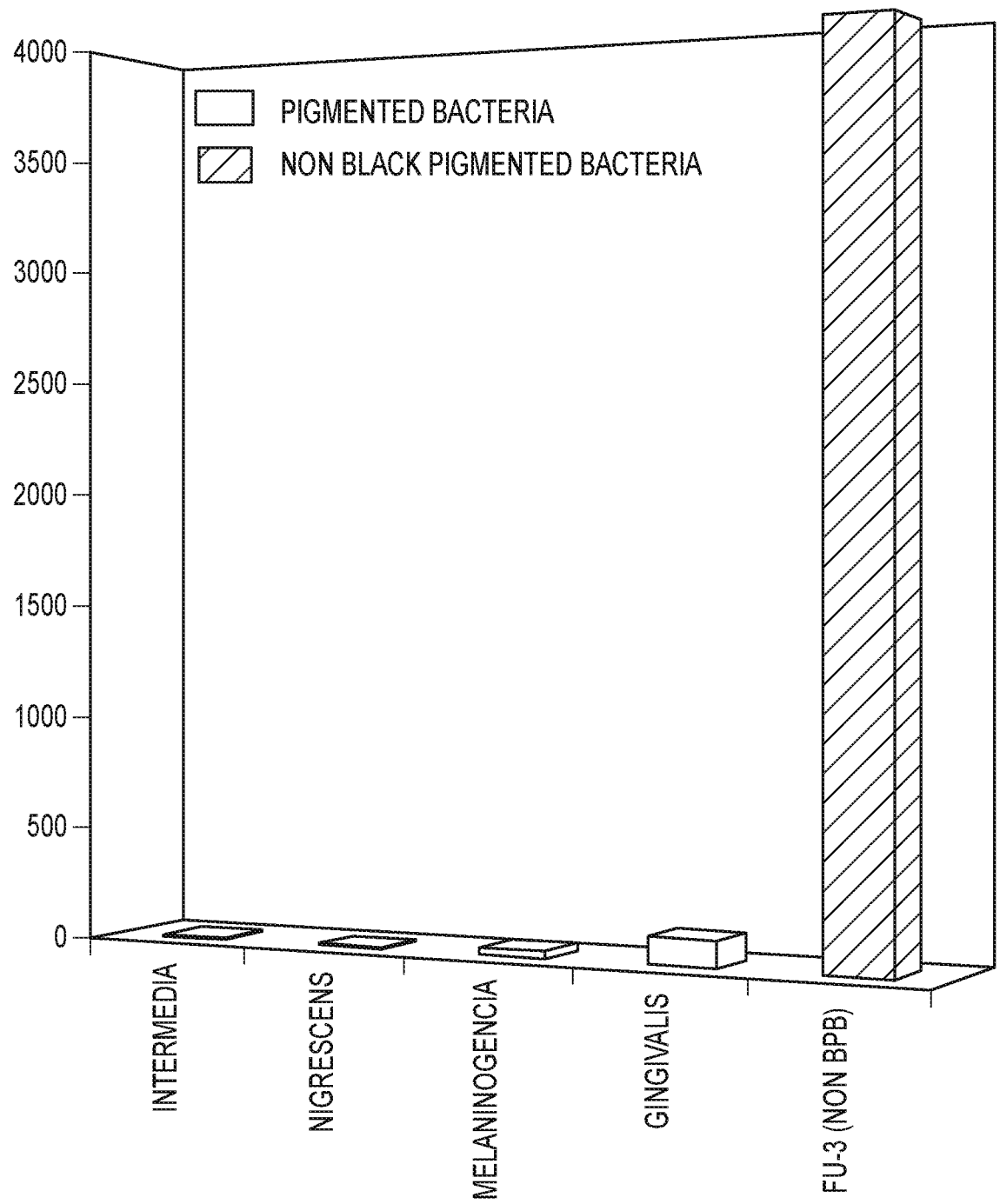
FIG. 7 is a bar graph depicting the effects of an implementation of an oral irrigator with a radiant energy delivery system on undesirable black pigmented bacteria as opposed to desirable non-black pigmented bacteria in a typical oral cavity.

These studies indicate that UV and near-UV light is effective in killing select periodontal pathogens. While shorter wavelength UV radiation is an extremely effective germicide, the mechanism of destruction in UV radiation below 300 nm is to destroy DNA in cells. (See, e.g., Soukos, N. S. et al., *Phototargeting oral black-pigmented bacteria*, Antimicrobial Agents and Chemotherapy, (April 2005) pp. 1391-96.) This mechanism is not selective and therefore the user's tissue cells could be destroyed as well. In contrast, by using higher wavelengths of light, e.g., between 350-450 nanometers, undesirable, black-pigmented bacteria can be destroyed without affecting the health of adjacent oral tissue. Wavelengths between 350-450 nm, and especially between 405-415 nm, are very effective bactericides by exciting endogenous porphyrins within the black-pigmented bacteria while leaving oral tissue unharmed. FIG. 7 is a bar graph showing the effectiveness of a 405 nm light source on black-pigmented bacteria compared to non-black-pigmented bacteria, which is actually healthy to have in the oral cavity. The undesirable black-pigmented bacteria are killed relatively quickly (in some cases under 5 seconds) while the desirable bacteria remains unharmed. This selective killing when used on a daily basis causes a beneficial, long-term shift in the ratio of desirable to undesirable bacteria as the desirable bacteria are allowed to grow and take the place previously occupied by the undesirable bacteria. This results in a lasting benefit to the user's oral health beyond what would be indicated by the one-time kill efficacy.

In embodiments using a light tube 622 as a radiant energy conduit as in FIG. 6A to direct the radiant energy from an energy source 624, the light tube 622 may be formed from plastic or glass fibers with a transmissive core and optionally a thin sheathing a material that has a lower refractive index, e.g., Mitsubishi Eska acrylic fibers sheathed with fluorine polymer, or similar glass fibers. Molded light tubes from acrylic polymers are common in many manufactured products. One example is the glowing speedometer needle of most modern automobiles. Fiber optic light injectors could also be used as light tubes. In another implementation, a molded light injector, e.g., as commercially produced by Fraen Corporation, may be used to direct light from an LED into an optical fiber or molded light tube.

Additional tests were performed to gauge the efficacy of various light sources on a number of common oral bacteria and other organisms commonly found in the oral cavity. Results of these tests are set forth below in Tables 9A-16B and are summarized in Table 17. In each table pair, the first table designated "A" shows the results of various exposures using a fiber optic radiant energy source. In the second tables of the pairs designated "B", results of various exposures using a radiant energy source mounted at the tip of the device are presented. In the tables, a "+" indicates no inhibition of the organism to the light source, a "W" indicates a weak inhibition of the organism to the light source, and a "-" indicates an inhibition of the organism to the light source.

Tables 9A-9B depict the results of exposure of *Porphyromonas gingivalis* ATCC 33277 (PG-1) to various light sources for periods of time between 5 seconds and 45 minutes (900 seconds). PG-1 is an anaerobic black pigmented bacteria associated with periodontal disease. In Table 9A, results of exposure to no light, and fiber optic sources of white light, FI Pro Light-2 mm, and AWP Pro Light-2 mm are depicted. PG-1 is one of the most resistant organisms, but testing shows first kills in some experiments within between 60 and 120 seconds of exposure. In Table 9B, results of exposure to tip mounted light sources at dominant wavelengths of 400 nm (two samples), 590 nm, and a surface mount white light are presented.

TABLE 9A

PG-1 with Fiber Optic Source

| Organism | Plate | Time | White light-3 mm | No Light | FI Pro Light-2 mm | AWP Pro Light-2 mm |
|---|---|---|---|---|---|---|
| PG-1 | A | 5 Sec | − | − | − | − |
| PG-1 | A | 15 Sec | − | − | − | − |
| PG-1 | A | 30 Sec | − | − | − | − |
| PG-1 | A | 60 Sec | − | − | − | − |
| PG-1 | A | 2 Min | + | − | − | W |
| PG-1 | A | 15 min | + | − | + | no data |
| PG-1 | A | 45 Min | + | − | + | no data |

TABLE 9B

PG-1 with Tip Mounted Source

| Organism | Plate | Time | 400 nm | 400 nm | 590 A | Surface mount |
|---|---|---|---|---|---|---|
| PG-1 | B | 5 Sec | − | − | − | − |
| PG-1 | B | 15 Sec | − | − | − | − |
| PG-1 | B | 30 Sec | − | − | − | − |
| PG-1 | B | 60 Sec | − | − | − | − |
| PG-1 | B | 2 Min | − | − | − | − |
| PG-1 | B | 15 min | + | − | − | + |
| PG-1 | B | 45 Min | + | + | + | + |

Tables 10A-10B depict the results of exposure of *Prevotella melaninogenica* ATCC 258465 (PM-2) to various light sources for periods of time between 5 seconds and 45 minutes (900 seconds). PM-2 is an anaerobic black pigmented bacteria associated with periodontal disease. In Table 10A, results of exposure to no light, and fiber optic sources of white light, FI Pro Light-2 mm, and AWP Pro Light-2 mm are depicted. In Table 10B, results of exposure to tip mounted light sources at dominant wavelengths of 400 nm (two samples), 590 nm, and a surface mount white light are presented.

TABLE 10A

PM-2 with Fiber Optic Source

| Organism | Plate | Time | White light-3 mm | No Light | FI Pro Light-2 mm | AWP Pro Light-2 mm |
|---|---|---|---|---|---|---|
| PM-2 | A | 5 Sec | − | − | − | − |
| PM-2 | A | 15 Sec | − | − | − | − |
| PM-2 | A | 30 Sec | − | − | + | W |
| PM-2 | A | 60 Sec | − | − | + | + |
| PM-2 | A | 2 Min | + | − | + | + |
| PM-2 | A | 15 min | + | − | + | no data |
| PM-2 | A | 45 Min | + | − | + | no data |

TABLE 10B

PM-2 with Tip Mounted Source

| Organism | Plate | Time | 400 nm | 400 nm | 590 A | Surface mount |
|---|---|---|---|---|---|---|
| PM-2 | B | 5 Sec | − | − | − | − |
| PM-2 | B | 15 Sec | W | − | − | − |
| PM-2 | B | 30 Sec | + | − | − | W |
| PM-2 | B | 60 Sec | + | W | − | + |
| PM-2 | B | 2 Min | + | + | − | + |
| PM-2 | B | 15 min | + | + | + | + |
| PM-2 | B | 45 Min | + | + | + | + |

Tables 11A-11B depict the results of exposure of *Porphyromonas intermedia* ATCC 25611 (PI-1) to various light sources for periods of time between 5 seconds and 45 minutes (900 seconds). PI-1 is an anaerobic black pigmented bacteria associated with periodontal disease. Comments in literature and the experimentation conducted herein suggests that PI-1 tends to be more susceptible to UV and less susceptible to antibiotics than *P. ginvivalis*. In Table 11A, results of exposure to no light, and fiber optic sources of white light, FI Pro Light-2 mm, and AWP Pro Light-2 mm are depicted. In Table 11B, results of exposure to tip mounted light sources at dominant wavelengths of 400 nm (two samples), 590 nm, and a surface mount white light are presented.

TABLE 11A

PI-1 with Fiber Optic Source

| Organism | Plate | Time | White light- 3 mm | No Light | FI Pro Light- 2 mm | AWP Pro Light- 2 mm |
|---|---|---|---|---|---|---|
| PI-1 | A | 5 Sec | + | − | + | + |
| PI-1 | A | 15 Sec | + | − | + | + |
| PI-1 | A | 30 Sec | + | − | + | + |
| PI-1 | A | 60 Sec | + | − | + | + |
| PI-1 | A | 2 Min | + | − | + | + |
| PI-1 | A | 15 min | + | − | + | + |
| PI-1 | A | 45 Min | + | − | + | + |

TABLE 11B

PI-1 with Tip Mounted Source

| Organism | Plate | Time | 400 nm | 400 nm | 590 A | Surface mount |
|---|---|---|---|---|---|---|
| PI-1 | B | 5 Sec | + | − | − | + |
| PI-1 | B | 15 Sec | + | + | + | + |
| PI-1 | B | 30 Sec | + | + | + | + |
| PI-1 | B | 60 Sec | + | + | + | + |
| PI-1 | B | 2 Min | + | + | + | + |
| PI-1 | B | 15 min | + | + | + | + |
| PI-1 | B | 45 Min | + | + | + | + |

Tables 12A-12B depict the results of exposure of *Porphyromonas nigrescens* ATCC 33563 (PN-1) to various light sources for periods of time between 5 seconds and 45 minutes (900 seconds). PN-1 is an anaerobic black pigmented bacteria associated with periodontal disease. Comments in literature and the experimentation conducted herein suggests that PN-1 tends to be more susceptible to UV and less susceptible to antibiotics than *P. ginvivalis*. In Table 12A, results of exposure to no light, and fiber optic sources of white light, FI Pro Light-2 mm, and AWP Pro Light-2 mm are depicted. In Table 12B, results of exposure to tip mounted light sources at dominant wavelengths of 400 nm (two samples), 590 nm, and a surface mount white light are presented.

TABLE 12A

PN-1 with Fiber Optic Source

| Organism | Plate | Time | White light- 3 mm | No Light | FI Pro Light- 2 mm | AWP Pro Light- 2 mm |
|---|---|---|---|---|---|---|
| PN-1 | A (BA) | 5 Sec | + | − | + | + |
| PN-1 | A (BA) | 15 Sec | + | − | + | + |
| PN-1 | A (BA) | 30 Sec | + | − | + | + |
| PN-1 | A (BA) | 60 Sec | + | − | + | + |
| PN-1 | A (BA) | 2 Min | + | − | + | + |
| PN-1 | A (BA) | 15 min | + | − | + | no data |
| PN-1 | A (BA) | 45 Min | + | − | + | no data |

TABLE 12B

PN-1 with Tip Mounted Source

| Organism | Plate | Time | 400 nm | 400 nm | 590 nm | Surface mount |
|---|---|---|---|---|---|---|
| PN-1 | B (BA) | 5 Sec | + | W | − | + |
| PN-1 | B (BA) | 15 Sec | + | + | W | + |
| PN-1 | B (BA) | 30 Sec | + | + | + | + |
| PN-1 | B (BA) | 60 Sec | + | + | + | + |
| PN-1 | B (BA) | 2 Min | + | + | + | + |
| PN-1 | B (BA) | 15 min | + | + | + | + |
| PN-1 | B (BA) | 45 Min | + | + | + | + |

Tables 13A-13B depict the results of exposure of *Streptococcus mutans* ATCC 25175 (STR-54) to various light sources for periods of time between 5 seconds and 45 minutes (900 seconds). STR-54 is a gram-positive, facultatively anaerobic bacteria commonly found in the human oral cavity. In Table 13A, results of exposure to no light, and fiber optic sources of white light, FI Pro Light-2 mm, and AWP Pro Light-2 mm are depicted. In Table 13B, results of exposure to tip mounted light sources at dominant wavelengths of 400 nm (two samples), 590 nm, and a surface mount white light are presented.

TABLE 13A

STR-54 with Fiber Optic Source

| Organism | Plate | Time | White light- 3 mm | No Light | FI Pro Light- 2 mm | AWP Pro Light- 2 mm |
|---|---|---|---|---|---|---|
| Str-54 | A (BA) | 5 Sec | − | − | − | − |
| Str-54 | A (BA) | 15 Sec | − | − | − | − |
| Str-54 | A (BA) | 30 Sec | − | − | − | − |
| Str-54 | A (BA) | 60 Sec | − | − | − | − |
| Str-54 | A (BA) | 2 Min | + | − | − | + |
| Str-54 | A (BA) | 15 min | + | − | W | no data |
| Str-54 | A (BA) | 45 Min | + | − | + | no data |

TABLE 13B

STR-54 with Tip Mounted Source

| Organism | Plate | Time | 400 nm | 400 nm | 590 A | Surface mount |
|---|---|---|---|---|---|---|
| Str-54 | B (BA) | 5 Sec | − | − | − | − |
| Str-54 | B (BA) | 15 Sec | − | − | − | − |
| Str-54 | B (BA) | 30 Sec | − | − | − | − |
| Str-54 | B (BA) | 60 Sec | − | − | − | − |
| Str-54 | B (BA) | 2 Min | W | − | − | − |

TABLE 13B-continued

STR-54 with Tip Mounted Source

| Organism | Plate | Time | 400 nm | 400 nm | 590 A | Surface mount |
|---|---|---|---|---|---|---|
| Str-54 | B (BA) | 15 min | W | – | W | – |
| Str-54 | B (BA) | 45 Min | + | – | W | W |

Tables 14A-14B depict the results of exposure of *Lactobacillus casei* ATCC 393 (LB-2) to various light sources for periods of time between 5 seconds and 45 minutes (900 seconds). LB-2 is a stain agent common in milk and dairy products and is associated with carries formation. In Table 14A, results of exposure to no light, and fiber optic sources of white light, FI Pro Light-2 mm, and AWP Pro Light-2 mm are depicted. In Table 14B, results of exposure to tip mounted light sources at dominant wavelengths of 400 nm (two samples), 590 nm, and a surface mount white light are presented.

TABLE 14A

LB-2 with Fiber Optic Source

| Organism | Plate | Time | White light-3 mm | No Light | FI Pro Light-2 mm | AWP Pro Light-2 mm |
|---|---|---|---|---|---|---|
| LB-2 | A (BA) | 5 Sec | – | – | – | – |
| LB-2 | A (BA) | 15 Sec | – | – | – | – |
| LB-2 | A (BA) | 30 Sec | – | – | – | – |
| LB-2 | A (BA) | 60 Sec | – | – | – | – |
| LB-2 | A (BA) | 2 Min | – | – | – | – |
| LB-2 | A (BA) | 15 min | – | – | – | – |
| LB-2 | A (BA) | 45 Min | + | – | + | no data |

TABLE 14B

LB-2 with Tip Mounted Source

| Organism | Plate | Time | 400 nm | 400 nm | 590 A | Surface mount |
|---|---|---|---|---|---|---|
| LB-2 | B (BA) | 5 Sec | – | – | – | – |
| LB-2 | B (BA) | 15 Sec | – | – | – | – |
| LB-2 | B (BA) | 30 Sec | – | – | – | – |
| LB-2 | B (BA) | 60 Sec | – | – | – | – |
| LB-2 | B (BA) | 2 Min | – | – | – | – |
| LB-2 | B (BA) | 15 min | – | – | – | – |
| LB-2 | B (BA) | 45 Min | + | – | – | – |

Tables 15A-15B depict the results of exposure of *Actinobacillus actinomycetemcomitans* ATCC 33384 (AA-1) to various light sources for periods of time between 5 seconds and 45 minutes (900 seconds). AA-1 is a bacteria associated with periodontal disease. In Table 15A, results of exposure to no light, and fiber optic sources of white light, FI Pro Light-2 mm, and AWP Pro Light-2 mm are depicted. In Table 15B, results of exposure to tip mounted light sources at dominant wavelengths of 400 nm (two samples), 590 nm, and a surface mount white light are presented.

TABLE 15A

AA-1 with Fiber Optic Source

| Organism | Plate | Time | White light-3 mm | No Light | FI Pro Light-2 mm | AWP Pro Light-2 mm |
|---|---|---|---|---|---|---|
| AA-1 | A (BA) | 5 Sec | – | – | – | – |
| AA-1 | A (BA) | 15 Sec | – | – | – | – |
| AA-1 | A (BA) | 30 Sec | – | – | – | – |
| AA-1 | A (BA) | 60 Sec | – | – | – | – |
| AA-1 | A (BA) | 2 Min | – | – | + | + |
| AA-1 | A (BA) | 15 min | + | – | + | no data |
| AA-1 | A (BA) | 45 Min | + | – | + | no data |

TABLE 15B

AA-1 with Tip Mounted Source

| Organism | Plate | Time | 400 nm | 400 nm | 590 A | Surface mount |
|---|---|---|---|---|---|---|
| AA-1 | B (BA) | 5 Sec | – | – | – | – |
| AA-1 | B (BA) | 15 Sec | – | – | – | – |
| AA-1 | B (BA) | 30 Sec | – | – | – | – |
| AA-1 | B (BA) | 60 Sec | – | – | – | – |
| AA-1 | B (BA) | 2 Min | W | – | – | – |
| AA-1 | B (BA) | 15 min | + | – | – | + |
| AA-1 | B (BA) | 45 Min | + | + | + | + |

Tables 16A-16B depict the results of exposure of *Fusobacterium nucleatum* ATCC (FU-3) to various light sources for periods of time between 5 seconds and 45 minutes (900 seconds). FU-3 is a key component of periodontal plaque due to its abundance and its ability to coaggregate with other species in the oral cavity. In Table 16A, results of exposure to no light, and fiber optic sources of white light, FI Pro Light-2 mm, and AWP Pro Light-2 mm are depicted. In Table 116B, results of exposure to tip mounted light sources at dominant wavelengths of 400 nm (two samples), 590 nm, and a surface mount white light are presented.

TABLE 16A

FU-3 with Fiber Optic Source

| Organism | Plate | Time | White light-3 mm | No light | FI Pro Light-2 mm | AWP Pro Light-2 mm |
|---|---|---|---|---|---|---|
| FU-3 | A (BA) | 5 Sec | – | – | – | – |
| FU-3 | A (BA) | 15 Sec | – | – | – | – |
| FU-3 | A (BA) | 30 Sec | – | – | – | – |
| FU-3 | A (BA) | 60 Sec | – | – | – | – |
| FU-3 | A (BA) | 2 Min | + | – | – | – |
| FU-3 | A (BA) | 15 min | + | – | + | no data |
| FU-3 | A (BA) | 45 Min | + | – | + | no data |

TABLE 16B

FU-3 With Tip Mounted Source

| Organism | Plate | Time | 400 nm | 400 nm | 590 A | Surface mount |
|---|---|---|---|---|---|---|
| FU-3 | B (BA) | 5 Sec | – | – | – | – |
| FU-3 | B (BA) | 15 Sec | – | – | – | – |
| FU-3 | B (BA) | 30 Sec | – | – | – | – |
| FU-3 | B (BA) | 60 Sec | – | – | – | – |
| FU-3 | B (BA) | 2 Min | + | – | – | – |
| FU-3 | B (BA) | 15 min | + | – | – | W |
| FU-3 | B (BA) | 45 Min | + | – | W | + |

Figure 20:
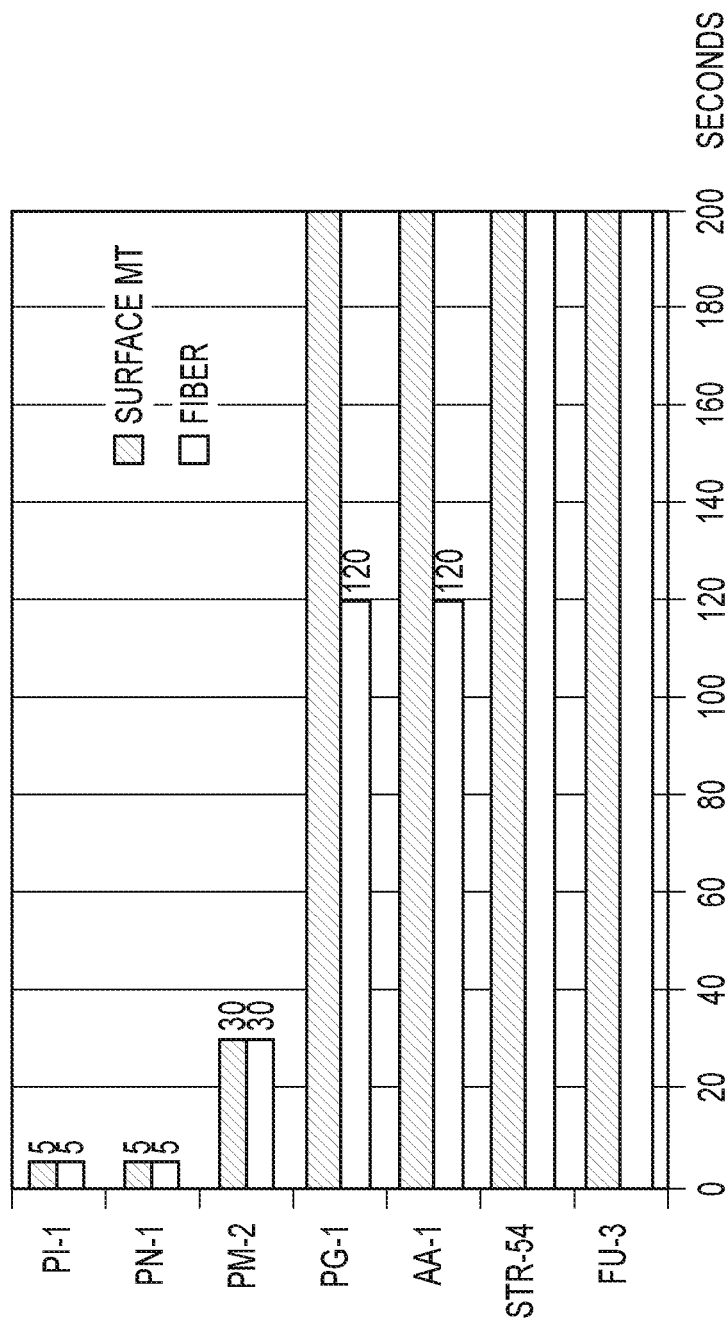
FIG. 20 is a graph summarizing the efficacy comparison of surface mount radiant energy sources to radiant energy provided by fiber optic delivery on the various organisms presented in Tables 9A-16B.

Table 17 presented as FIG. 20 depicts a graph summarizing the efficacy comparison of surface mount radiant energy sources to radiant energy provided by fiber optic delivery on the various organisms presented above in Tables 9A-16B.

In yet another implementation depicted in FIGS. 8A-8D, an integral jet tip 810 forms the water conduit 815 within a molded light tube 822. This configuration allows the jet tip 810 to be smaller closer in size to a standard, non-light emitting tip used on a standard oral irrigator appliance. The one piece all molded design can be produced more economically than multipart designs using a molded water conduit jet tip with an optical fiber or other light tube attached. Further, the coaxial construction allows the tip to be rotated relative to the handle and feature what is not practical in non-coaxial designs.

As shown in FIGS. 8A-8D, the jet tip 810 is composed in part of a radiant energy module 824 at a proximal end 826 of the jet tip 810 that shines light into a molded acrylic fiber light injector 830, which in turn focuses this light into the entrance of the molded light tube 822 of the jet tip 810. The light injector 830 is fixed within an opening in a proximal end of a manifold 842 while the light tube 822 is removably inserted within a distal end 828 of the manifold 842. The light injector 830 and the light tube 822 are separated within the manifold 842 by a gap that forms a disk shaped plenum 850 in fluid communication with both the water conduit 815 and a water channel 848 in a water inlet 844 formed as an integral part of or mounted on a sidewall of the manifold 842. The water inlet 844 may form a nipple 846 for attachment of a water line to introduce water from an oral irrigator reservoir into the manifold 842. A distal seal 852, e.g., an O-ring, is located within the manifold 842 to seal against the outer surface of the light tube 822 and prevent water leakage. Similarly, a proximal seal 854, e.g., another O-ring, is located within the manifold 842 to seal against the outer surface of the light injector 830 and prevent water leakage.

The light tube 822 may be further retained within the manifold 842 by a clasp 834 or other retention mechanism. As shown in FIGS. 8A, 8B, and 8C, a spring-tensioned clasp 834 may toggle about a hinge 836 mounted on the manifold 842. The clasp 834 may be formed as a claw 838 on the distal end of the clasp 834 to interface with a retention surface 840 formed on the outer wall of the light tube 822. The retention surface 840 may be formed as an annular bulge or shelf surrounding the outer wall of the light tube 822 in order to allow the jet tip 810 to be oriented in any direction when inserted into the manifold 842. While not shown in FIGS. 8A-8D, the retention surface 840 may be located along the light tube 822 such that it also interfaces with the distal end of the manifold 842 to indicate that the light tube 822 is fully inserted within the manifold 842 and thereby prevent over-insertion that would prevent formation of the plenum 850.

At the proximal end 826 of the light tube 822, radiant energy is transmitted from the light injector 830 to the light tube 822 and water is also introduced from the plenum 850 into the water conduit 815 formed in the light tube 822. When the plenum 850 is filled with water, the light injector 830 also transmits light into the water as it travels through the water conduit 815. The water in the water conduit 815 thus also provides an additional light conducting structure as well as the cleaning jet of water when emitted from the distal end 828 of the light tube 822. This cylindrical discharged jet stream is substantially laminar and further acts as light tube for the radiant energy. The edges of the laminar stream are bordered by air, which aids in the internal reflection of the light within the water stream, thereby providing tightly focused beam of UV light to the tooth surface. Additionally, the distal end 828 of the light tube 822 may be beveled, faceted, curved, or otherwise configured to focus the radiant energy exiting the light tube 822 to enter the water stream to further enhance the focused beam of light. The water jet further acts to lift the gum tissue away from the tooth surface allowing germicidal light to access the UV photosensitive black-pigmented anaerobic bacteria beneath the gum line.

In an alternate embodiment, a system of lenses may be used to focus light into the end of the light tube 822 rather the molded light injector 830. In other embodiments, the molded light injector 830 could be replaced by a straight glass or plastic rod with a polished end placed in close proximity the light emitting die of the radiant energy module 824. While functional, in some embodiments, such as those utilizing a LED as the radiant energy source, a disadvantage of this design is that the radiant energy module 824 must be obtained in a non standard configuration in order to allow the end of such a glass or plastic rod to be placed in the required close proximity. Further, there is a decrease in efficiency as the analysis below suggests.

Figure 9A:
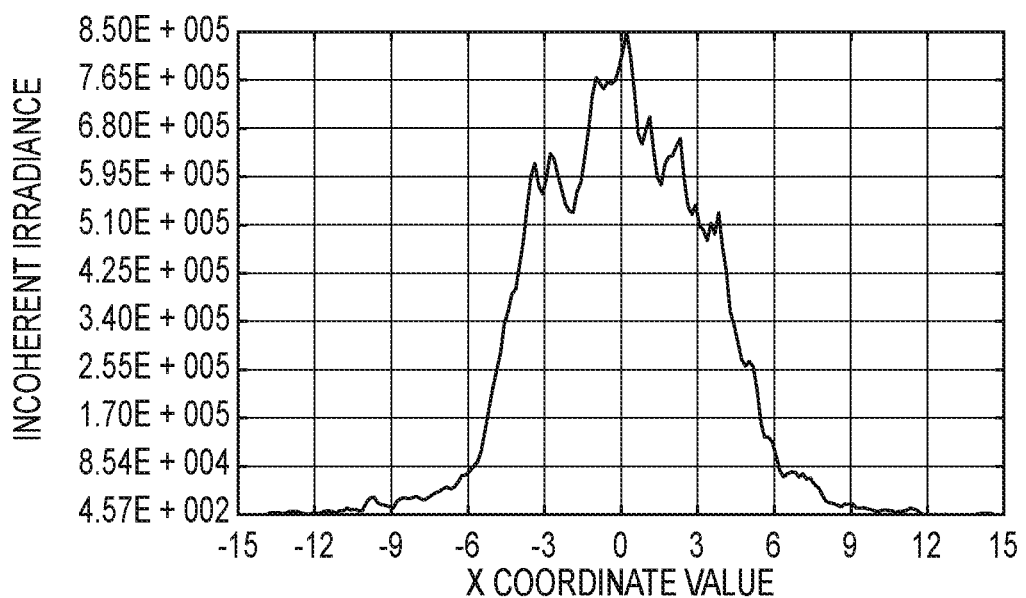
FIG. 9A is a graph depicting the incoherent irradiance measured at a detector imparted by an oral irrigator tip of the implementation of FIGS. 8A-8D in which the jet tip is formed as an integral radiant energy conduit and the radiant energy is transmitted without a corresponding water stream.

The effectiveness of the oral irrigator device with integral radiant energy delivery system of FIGS. 8A-8D, utilizing a LED as the radiant energy module 824, is shown in the computer simulation report of FIGS. 9A-11B. These reports also demonstrate the focusing ability of the light carrying water stream. In the first configuration presented in FIGS. 9A and 9B, A 1×1 mm, 405 nm LED was used as the light source. The jet tip 810 was tapered and curved with 1 mm water gap in the plenum 850. Water was in the water conduit 815 of the jet tip 810, but was not flowing to extend to the tooth surface. The target/detector size was 30×30 mm and was placed 5 mm from distal end 828 of the jet-tip 810. A mask with a hole was placed near the end of the jet-tip 810, to eliminate scattered energy. Fresnel and absorption losses are considered. The LED power is "set" to 100 watts. The incoherent irradiance plot shown in FIG. 9A is in Watts/m$^2$. In this experiment, 55.8 watts reaches the detector. The peak irradiance measured at the center of the target was $8.5 \times 10^5$ Watts/m$^2$. The highest irradiance calculated for a single location was $1.1290 \times 10^6$ Watts/m$^2$. The energy spot as shown in FIG. 9B is approximately 11.8 mm diameter, where >10% of the total energy output was imparted to the peak location.

Figure 10A:
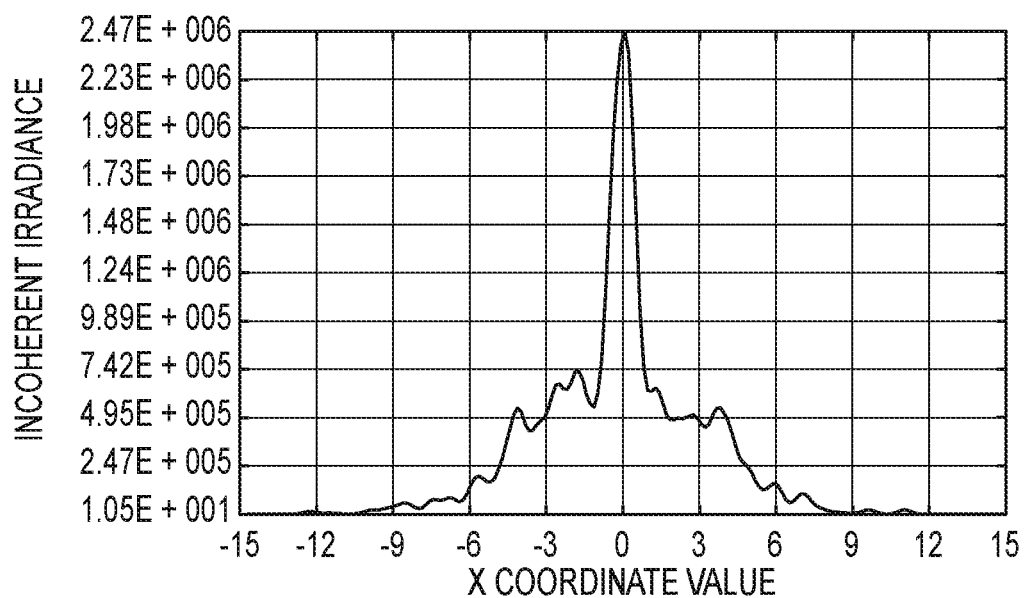
FIG. 10A is a graph depicting the incoherent irradiance measured at a detector imparted by an oral irrigator tip of the implementation of FIGS. 8A-8D in which the jet tip is formed as an integral radiant energy conduit and the radiant energy is transmitted in conjunction with a corresponding water stream.

The results of a second configuration are presented in FIGS. 10A and 10B. The radiant energy source 724 and the jet tip configuration are the same as the configuration corresponding to FIGS. 9A and 9B, but in this experiment, the water stream was flowing and extended to target/detector as it would be in actual use. In this experiment, 56.8 watts reached the detector. The peak irradiance measured at the center of the target was $2.5 \times 10^6$ Watts/m$^2$, which is three (3) times that of the configuration represented in FIGS. 9A and 9B. The energy spot as shown in FIG. 10B is more focused at approximately 9.8 mm diameter, where >10% of the total energy output was imparted to the peak location. This experiment is demonstrative of the enhancement of the bactericidal effect if the water stream is also used to focus the radiant energy on the oral tissue.

Figure 11A:
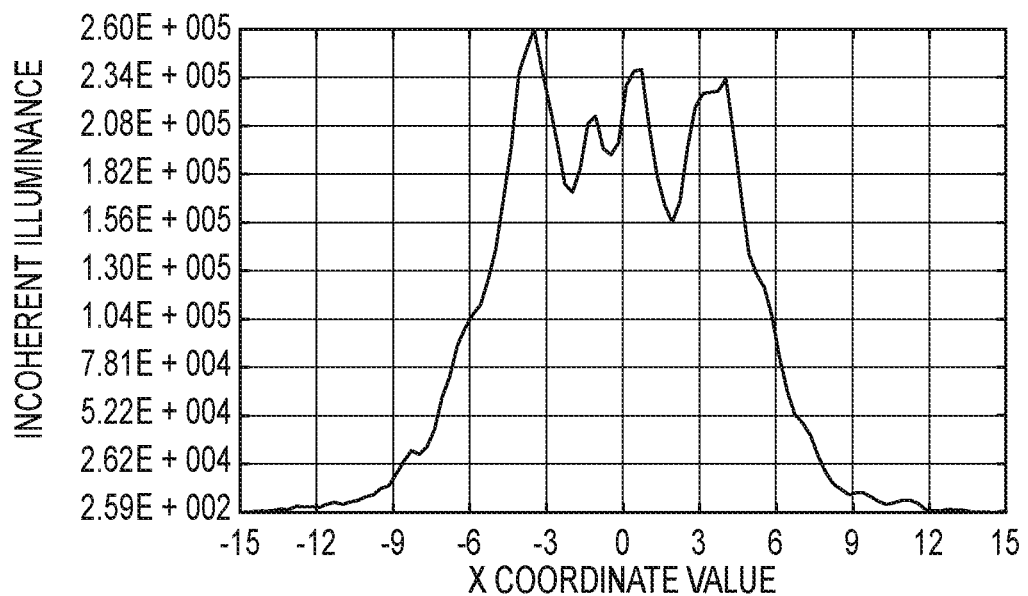
FIG. 11A is a graph depicting the incoherent illuminance measured at a detector imparted by an oral irrigator tip of the implementation of FIGS. 8A-8D in which the jet tip is formed of a tube of PMMA and the radiant energy is transmitted without a corresponding water stream.
Figure 11B:
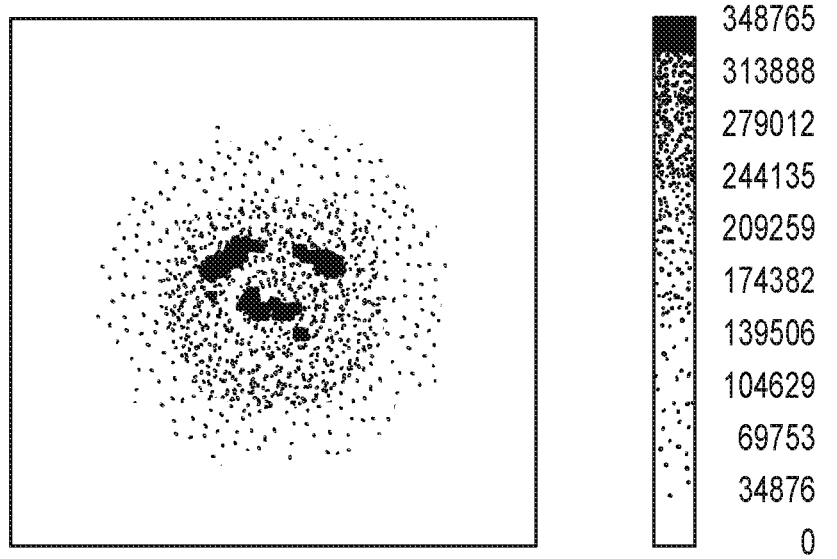
FIG. 11B is a detector image of the incoherent illuminance levels graphed in FIG. 11A.

The results of a third configuration are presented in FIGS. 11A and 11B. The light source 724 and the jet tip configuration are the same as the configuration corresponding to FIGS. 9A and 9B, except that the light injector optic was replaced by a simple cylinder formed of PMMA. Also, as in the first configuration, water was in the water conduit 815 of the jet tip 810, but was not flowing to extend to the tooth surface. In this experiment, 29 watts reached the detector. Also in this experiment, the energy at the detector was measured in illuminance rather than irradiance to provide an alternate method of quantizing the effectiveness. The peak illuminance measured at the center of the target was $2.6 \times 10^5$ lm/m$^2$ of energy. The highest illuminance calculated for a single location was 3.48×105 lm/m$^2$. The energy spot as shown in FIG. 11B is less focused at approximately 17 mm diameter, where >10% of the total energy output was imparted to the peak location.

Figure 12:
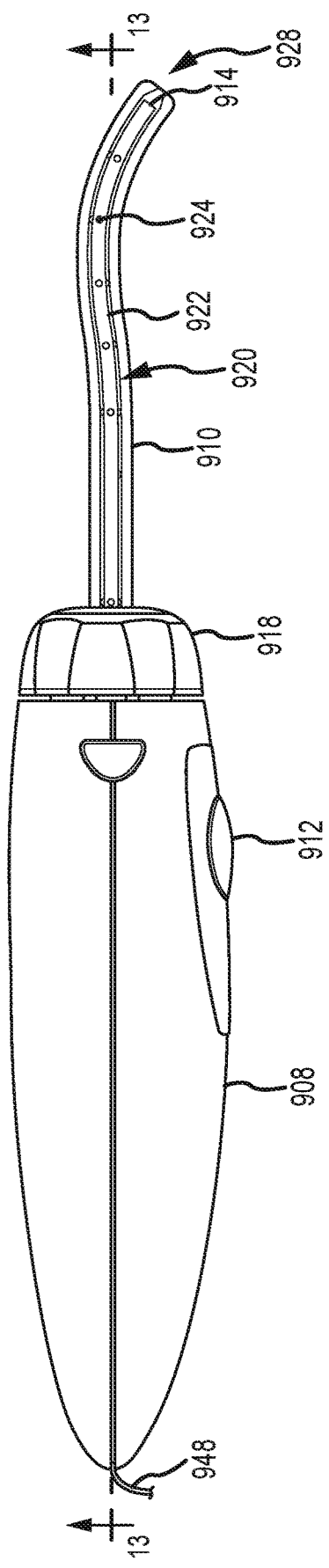
FIG. 12 is a side elevation view of another implementation of an oral irrigator jet handle with a radiant energy source transmitted via a light guide positioned coaxially within a fluid conduit of the jet tip.
Figure 13:
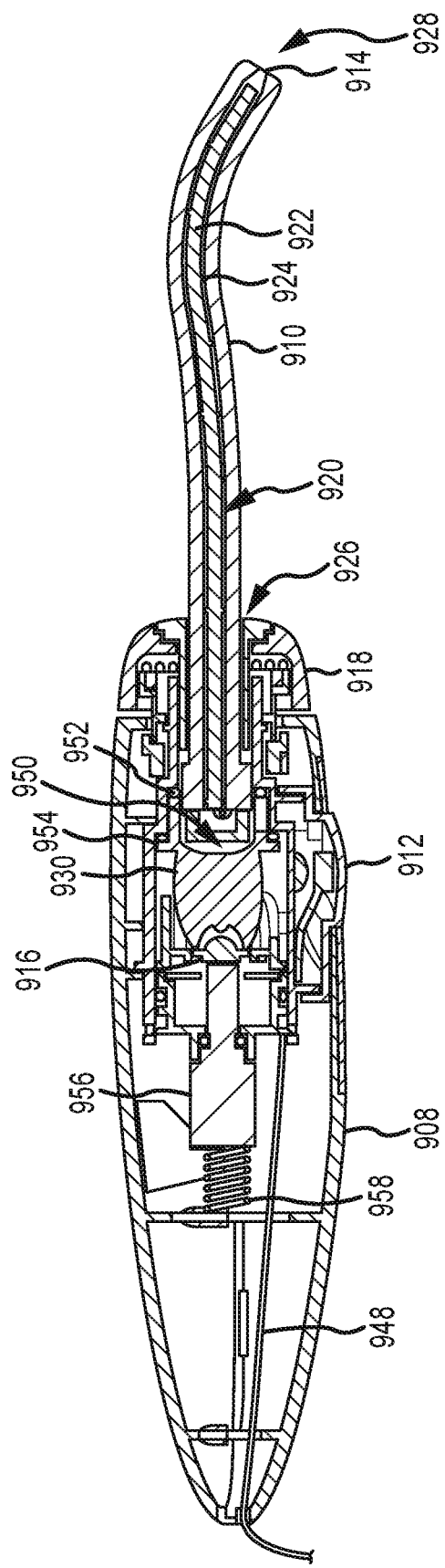
FIG. 13 is a cross-section view of the oral irrigator jet handle of FIG. 12 taken along line 13-13.

FIGS. 12-19 depict another implementation of jet handle 908 for use with an oral irrigator system to provide a combination of a fluid stream and radiant energy to an oral cavity. As shown in FIGS. 12 and 13, a jet tip 910 extends from the distal end of the jet handle 908 and a fluid conduit 948 connects the jet handle 908 to a pump and fluid reservoir in the base unit (not shown). In addition, a control wire may also extend between the jet handle 908 and the base unit to allow the user to control the pump, the radiant energy source, or both, via one or more actuators 912 located on the jet handle 908. A retention cap 918 holds the jet tip 910 together with the jet handle 908 and allows for removal and replacement of the jet tip 910 as necessary.

The jet tip 910 is provided as a hollow conduit with a proximal end 926 that is received within the jet handle 908 and a distal end 928 that tapers slightly in diameter as compared to the proximal end 926. A light guide 922 extends coaxially within the lumen of the jet tip 910. The light guide receives the radiant energy from a light source (as further described below) and, as a result of an index of refraction of the material forming the light guide 922, the light energy is internally reflected within the light guide 922 such that it does not escape until it reaches the distal end 928. The light guide 922 is of a smaller outer diameter than the diameter of the lumen of the jet tip 910 and similarly tapers in diameter. The space between the outer surface of the light guide 922 and the inner diameter of the jet tip 910 forms a fluid channel 920. In operation, the fluid pumped by the oral irrigator exits the jet tip 910 through an outlet 914 on the distal end 914. At this location, the light energy exits the light guide 922 and is carried within the fluid stream exiting the jet tip 910. The fluid stream is laminar in form and similarly internally reflects the light exiting the light guide 922 to deliver the radiant energy to the same location as the fluid stream.

Figure 14:
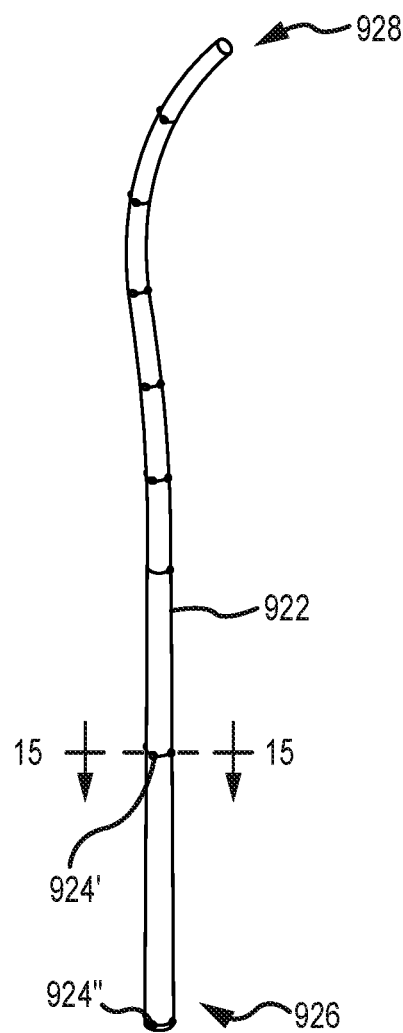
FIG. 14 is an isometric view of a light guide used in the jet handle of the oral irrigator of FIG. 12.
Figure 15:
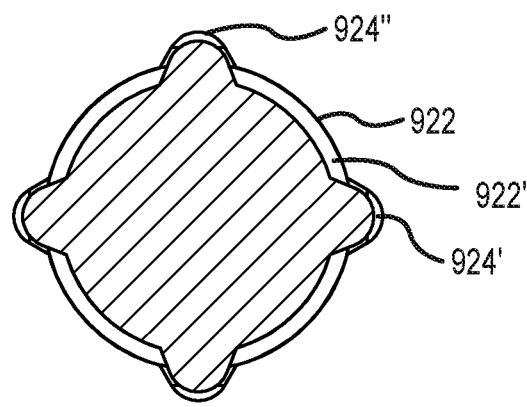
FIG. 15 is a cross-section view of the light guide of FIG. 14 taken along line 15-15.
Figure 16:
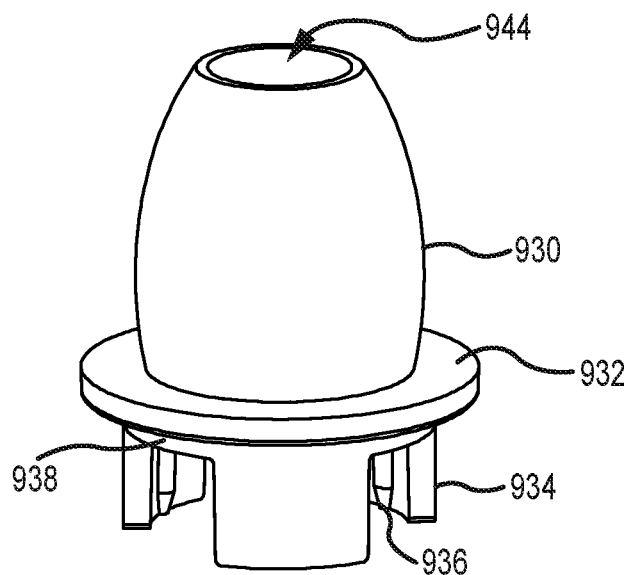
FIG. 16 is an isometric view of a collimator used in the jet handle of the oral irrigator of FIG. 12.
Figure 17:
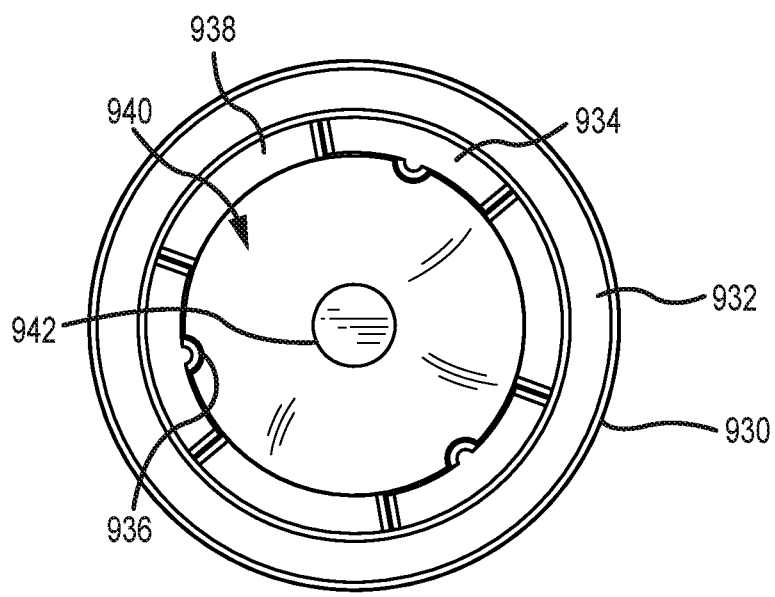
FIG. 17 is a bottom plan view of the collimator of FIG. 16.
Figure 18:
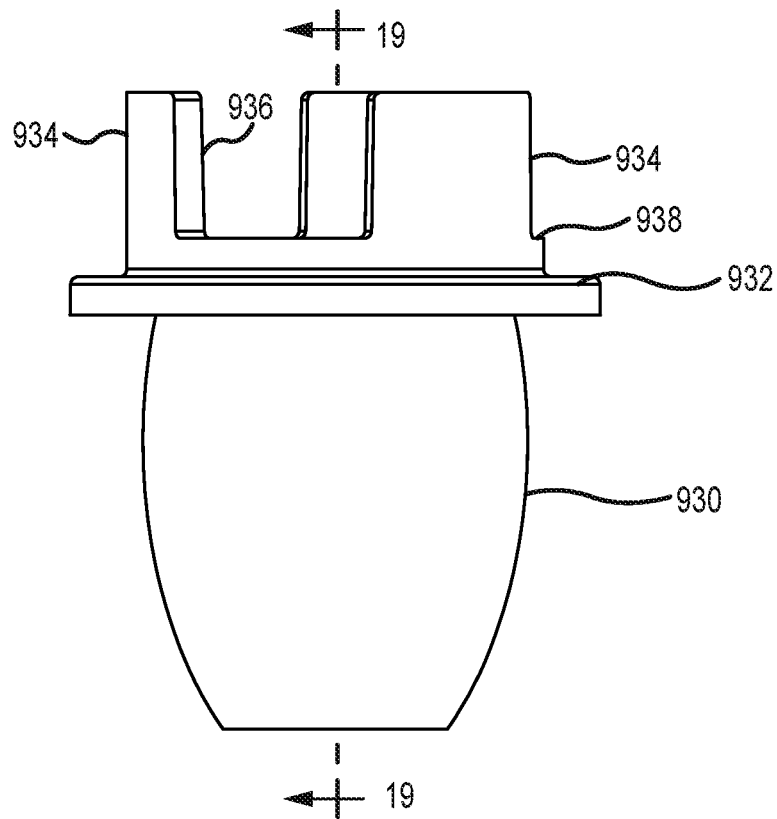
FIG. 18 is a side elevation view of the collimator of FIG. 16.
Figure 19:
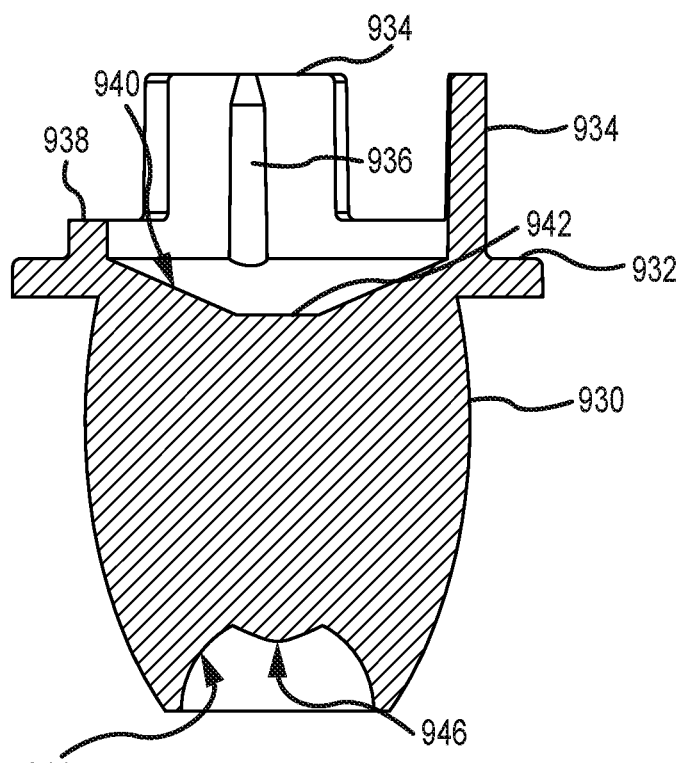
FIG. 19 is a cross-section view of the collimator of FIG. 16 taken along line 19-19 of FIG. 18.

FIGS. 14 and 15 show the light guide 922 independently and in greater detail. A plurality of bumps 924 is formed on an outer surface of the light guide 922. The bumps 924 are provided frictionally fit the light guide 922 within the jet tip 910 and to maintain uniform spacing between the outer surface of the light guide 922 and the inner wall of the jet tip 910 to provide the fluid channel 920 within the jet tip 910. There is no set number of or location for the bumps 924 required. As shown in FIG. 14, the bumps may be spaced at various distances longitudinally as well as locations circumferentially. Also, as shown in FIG. 15, the outer surface 922' of the light guide 922 is larger at the proximal end and tapers toward the distal end. This is evident in the differing radii of the bumps 924" at the base of the light guide 922 as compared to the bumps 924' further distally along the light guide 922. In the embodiment shown, locations for the bumps 924 were selected to ensure the water channel 920 remains open along the entire length of the jet tip 910. It is desirable to minimize the number of bumps 924 on the light guide to minimize the obstacles within the fluid channel 920 and to optimize the internal reflection of the light within the light guide 922.

A light source 916, e.g., an LED emitting light at a desired wavelength or over a desired bandwidth or a laser diode, is mounted within the jet handle 908 below the proximal end of the jet tip 910. A heat sink 956, e.g., an aluminum block, may be held in compression with the light source 916 by a spring bias 958 in order to cool the light source 916 when in operation. A collimator 930 is mounted between the light source 916 and the proximal end of the light guide 922. The collimator 930 is shown in greater detail in FIGS. 16-19. The proximal end of the collimator 930 functions as a collector having a concave surface 944 that transitions into a convex surface 946 to collect and focus the light from the light source 916. In exemplary embodiments, the radius of the sidewalls of the collimator 930 may be between 0.5-1.5 degrees. In the embodiment of FIGS. 16-19, the radius is approximately 0.68 degrees. The distal end of the collimator is formed as a lens with a flat base 942 and a distally extending conical sidewall 940 that may be between 20°-30° for best effect. In the embodiment of FIGS. 16-19, the angle of the conical sidewall 940 with respect to the base 942 is approximately 23.7 degrees. However, depending on the light source 916 used, e.g., a diode, LED or other light source, the collimator may be modified to accommodate the varying light intensities and/or lens structures.

A superstructure extends above the distal end of the collimator 930 forming a circumferential flange 932 and a plurality of tabs 934. In the embodiment shown, three tabs 934 are spaced equidistantly around the output lens of the collimator 930 to define a plenum 950 for receipt of fluid from the fluid conduit 948 and injection of the fluid into the water channel 920. A vertical boss 936 is formed on an inner wall of each of the tabs 934 for interfacing with the proximal end of the jet tip 910. A proximal seal 952, e.g. an O-ring, is positioned upon the distal side of the flange 932 to seal the plenum 950 area with respect to an internal housing structure. A lip 938 may extend between each of the tabs 934 adjacent the flange 932 to aid in maintaining the position of the proximal seal 952 when placed under pressure. The spring bias 958 also provides a sealing pressure on the collimator 930 to assist in sealing the plenum 950. A distal seal 954, e.g., and O-ring, is positioned on the distal ends of the tabs 934 to engage with an internal housing structure and an outer wall of the jet tip 910 to provide a sidewall seal for the distal end of the plenum 950.

In operation, the jet handle of the embodiment of FIGS. 12-19 flows fluid through the fluid conduit 948 into the plenum 950, and within the water channel 920 in the jet tip 910. When the light source 916 is activated, the light energy is collected by the collimator 930 for a focused output through the plenum and into the proximal end of the light guide 922. The light travels through the light guide 922 and exits the distal end where it is within the water stream exiting the outlet 914 of the jet tip 910. A combination of a pressurized water stream and effective radiant energy is thus delivered simultaneously and coaxially at a common location within the oral cavity.

Figure 21A:
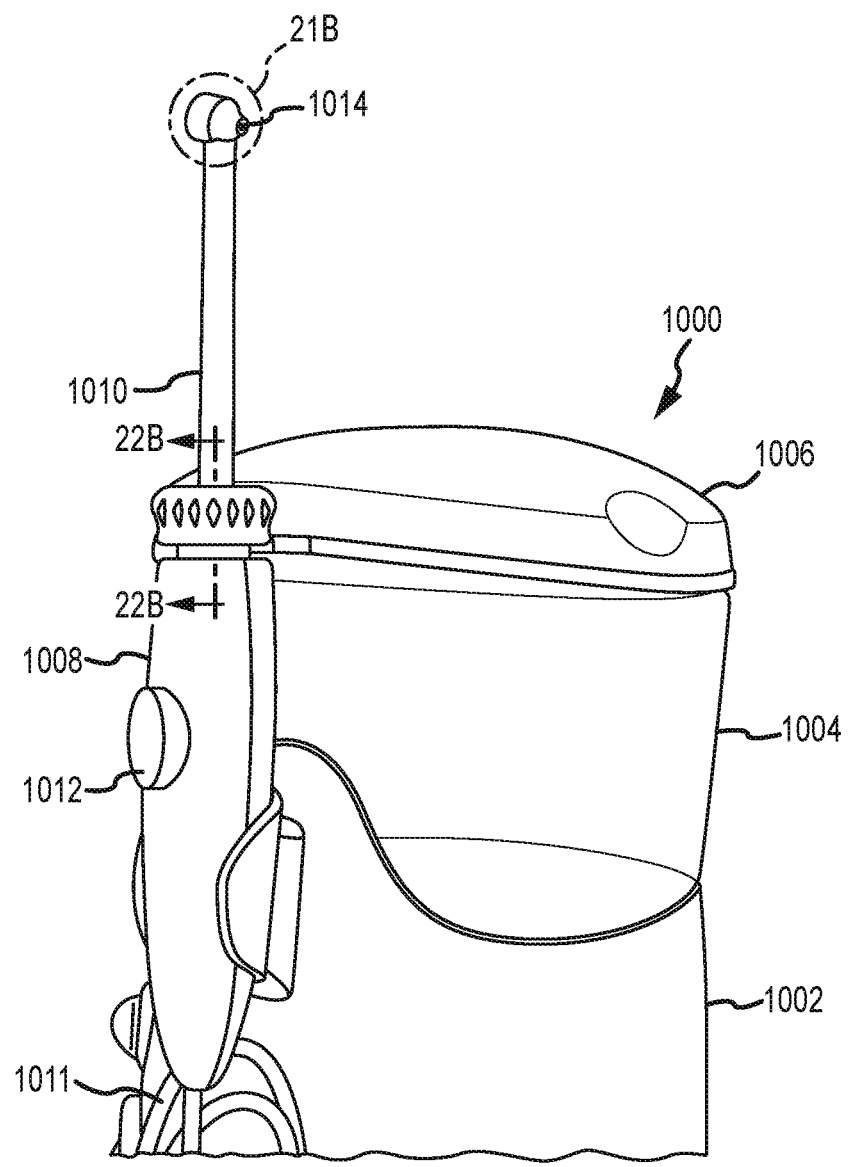
FIG. 21A is an isometric view of an implementation of an oral irrigator including a radiant energy source disposed within a terminal end of a jet tip.
Figure 21B:
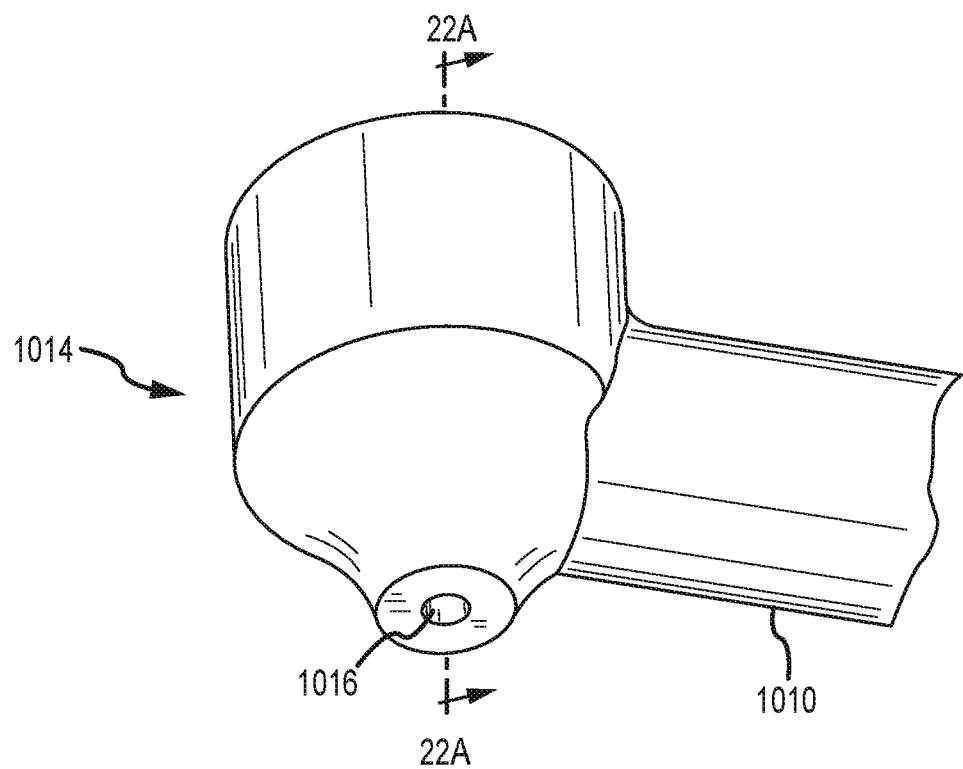
FIG. 21B is an enlarged view of the terminal end of the jet tip of the oral irrigator shown in FIG. 21A.

FIGS. 21A and 21B depict another implementation of jet handle 1008 for use with an oral irrigator system to provide a combination of a fluid stream and radiant energy to an oral cavity. An oral irrigator 1000 is shown having a base housing 1002, which incorporates the pump powered by line voltage. A reservoir 1004 having a lid sits atop the base housing 1002 and serves to supply the water to the jet tip 1010. The reservoir 1004 is fluidically connected to the pump in order to pump water through a water line 1011 to the jet handle 1008. The jet tip 1010 is fluidically connected to the jet handle 1008 so that the pumped water flows through the jet tip 1010. For example, as can be seen in the cross-section view of FIG. 22A, the jet tip 1010 may include a fluid channel 1024 and an electrical channel 1022. These channels 1022, 1024 may be similar to the water conduit 610 and the energy conduit 622, respectively, as shown in FIG. 6A. The fluid channel 1024 provides a fluid lumen or pathway from the handle 1008 through the jet tip 1010, and the electrical channel 1022 provides a pathway for electrical wiring and/or other devices within the jet tip 1010.

The jet tip 1010 has a tip head 1014 that is positioned so as to cause the water stream to enter the oral cavity and flush bacteria therefrom. A top portion 1032 of the tip head 1014 may slope upwards to form a conical shape in a center area of the top portion 1032. In some embodiments as shown, the wall of the conical area may be slightly concave. An outlet aperture 1016 of the jet tip 1010 of the tip head 1014 may be formed within the center and apex of the conical area. In this embodiment, the outlet aperture 1016 may thus be slightly raised above other areas of the top portion 1032. The conical area of the top portion 1032 increases the total length of the outlet aperture 1016 as it extends through the conical portion into the inner cavity of the tip head 1014. However, it should be noted that the top portion 1032 may be formed in a variety of other shapes and the shape illustrated in FIGS. 21A-22A is merely one embodiment. The outlet aperture 1016 provides an exit for fluid and/or radiant energy from the jet tip 1010. In some embodiments the tip head 1014 of the jet tip 1010 may form the outer housing of a radiant energy source package. In these embodiments, the tip head 1014 along with the package housed within may be removable from the jet tip 1014.

Figure 22B:
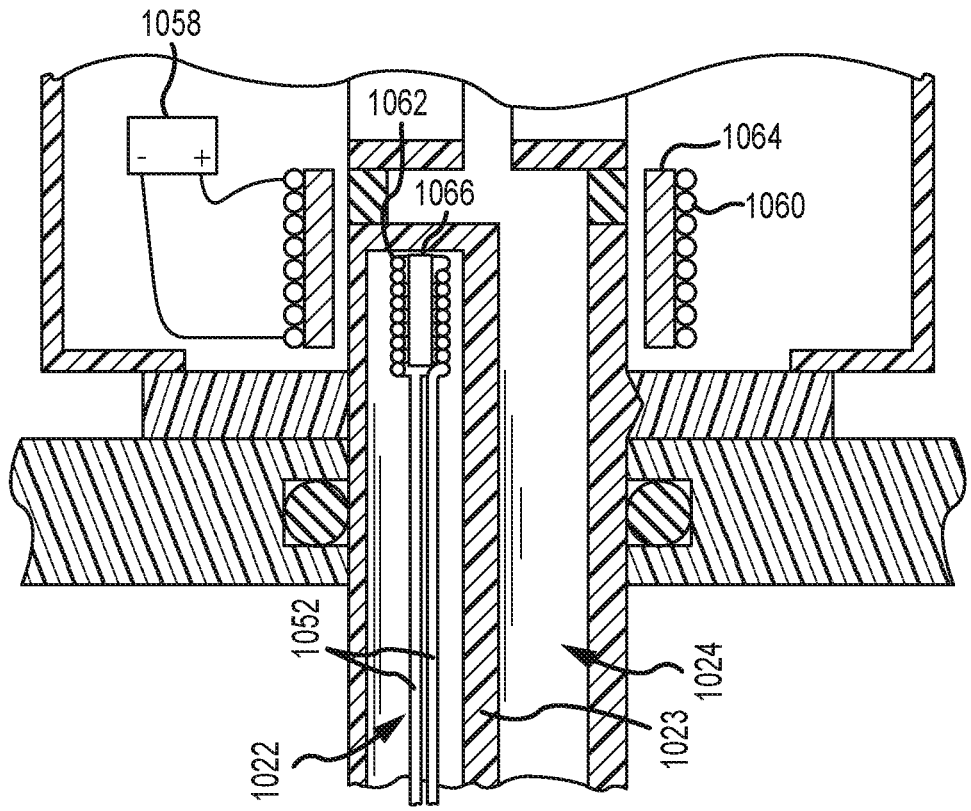
FIG. 22B is a cross-section view of the interface between the jet tip and the handle illustrated in FIG. 21A taken along line 22B-22B in FIG. 21A.
Figure 22A:
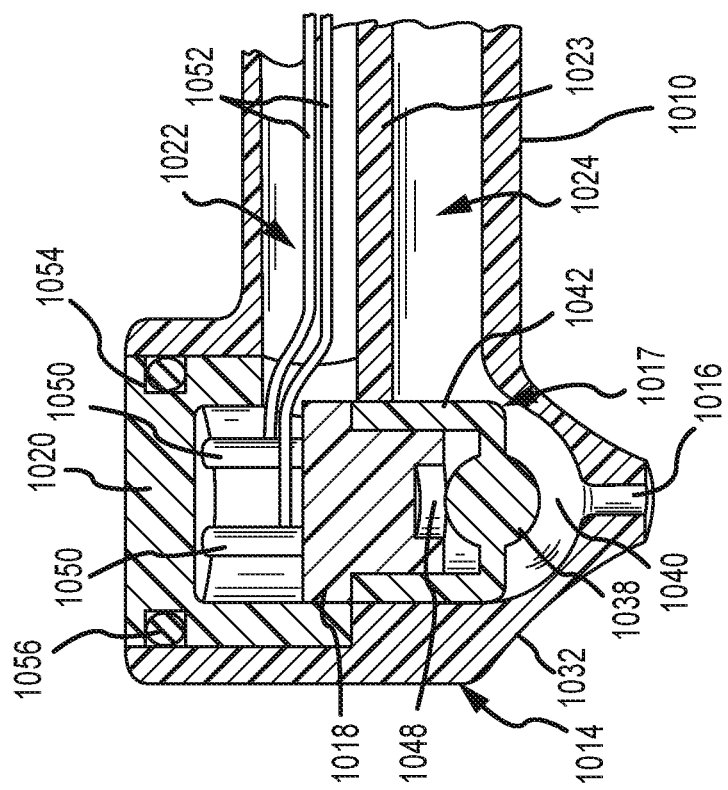
FIG. 22A is a cross-section view of the jet tip illustrated in FIG. 21B taken along line 22A-22A in FIG. 21B.

The outlet aperture 1016 may have separate pathways for fluid and radiant energy, or the pathways may be combined, such that the fluid and the radiant energy are combined together to exit the jet tip 1010. For example, as shown in FIG. 22A, illustrating a cross-section view of the jet tip 1010, the tip head 1014 of the jet tip 1010 may house a laser diode 1018 (e.g., Violet Laser Diode No. NDHV4313D available from Nichia Corporation, Tokushima-Ken, Japan) as a radiant energy source positioned to direct radiant energy within a fluid inlet 1017 exiting the outlet aperture 1016. Thus, in some embodiments, the fluid travels from the reservoir 1004 to the outlet aperture 1016 in the jet tip 1010 to combine with the radiant energy produced from the laser diode 1018 housed within the jet tip 1010.

In some implementations the laser diode 1018 produces a light beam directed into the outlet aperture 1016. These implementations allow the fluid traveling from the reservoir 1004 via the fluid channel 1024 and through the fluid inlet 1017 to carry the radiant energy into a user's mouth. As the fluid impacts the gum line, it displaces the gums and other tissue, allowing the radiant energy to be directed to bacteria and other organisms within a user's mouth. And as discussed above with respect to other embodiments, radiant energy may kill numerous varieties and amounts of bacteria that may be present in a person's mouth.

The fluid channel 1024 provides a path for fluid to flow from the reservoir 1014 to the outlet aperture 1016. The electrical channel 1022 provides a path for electrical wires or other forms of electrical communication between the laser diode 1018 and a power source (e.g., line voltage, batteries). In other implementations, the electrical channel 1022 may house a fiber optic cable or other light transmission mechanism. The electrical channel 1022 and the fluid channel 1024 may be substantially parallel to each other and may be sealed off from each other. This helps prevent fluid from entering the electrical channel 1022 and potentially damaging the electrical communication elements disposed within the electrical channel 1022. In some implementations the fluid channel 1024 and the electrical channel 1022 may have substantially the same dimensions, however, in other implementations they may have different dimensions. For example, the electrical channel 1022 may only need to accommodate thin wires and thus may be smaller in diameter than the fluid channel 1024.

The fluid channel 1024 and the electrical channel 1022 may be separated by a median 1023 that acts as a boundary between the two channels 1022, 1024, sealing them off from each other. The median 1023 may terminate at the outer housing of the laser diode 1018. In this implementation, the housing or other portions of the laser diode 1018 may act to seal fluid from the fluid channel 1024 from entering the electrical channel 1022.

The electrical channel 1022 may terminate adjacent a base of the laser diode 1018. For example, as shown in FIGS. 22A and 22B, the laser diode 1018 may include connector pins 1050, prongs, inputs, receptacles, or the like for making an electrical connection to connect the laser diode 1018 to a power source 1058. As shown in the figures, the pins 1050 connect to lead wires 1052 that travel through the electrical channel 1022 in the jet tip 1010 to connect with a power source. The electrical connection between the jet tip 1010 and a power source in the handle 1008 or base housing 1002 may be direct as with a plug connection or indirect, e.g., via inductive coupling. For example, the handle 1008 may include a first inductive coil 1060 (i.e., coiled or wound conductive wiring) and the lead wires 1052 may terminate in the base of the jet tip 1010 at a second inductive coil 1062 with similar coiled or wound wires. The first inductive coil 1060 may receive electricity from a battery 1058, wired power source, or the like, to induce a voltage in the second coil 1062. The second coil 1062 then may be connected either directly or indirectly to the laser diode 1018. Additionally, one or both of the inductive coils 1060, 1062 may be wrapped around a ferromagnetic core 1064, 1066 (e.g., a pot core as available from Magnetics, Inc., Pittsburgh, Pa.) to assist in the inductive coupling between the two coils.

Implementations utilizing an inductive power coupling may be beneficial as corrosion or electrical shorts between the power source and the laser diode 1018 may be reduced. This is because the inductive power coupling does not require a physical connection between the first coil and the second coil. Thus the first coil in the jet tip 1010 may be completely sealed within the electrical channel 1022 and no water or other fluid can reach the wires. No electrical connections have to be physically detached in order for the jet tip 1010 to removed or replaced, thus substantially preventing fluid and/or air from contacting the electrical lead wires, connectors, or the laser diode 1018. Likewise, within the handle 1008, the lead wires and the power source 1058 (if within the handle 1008) may be isolated from the water flow to prevent corrosion and electrical shorting.

The electrical connection area of the laser diode 1018 may be covered by an end plug 1020 that seats within an opening defining a cavity within the tip head 1014. The end plug 1020 substantially covers and encases the electrical connections between the laser diode 1018 and the electrical connection, thus preventing the connection from being damaged by fluid, user movements, or the like. The end plug 1020 may also help secure the laser diode 1018 to the jet tip 1010. For example, the end plug 1020 may include a fastener or have a snap fit connection to secure the laser diode 1018 to the jet tip 1010. The end plug 1014 may further define an annular channel 1054 within an external wall of the end plug 1020 to receive an O-ring to provide a fluid-tight seal for the cavity in the tip head 1014, thus protecting the electrical connection with the radiant energy source.

In some implementations, the laser diode 1018 or it may be integrated into the jet tip 1010 while in other implementations it may be a separate element that may attach to the end of the jet tip 1010. In still other implementations, the laser diode 1018 may be located within the handle 1008. In these implementations, the electrical channel 1022 may include a fiber optic cable or the like (see e.g., the energy conduit 610 illustrated in FIG. 6A) to transmit the radiant energy from the laser diode 1018 into the tip head 1014 of the jet tip 1010. These implementations may be used if the laser diode 1018 is a laser diode, for example, as the radiant energy emitted from a laser diode may be substantially collimated light rather than omnidirectional light that may scatter in many angles. Thus, most of the energy may be directed out of the outlet aperture 1016 of the jet tip 1010, rather than inwards or in other directions along the path between the laser diode 1018 and the tip head 1014 of the jet tip 1010.

It should be noted that the laser diode 1018 may be any element that can produce radiant energy, such as a LED, laser diode, or possibly an incandescent source. However, in embodiments utilizing a laser diode, a heat sink or other heat dissipating device may be omitted or substantially reduced in size as laser diodes may generate less heat than a LED or other radiant energy sources. Additionally, although a laser diode may not produce as much light as a LED, the light or beam emitted from a laser diode may be substantially collimated as it is produced in a substantially narrow beam or cone and thus actually direct up to 10 times more light energy into the water stream output from the jet tip 1010 as compared to other, scattering radiant energy sources. This may be beneficial as the narrower the beam, the more radiant energy may be directed into the fluid stream after exiting the laser diode 1018 (versus scattering or reflecting in various directions), and thus more energy may be directed into a user's mouth.

Also, in some embodiments, the laser diode 1018 may be placed near or within a fluid flow path from the jet tip 1010 and thus may utilize the fluid flow as a method of cooling and the heat sink may be omitted or reduced in size. Additionally, the laser diode 1018 may include a lens, collimator, or other energy directing/condensing elements. In these embodiments, the laser diode 1018 may be placed farther away from the outlet aperture 1016, as the light may be substantially focused to prevent scattering or reflection in various directions.

In the exemplary embodiment of FIG. 22A, a spherical lens 1038 is supported above the laser diode 1018 in a fluid pocket 1040 by a lens mount 1042. The lens mount 1042 may hold the spherical lens 1038 above a light emitting region 1048 of the laser diode 1018 and below the outlet aperture 1016. In some embodiments, the lens mount 1042 may include a skirt which surrounds an outer portion of the laser diode 1018, securing the spherical lens 1038 in place. The lens mount 1042 may be integrally formed with the spherical lens 1038 (e.g., as a molded polycarbonate, acrylic, thermoplastic, or thermoset structure) or the lens mount 1042 may be separate from the spherical lens 1038. Also, it should be noted that the lens mount 1042 may be omitted in favor of a molded structure as part of the tip head 1014 that holds the spherical lens 1038 in position.

Further, the lens mount 1042 may act as a heat sink for the laser diode 1018. The lens mount 1042 may be substantially surrounded by fluid and may assist in the dissipation of heat produced by the laser diode 1018 or other radiant energy source. For example, as the fluid travels around the spherical lens 1038 and the lens mount 1042 the heat produced by the laser diode 1018 may be transferred through the lens mount 1042 and the spherical lens 1038 and imparted to the fluid in the fluid pocket 1040 exiting the jet tip 1010. In these implementations, a heat sink or other heat-dissipating device may be omitted from the laser diode 1018, as the fluid may act to substantially reduce the heat produced from the spherical lens diode 1026. However, in other implementations, a heat sink or other device may be used either in combination with or instead of fluid-cooling the laser diode 1018, e.g., if the lens mount 1042 and the spherical lens 1038 are poor heat conductors.

Additionally, in some embodiments, the lens mount 1042 may act as a seal to substantially prevent fluid from the fluid channel 1024 and fluid pocket 1040 from coming in contact with the laser diode 1018 and/or the pins 1050. In the exemplary embodiment shown in FIG. 22A, the skirt portion of the lens mount 1042 extends downwards and intersects the median 1023. The lens mount 1042 may be fixed to the laser diode 1018, the median 1023, and inner surfaces of the tip head 1014 with an adhesive, e.g., a heat-resilient and waterproof adhesive. By using a waterproof adhesive to connect the lens mount 1042, fluid may travel from the fluid inlet 1017, around the lens mount 1042 in the fluid pocket 1040, and to the outlet aperture 1016 without leaking across the median 1023 or behind the laser diode 1018 to the electrical connections, thereby protecting against shorts and corrosion.

The spherical lens 1038 acts to focus the light from the light emitting region 1048 and direct it towards the outlet aperture 1016. While the lens is depicted as spherical in this embodiment, the lens may be formed in other shapes, e.g., cylindrical, conical, or concave or convex disks, depending upon the output of the radiant energy source and focal distances required by the tip configuration. In some embodiments, the spherical lens 1038 may sit substantially in the middle of the lens mount 1042. The spherical lens 1038 may be formed of a molded acrylic or other plastic, glass, or other similar refractive materials.

The fluid pocket 1040 is formed under the top portion 1032 of the tip head 1014 between the upper surface of the spherical lens 1038 and the outlet aperture 1016. The fluid area 1040 acts as a combination location, and fluid from the jet tip 1010 may be combined with the radiant energy from the laser diode 1018 further collimated by the spherical lens 1038 is entrained within the water flowing through the fluid pocket 1040 and exiting the outlet aperture 1016. The fluid pocket 1040 may also act to help cool the laser diode 1018 and/or the spherical lens 1038, as discussed above. The dimensions of the fluid pocket 1040, particularly the distance between the bottom surface of the top portion 1032 and the top surface of the spherical lens 1038, may be altered depending on the strength and/or light collimation desired. For example, the shorter the distance between the spherical lens 1038 and the outlet aperture 1016, the more collimated the radiant energy may be as it exits the outlet aperture 1016. This is because in some instances, fluid surrounded by plastic or other materials may not be as an effective light guide as fluid surrounded by air, and more light may be reflected at an angle that escapes the fluid stream exiting the outlet aperture 1016 the farther the light and fluid must travel.

Figure 23:
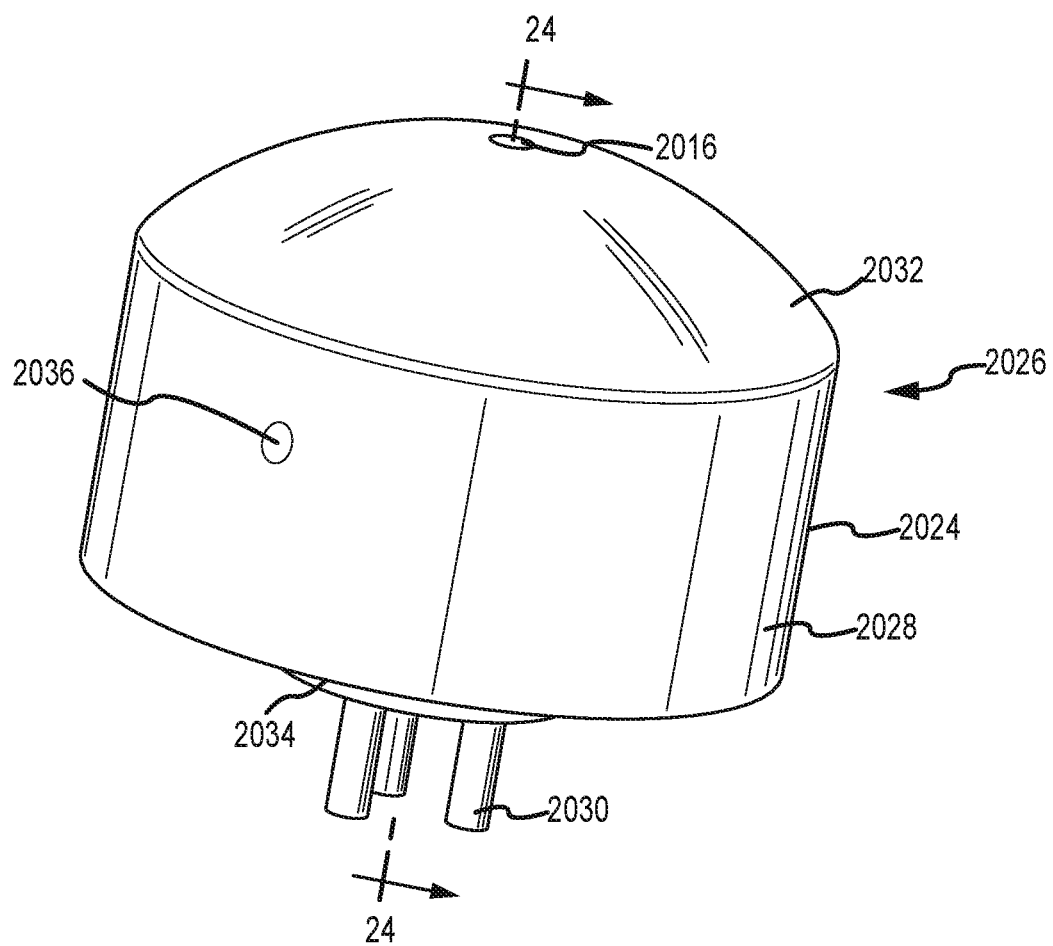
FIG. 23 is an isometric view of an embodiment of a removable radiant energy source removed from the jet tip.
Figure 24:
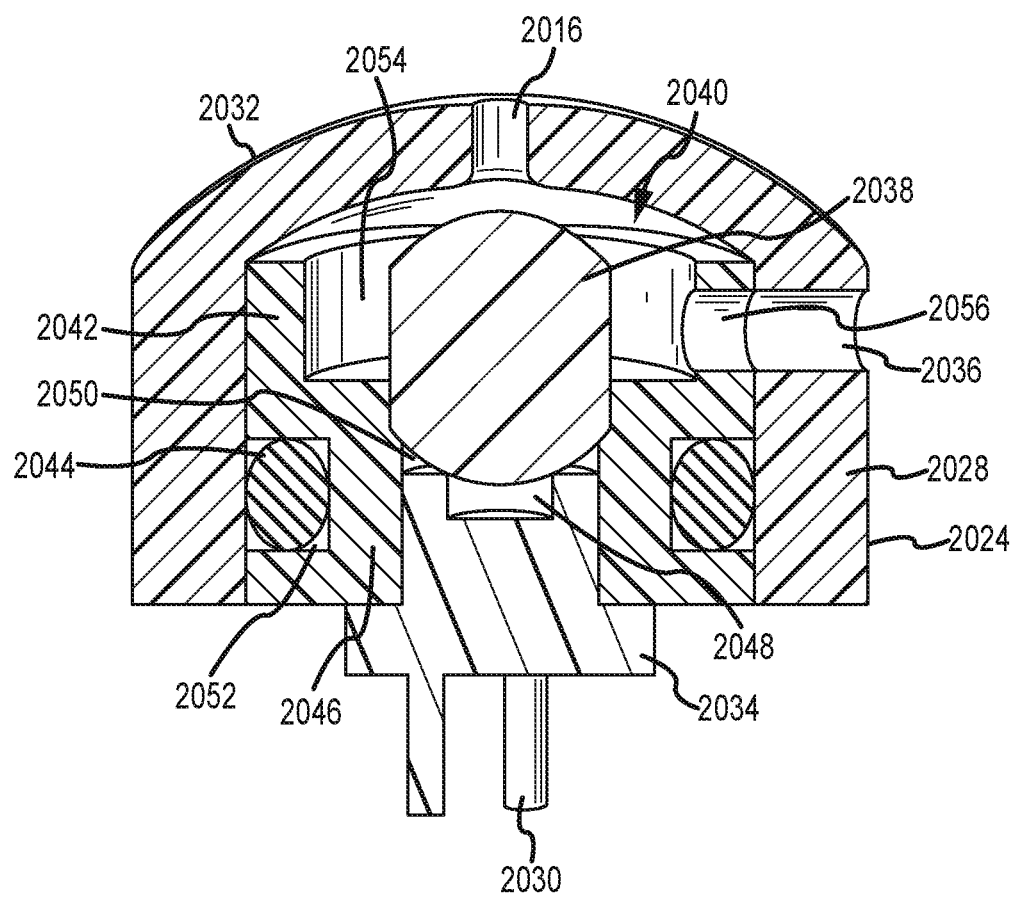
FIG. 24 is a cross-section view of the radiant energy source illustrated in FIG. 23 taken along line 24-24 in FIG. 23.

FIG. 23 illustrates a second embodiment of the radiant energy source and FIG. 24 illustrates a cross-section view of the radiant energy source illustrated in FIG. 23. In this embodiment, the radiant energy source may be a removable laser diode package 2026. In this embodiment, an outer housing 2024 includes a main body 2028 and a top portion 2032. The main body 2028 and the top portion 2032 may be inserted into a cavity within the jet tip to form the terminal end or head of the jet tip. Thus, the diode package 2026 may be removable from the jet tip. However, in other embodiments, the diode package 2026 may be integrated within the jet tip. Additionally, in this embodiment, the end plug of the tip head may be integral with the jet tip to form a bottom part of a cavity into which the diode package 2026 is inserted. The end plug portion may house electrical receptacles for receiving the pins 2030 of the diode package 2026.

The housing 2024 may be cylindrically shaped and house or encase the components of the removable laser diode package 2026. The cylindrical outer wall of the main body 2028 defines a water channel aperture 2036 near the upper portion of the main body 2028 before transitioning to the top portion 2032. The water channel aperture 2036 fluidly connects the diode package 2026 and the water channel in the jet tip, allowing water from the reservoir to be transmitted to the outlet aperture 2016. The size and/or diameter of the water channel aperture 2036 may be varied depending on the desired fluid flow volume/pressure out of the jet tip. For example, the larger the diameter of the water channel aperture 2036, the more fluid may flow from the jet tip to the outlet aperture 2016.

The top portion 2032 extends from a top edge of the main body 2028 and covers the main body 2028. As can be seen from FIG. 23, the top portion 2032 includes the outlet aperture 2016 at its center apex. As discussed above, the outlet aperture 2016 provides an exit for fluid and radiant energy. In some embodiments, the top portion 2032 and the main body 2028 may be integrated with the jet tip, and in other embodiments they may be a separate housing for the diode package 2026 that is removable from the jet tip 2010.

A semiconductor laser diode 2034 extends from a bottom end of the main body 2028. The laser diode 2034 is electrically connected to the power source. Several connection pins 2030 extend from the base of the laser diode 2034 to connect the diode 2034 to the power wires or other electrical connection. There may be two, three, or more pins 2030, depending on the diode used. For example, in some embodiments, in addition to electrical connections, one of the pins 2030 may be used to provide a feedback signal from the diode package 2026 to a computer or processor. In some implementations, feedback may not be desired and thus additional pins 2030 beyond electrical contacts, may be omitted. Further, the pins 2030 may be inserted into a receiving receptacle, outlet or the like. For example, the tip head of the jet tip may have connection receptacles into which the pins of the diode package 2026 may be plugged. Such an embodiment allows the pins 2030 of a diode package 2026 to be quickly connected and disconnected to the jet tip 2026.

In the embodiment shown in FIGS. 23 and 24, a barrel-shaped lens 2038 is located in front of a light emitting region 2048 of the laser diode 2034. The barrel lens 2038 may further collimate the light as it is emitted from the laser diode 2034 and focus the emitted light into a more coherent beam. The barrel lens 2038 may be mounted above the laser diode 2034 and slightly below the inner surface of the top portion 2032 of the outer housing 2024, under the outlet aperture 2016. In these implementations, the barrel lens 2038 may focus light into a water stream in the outlet aperture 2016 and minimize light reflection off the top portion 2032 outside or around the outlet aperture 2016.

In some embodiments, the barrel lens 2038 may be generally cylindrical with curved end walls, and positioned such that the longer sides of the barrel lens 2038 are substantially parallel to the main body 2028. Other implementations of collimating lenses may also be used. The barrel lens 2038 may be glass or another material (e.g., acrylic, polycarbonate, crystal) with appropriate refractive qualities. The barrel lens 2038 may be spaced farther away from the outlet aperture 2016 than other lenses or embodiments of the radiant energy source 2018 because of the collimating effects. However, in other implementations, the barrel lens 2038 may be spaced in varying distances from the outlet aperture 2016. Additionally, in some embodiments, the barrel lens 2038 may be omitted, or may be replaced with another shaped lens as discussed previously above.

The barrel lens 2038 may be secured in place above the laser diode 2034 and below the outlet aperture 2016 via a sealing plug 2046. The sealing plug 2046 seals the laser diode 2034 and the pins 2030 from contact with the fluid. The sealing plug 2046 may be formed as a generally cylindrical body defining a central axial lumen 2050. In this exemplary embodiment, a bottom end of the axial lumen 2050 may be sized to accept the outer diameter of the laser diode 2034. However, a diameter of a top end of the axial lumen 2050 may be larger to create an annular space 2054 around the barrel lens 2038. The axial lumen 2050 of the sealing plug 2046 may further have an intermediate stepped area that receives and holds the barrel lens 2038 in axial alignment with the light emitting region 2048 of the laser diode 2034.

An inlet aperture 2056 may also be formed within a sidewall of the sealing plug 2046 in the top end forming the annular space 2054 that aligns with the water channel 2036 in the main wall 2028 of the housing 2024, which further aligns with and seals against the median and the water channel in the jet tip (not shown) This allows fluid flow from the fluid channel in the jet tip to enter the annular space 2054 and fill the fluid pocket 2040 between the sealing plug 2036 and the inner wall of the top portion 2032 of the housing 2024 before exiting through the outlet aperture 2016. As the fluid exits the outlet aperture 2016, the radiant energy from the laser diode 2034 is directed by the barrel lens 2038 where it is entrained within the exiting fluid stream by refraction of the light at the interface of the water stream and the air once the water stream leaves the outlet aperture 2016. In these embodiments, the fluid transports and/or directs the radiant energy into the user's mouth for application at the location of the fluid jet spray.

In this exemplary embodiment, the sealing plug 2046 further defines an annular recess 2052 in the outer wall of the sealing plug 2046 adjacent the bottom portion of the axial lumen. An O-ring 2044 or other sealing mechanism may be placed within the annular recess 2052 to seal the sealing plug 2046 against the inner wall of the housing 2024 and preventing fluid from reaching the electrical connection between the pins 2030 and the receptacles within the head of the jet tip.

In some embodiments, the sealing plug 2046 may also act as a heat sink, removing heat from the laser diode 2034. The material used for the sealing plug 2046 (e.g., aluminum or another metal) may be chosen to conduct heat away from the laser diode 2034 and transfer the heat to the fluid in the fluid pocket 2040 that surrounds portions of the sealing plug whereby the heat may be dissipated.

Figure 25:
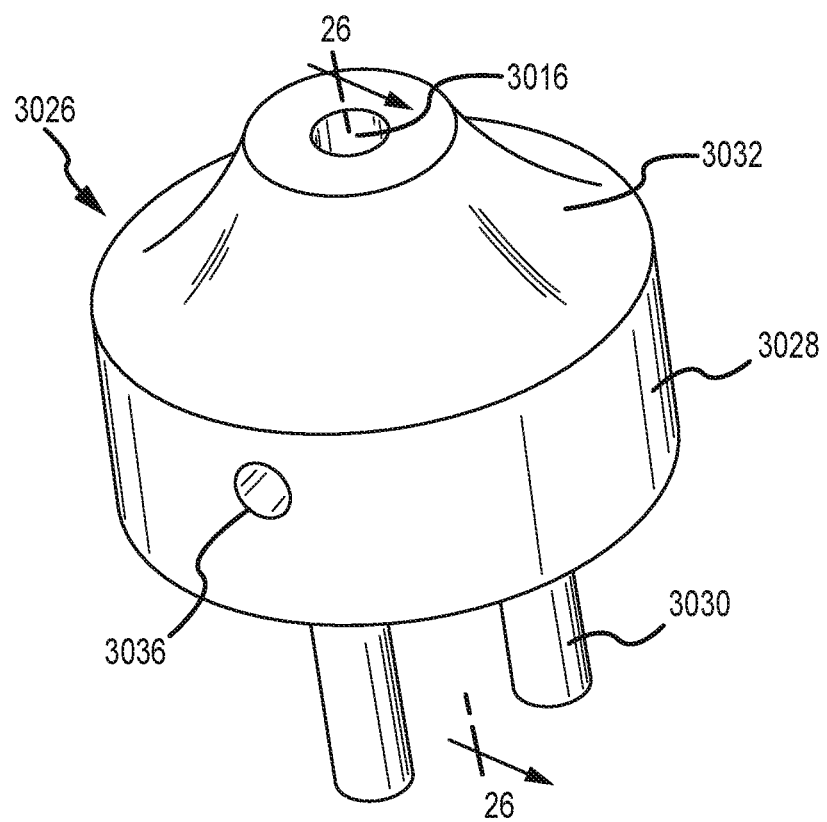
FIG. 25 is an isometric view of another embodiment of a removable radiant energy source removed from the jet tip.
Figure 26:
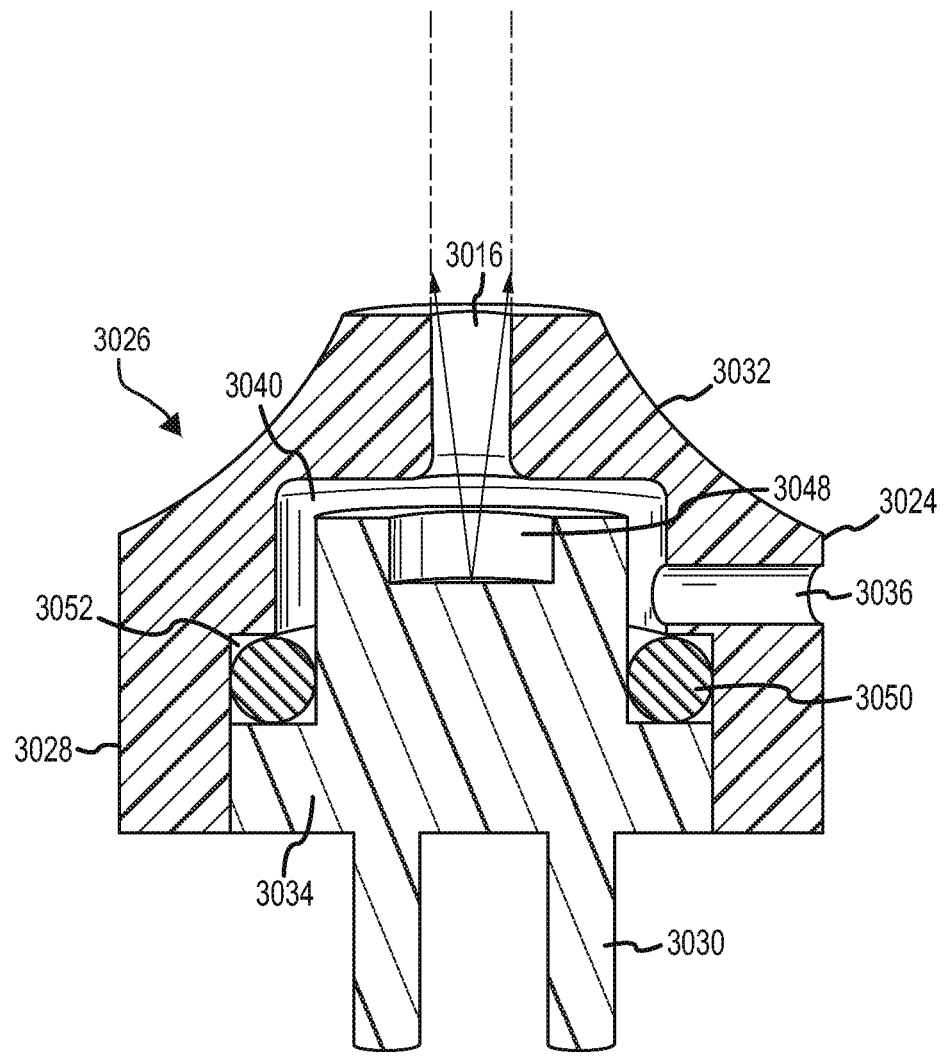
FIG. 26 is a cross-section view of the radiant energy source illustrated in FIG. 25 taken along line 26-26 in FIG. 25.

FIGS. 25 and 26 illustrate a third embodiment of a radiant energy source in the form of a laser diode package 3026. In this embodiment, a laser diode 3034 is mounted within a housing 3024 may be used, and a lens or the like may be omitted. As shown in FIGS. 27 and 28, the housing has a main body 3028 and a top portion 3032 in substantially the same conical form as the embodiment of FIG. 22A. However, in this embodiment, the laser diode package 3026 is not an integrally formed structure within the tip head of the jet tip, but is instead a removable and replaceable unit that can be pressed or snapped within a cavity formed in the tip head. A fluid connecting aperture 3036 is formed within the main body 3028 of the housing 3024 and is aligned to fluidly connect with the water channel in the jet tip. The laser diode 3034 of this exemplary embodiment has two pins 3030 that extend from the bottom of the laser diode 3034 to connect with receptacles in the cavity in the head of the jet tip.

In this exemplary embodiment, the laser diode 3034 is used without a lens. A typical laser diode 3034 produces a substantially collimated, narrow beam of radiant energy from a small light emitting region 3048, and thus the lens and other collimating devices may be omitted. As the light exits the light emitting region 3048 it passes through the fluid pocket 3040 is entrained with fluid exiting the outlet aperture 3016. The fluid surrounded by the air after exiting the outlet aperture 3016 then acts as a light/radiant energy guide, transporting the radiant energy into a user's mouth. In this exemplary embodiment, the fluid in the fluid pocket 3040 is in direct and substantial contact with the laser diode 3034 and may provide sufficient cooling of the laser diode 3034 that a heat sink may be omitted.

As a collimator or lens is omitted in this embodiment, the distance between the outlet aperture 3016 and the light emitting region 3048 may be reduced to ensure a maximum amount of light energy reaches the user's oral tissue. The length of the exit aperture 3016 may also be chosen to maximize the light energy entrained within the exiting fluid flow. As shown in FIG. 26, it may be desirable that the combined distance of the length of the exit aperture and the space between the inner wall of the top portion 3032 and the light emitting region 3048 is shorter than the distance at which the radial dispersion of the light beam is greater than the diameter of the outlet aperture 3016. This is because the wall of the outlet aperture 3016 is often more reflective than the fluid/air interface and creates angles of reflection that are greater than the fluid/air interface can refract and thus more light energy may escape the stream of water. In some instances, if water is used as the fluid within the jet tip 3010, water surrounded by plastic may not be as good of a guide for the radiant energy as water surrounded by air. The angled arrows shown in the outlet aperture 3016 in FIG. 26 indicate the light emitted from the laser diode 3034 has traveled through the outlet aperture 3016 without hitting the sidewalls and will thus be internally refracted within the fluid stream for delivery to the user's oral tissue.

Additionally, the laser diode 3034 may be substantially sealed in the diode package 3026 so as to prevent fluid from coming into contact with the connection pins 3030 extending from the bottom of the laser diode 3034. In the embodiment shown in FIG. 26, the main portion 3028 of the housing 3024 defines a stepped cavity 3052. The laser diode 3034 is similarly stepped such that a narrower diameter portion extends upward into the fluid pocket 3040 while a larger diameter lower portion is substantially the same as the inner diameter of the lower portion of the main portion 3028 of the housing. An O-ring 3050 or other sealing mechanism may be placed in the stepped cavity between the step of the laser diode 3034 and the step of the main portion 3028 of the housing to create a seal that prevents fluids within the fluid pocket 3040 from compromising the electrical connection between the pins 3030 and the corresponding receptacles in the head of the jet tip.

It should be noted that various features illustrated with respect to the various laser diode embodiments may be implemented in other embodiments. For example, the different types of lenses (including with respect to shapes and materials) may be used with multiple housing configurations, regardless of whether the housing is part of a removable package or is integrally formed as part of the head of the jet tip. Further, laser diodes may be used as the radiant energy source within any of the other embodiments illustrated throughout the disclosure, e.g., within the embodiments illustrated in FIGS. 4A-4B.

All directional references (e.g., proximal, distal, upper, lower, upward, downward, left, right, lateral, front, back, top, bottom, above, below, vertical, horizontal, clockwise, and counterclockwise) are only used for identification purposes to aid the reader's understanding of the present invention, and do not create limitations, particularly as to the position, orientation, or use of the invention. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. The exemplary drawings are for purposes of illustration only and the dimensions, positions, order and relative sizes reflected in the drawings attached hereto may vary.

The above specification, examples and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the spirit or scope of this invention. In particular, it should be understood that the described technology may be employed independent of a personal computer. Other embodiments are therefore contemplated. It is intended that all matter contained in the above description and shown in the accompanying drawings shall be interpreted as illustrative only of particular embodiments and not limiting. Changes in detail or structure may be made without departing from the basic elements of the invention as defined in the following claims.

What is claimed is:

1. An oral irrigator comprising:
   a pump mechanism;
   a reservoir in fluid communication with the pump mechanism;
   a jet tip in fluid communication with the pump mechanism and configured for directing a fluid pumped from the reservoir by the pump mechanism through the jet tip at a surface inside an oral cavity, the jet tip including a radiant energy conduit having a proximal end and a distal end and the jet tip defining a fluid conduit coaxial with and housing the radiant energy conduit such that fluid flows through the jet tip in a space between the fluid conduit and the radiant energy conduit;
   a radiant energy source configured to produce radiant energy; and
   a collimator positioned between the radiant energy source and the radiant energy conduit, the collimator configured to collimate the radiant energy from the radiant energy source, wherein the collimator comprises:

a first surface defining a curved surface configured to collect the radiant energy from the radiant energy source; and a second surface opposite of the first surface that defines a flat surface configured to focus the radiant energy into the radiant energy conduit;

wherein the proximal end of the radiant energy conduit is positioned adjacent the collimator source to capture the collimated radiant energy from the collimator and the distal end of the radiant energy conduit directs the collimated radiant energy in generally the same direction as the fluid so as to direct the radiant energy at a surface inside the oral cavity.

2. The oral irrigator of claim 1, wherein the radiant energy source and the jet tip are of unitary construction to direct both the fluid and the collimated radiant energy in generally the same direction.

3. The oral irrigator of claim 1, wherein the reservoir, the pump mechanism, the jet tip, the collimator, and the radiant energy source are integrated as a generally unitary combination.

4. The oral irrigator of claim 1, further comprising:
a base configured to rest on a support surface and defining a storage position; and
a handle configured to rest in the storage position;
wherein the jet tip, the collimator, and the radiant energy source are included on the handle, which is movable from the storage position on the base to a second position at least partially removed from the base.

5. The oral irrigator of claim 1, wherein the radiant energy conduit further comprises a plurality of bumps on an outer surface of the radiant energy conduit to maintain a substantially constant separation distance between the radiant energy conduit and the fluid conduit.

6. The oral irrigator of claim 1, wherein the radiant energy source comprises a light emitting diode.

7. The oral irrigator of claim 1, wherein the radiant energy source generates radiant energy between 350-450 nm.

8. The oral irrigator of claim 1, wherein the radiant energy source generates radiant energy between 375-415 nm.

9. The oral irrigator of claim 1, wherein the radiant energy source generates radiant energy between 405-415 nm.

10. The oral irrigator of claim 1, wherein the collimator is a unitary structure.

11. The oral irrigator of claim 1, wherein the first surface defines a proximal end of the collimator and is positioned adjacent to the radiant energy source and the curved surface comprises a concave surface that transitions into a convex surface, wherein the convex surface is positioned in a central region of the first surface.

12. The oral irrigator of claim 1, wherein the second surface defines a distal end of the collimator and is positioned adjacent to the radiant energy conduit, wherein the second surface further comprises a conical sidewall that extends distally from the flat surface.

13. An oral irrigator comprising:
a pump mechanism;
a reservoir in fluid communication with the pump mechanism;
a handle in fluid communication with the pump mechanism;
a jet tip coupled to the handle, the jet tip in fluid communication with the pump mechanism and configured to direct a fluid pumped from the reservoir by the pump mechanism through the jet tip at a surface inside an oral cavity;
a radiant energy source positioned in the handle and configured to produce radiant energy; and
a collimator positioned between the radiant energy source and the jet tip, comprising:
a proximal end defining a curved surface configured to collimate the radiant energy from the radiant energy source; and
a distal end defining a flat surface configured to focus the radiant energy so as to direct the radiant energy through the jet tip to the surface inside the oral cavity.

14. The oral irrigator of claim 13, wherein:
the jet tip includes a fluid conduit having a terminal end for directing a stream of the fluid therefrom; and
the radiant energy source and the collimator are positioned adjacent a proximal end of the fluid conduit to direct the collimated radiant energy in generally the same direction as the fluid stream.

15. The oral irrigator of claim 13, wherein the jet tip includes a fluid conduit having a terminal end for directing a stream of the fluid therefrom and a radiant energy conduit having a proximal end positioned adjacent the collimator, extending adjacent the fluid conduit, and terminating adjacent the terminal end of the fluid conduit for directing the collimated radiant energy in generally the same direction as the fluid stream.

16. The oral irrigator of claim 15, wherein the radiant energy conduit is configured to direct the collimated radiant energy into the fluid stream.

17. The oral irrigator of claim 13, wherein:
the jet tip includes a radiant energy conduit having a proximal end positioned adjacent the collimator to capture the collimated radiant energy from the radiant energy source, and a distal end that directs the collimated radiant energy in generally the same direction as the fluid; and
the radiant energy conduit with the jet tip defines a lumen that functions as a fluid conduit to flow fluid through the jet tip and direct a stream of the fluid therefrom.

18. The oral irrigator of claim 17, wherein the radiant energy conduit is configured to direct radiant energy emitted from its distal end into the fluid stream exiting the lumen.

19. The oral irrigator of claim 13, wherein:
the jet tip includes a radiant energy conduit having a proximal end positioned near the radiant energy source to capture the collimated radiant energy from the collimator, and a distal end that directs the collimated radiant energy in generally the same direction as the fluid; and
the jet tip further defines a fluid conduit coaxial with and housing the radiant energy conduit such that fluid flows through the jet tip in a space between the fluid conduit and the radiant energy conduit.

20. The oral irrigator of claim 19, wherein the radiant energy conduit is configured to direct radiant energy emitted from a distal end of the radiant energy conduit into the fluid stream exiting the jet tip.

21. The oral irrigator of claim 19, wherein the radiant energy conduit comprises a light guide.

22. The oral irrigator of claim 19, wherein the radiant energy conduit includes a plurality of bumps on an outer surface of the radiant energy conduit to maintain a substantially constant separation distance between the radiant energy conduit and the fluid conduit.

23. The oral irrigator of claim 13, wherein the radiant energy source comprises a light emitting diode that emits light between 350 nm and 450 nm.

* * * * *